(12) United States Patent
Andrews et al.

(10) Patent No.: US 12,038,434 B2
(45) Date of Patent: Jul. 16, 2024

(54) DEVICES, SOLUTIONS AND METHODS FOR SAMPLE COLLECTION RELATED APPLICATIONS, ANALYSIS AND DIAGNOSIS

(71) Applicant: DNA Genotek, Inc., Ottawa (CA)

(72) Inventors: Stephen Andrews, Falmouth, ME (US); Youssef Biadillah, Geneva (CH); Manasi Jain, Portland, ME (US); David S. Frank, Springfield, NJ (US); John R Zeman, Springfield, NJ (US); Charles T. Tackney, Springfield, NJ (US)

(73) Assignee: DNA Genotek, INC., Ottawa (CA)

( * ) Notice: Subject to any disclaimer, the term of this patent is extended or adjusted under 35 U.S.C. 154(b) by 0 days.

(21) Appl. No.: 15/549,975

(22) PCT Filed: Feb. 9, 2016

(86) PCT No.: PCT/US2016/017147
§ 371 (c)(1),
(2) Date: Aug. 9, 2017

(87) PCT Pub. No.: WO2016/130543
PCT Pub. Date: Aug. 18, 2016

(65) Prior Publication Data
US 2018/0031543 A1    Feb. 1, 2018

(30) Foreign Application Priority Data

| Feb. 9, 2015 | (EP) | 15154381 |
| Apr. 17, 2015 | (EP) | 15164155 |
| Apr. 21, 2015 | (EP) | 15164567 |
| Jun. 21, 2015 | (EP) | 15173040 |
| Nov. 28, 2015 | (EP) | 15196908 |
| Feb. 1, 2016 | (EP) | 16153712 |

(51) Int. Cl.
*G01N 33/50*    (2006.01)
*G01N 33/543*    (2006.01)

(52) U.S. Cl.
CPC ..... *G01N 33/5091* (2013.01); *G01N 33/5005* (2013.01); *G01N 33/54393* (2013.01); *G01N 2333/16* (2013.01); *G01N 2333/70514* (2013.01); *G01N 2333/70517* (2013.01)

(58) Field of Classification Search
None
See application file for complete search history.

(56) References Cited

U.S. PATENT DOCUMENTS

| 4,386,696 A | 6/1983 | Goncalves |
| 5,196,182 A | 3/1993 | Ryan |
| 5,478,722 A | 12/1995 | Caldwell |
| 5,788,652 A | 8/1998 | Rahn |
| 5,871,905 A | 2/1999 | Thieme et al. |
| 6,149,866 A | 11/2000 | Luotola et al. |
| 6,235,466 B1 * | 5/2001 | Branch ..... C12Q 1/42 424/160.1 |
| 6,291,178 B1 * | 9/2001 | Schneider ..... A61B 10/0051 424/150.1 |
| 6,294,349 B1 * | 9/2001 | Streckfus ..... G01N 33/57415 435/7.1 |
| 6,310,195 B1 | 10/2001 | Colucci et al. |
| 6,533,113 B2 | 3/2003 | Moscovitz |
| 6,582,415 B1 | 6/2003 | Fowles et al. |
| 6,667,053 B1 | 12/2003 | Ahmad et al. |
| 6,913,932 B2 | 7/2005 | Maples et al. |
| 7,267,980 B1 | 9/2007 | Mortari et al. |
| 7,300,632 B2 | 11/2007 | Sugiyama et al. |
| 7,482,116 B2 | 1/2009 | Birnboim |
| 7,666,609 B1 | 2/2010 | Guo et al. |
| 7,749,757 B1 | 7/2010 | Mortari et al. |
| 7,927,611 B2 | 4/2011 | Campos-Neto et al. |
| 8,486,909 B2 | 7/2013 | Rennard et al. |
| 8,551,016 B2 | 10/2013 | Slowey et al. |
| 8,796,028 B2 | 8/2014 | Hollander |
| 9,442,046 B2 | 9/2016 | Biadillah et al. |
| 10,576,468 B2 | 3/2020 | Biadillah et al. |
| 11,002,646 B2 | 5/2021 | Biadillah et al. |

(Continued)

FOREIGN PATENT DOCUMENTS

| CN | 101 509 041 A | 8/2009 |
| CN | 201348573 Y | 11/2009 |

(Continued)

OTHER PUBLICATIONS

Yigla et al. Oxidative Stress Indices in COPD—Broncho-Alveolar Lavage and Salivary Analysis. Archives of Oral Biology, 2007. 52: 36-43.*
Vidovic et al. Determination of Leukocyte subsets in human saliva by flow cytometry. Archives of Oral Biology, 2012. 57: 577-583.*
Baron et al. Why is HIV Rarely Transmitted by Oral Secretions? Saliva Can Disrupt Orally Shed, Infected Leukocytes. Arch Intern Med. 1999. 159: 303-310.*

(Continued)

*Primary Examiner* — Allison M Fox
(74) *Attorney, Agent, or Firm* — Cooley LLP

(57) ABSTRACT

A solution is described for preserving cells and/or extracellular components in naturally expressed bodily fluids (e.g. saliva, sputum, urine) for further downstream analysis and/or for diagnosis of a medical condition. The solution may be hypertonic with respect to blood. Techniques are described for enriching cells from a sample of a naturally expressed bodily fluid, and/or for analysis, e.g. to diagnose medical conditions such as cancer, obesity, infections, autism, Alzheimer disease, hetotological disorders, cardiovascular disease or disorders, diabetes, vulnerable plack, LTBI, HIV infection, COPD, ACQS.

18 Claims, 4 Drawing Sheets

(56) References Cited

U.S. PATENT DOCUMENTS

| | | |
|---|---|---|
| 11,536,632 B2 | 12/2022 | Biadillah et al. |
| 11,549,870 B2 | 1/2023 | Biadillah et al. |
| 11,592,368 B2 | 2/2023 | Biadillah et al. |
| 2001/0023072 A1 | 9/2001 | Crawford et al. |
| 2002/0064802 A1 | 5/2002 | Raschke et al. |
| 2003/0119077 A1 | 6/2003 | Ts'o et al. |
| 2004/0038424 A1 | 2/2004 | Maples |
| 2004/0200740 A1 | 10/2004 | Cho |
| 2004/0200741 A1 | 10/2004 | Cho |
| 2004/0226835 A1 | 11/2004 | Takahashi et al. |
| 2005/0059163 A1 | 3/2005 | Dastane et al. |
| 2005/0227303 A1 | 10/2005 | Guo et al. |
| 2006/0280650 A1 | 12/2006 | Wong et al. |
| 2007/0218512 A1 | 9/2007 | Strongin et al. |
| 2008/0280772 A1* | 11/2008 | Wong ............... G01N 33/5017 435/6.14 |
| 2008/0311214 A1 | 12/2008 | Rao |
| 2009/0100944 A1 | 4/2009 | Newby |
| 2009/0205506 A1 | 8/2009 | Lin |
| 2009/0216213 A1 | 8/2009 | Muir et al. |
| 2009/0297558 A1 | 12/2009 | Raviv et al. |
| 2010/0137741 A1 | 6/2010 | Slowey et al. |
| 2010/0179072 A1 | 7/2010 | Yount |
| 2012/0141341 A1 | 6/2012 | Bartfeld et al. |
| 2013/0053254 A1* | 2/2013 | Hollander ........... C12N 15/1003 506/2 |
| 2014/0120531 A1* | 5/2014 | Biadillah ........... A61B 10/0051 435/6.1 |
| 2014/0228233 A1 | 8/2014 | Pawlowski et al. |
| 2014/0336159 A1 | 11/2014 | Clark et al. |
| 2017/0016807 A1 | 1/2017 | Biadillah et al. |
| 2018/0313726 A1 | 11/2018 | Biadillah et al. |
| 2020/0398267 A1 | 12/2020 | Biadillah et al. |
| 2022/0042883 A1 | 2/2022 | Biadillah et al. |
| 2022/0113230 A1 | 4/2022 | Biadillah et al. |

FOREIGN PATENT DOCUMENTS

| | | |
|---|---|---|
| CN | 101955998 A | 1/2011 |
| CN | 102032998 A | 4/2011 |
| CN | 103 890 163 A | 6/2014 |
| EP | 0 240 341 A2 | 10/1987 |
| EP | 1 248 106 A1 | 10/2002 |
| JP | S62-253395 A | 11/1987 |
| JP | S63-070954 U | 5/1988 |
| JP | H09-500723 A | 1/1997 |
| JP | 09-193977 | 7/1997 |
| JP | H10-132824 A | 5/1998 |
| JP | H10-273161 A | 10/1998 |
| JP | H10-512140 A | 11/1998 |
| JP | 10-332734 | 12/1998 |
| JP | 2000-501191 A | 2/2000 |
| JP | 2000-501931 A1 | 2/2000 |
| JP | 2000-508171 A | 7/2000 |
| JP | 2001-524321 A | 12/2001 |
| JP | 2002-156317 A | 5/2002 |
| JP | 2002-514084 A | 5/2002 |
| JP | 2002-357599 A | 12/2002 |
| JP | 2003-344232 A | 12/2003 |
| JP | 2005-536550 A | 12/2005 |
| JP | 2008-545418 A | 12/2008 |
| JP | 2009-051555 A | 3/2009 |
| JP | 2009-518244 A | 5/2009 |
| JP | 2009-522542 A | 6/2009 |
| JP | 2010-213660 A | 9/2010 |
| JP | 2011-36247 A | 2/2011 |
| JP | 2012-523572 A | 10/2012 |
| JP | 2014-256032 A | 10/2014 |
| JP | 2014-531902 A | 12/2014 |
| JP | 2015-500988 A | 1/2015 |
| JP | 59-66756 B2 | 8/2016 |
| WO | WO 94/29691 A | 12/1994 |
| WO | WO 96/14017 A1 | 5/1996 |
| WO | WO 96/20403 A1 | 7/1996 |
| WO | WO 97/21102 A1 | 6/1997 |
| WO | WO 97/38313 A1 | 10/1997 |
| WO | WO 97/48492 A1 | 12/1997 |
| WO | WO 98/44158 A1 | 10/1998 |
| WO | WO 98/53075 A2 | 11/1998 |
| WO | WO 99/27139 A1 | 6/1999 |
| WO | WO 03/104251 A2 | 12/2003 |
| WO | WO 2004/017895 A2 | 3/2004 |
| WO | WO 2004/046348 A1 | 6/2004 |
| WO | WO 2006/072803 A2 | 7/2006 |
| WO | WO 2006/128192 A2 | 11/2006 |
| WO | WO 2010/064634 A1 | 6/2010 |
| WO | WO 2010/090030 A1 | 8/2010 |
| WO | WO 2010/120818 A2 | 10/2010 |
| WO | WO 2012/170711 A1 | 12/2012 |
| WO | WO 2012/177656 A2 | 12/2012 |
| WO | WO-2012177656 A2 * | 12/2012 ......... A61B 10/0096 |
| WO | WO 2013/041854 A1 | 3/2013 |
| WO | WO 2013/045457 A1 | 4/2013 |
| WO | WO 2013/083687 A1 | 6/2013 |
| WO | WO 2014/049022 A1 | 4/2014 |
| WO | WO 2014/146781 A1 | 9/2014 |
| WO | WO 2015/112496 A2 | 7/2015 |

OTHER PUBLICATIONS

Pink et al. Saliva as a Diagnostic Medium. Biomed Pap Med Fac Univ Palacky Olomouc Czech Repub, 2009. 153(2): 103-110.*

Zhang et al. Salivary Transcriptome Biomarkers for Detection of Resectable Pancreatic Cancer. Gastroenterology, 2010. 138(3): 949-957.*

Xiao et al. Proteomic Analysis of Human Saliva From Lung Cancer Patients Using Two-Dimensional Difference Gel Electrophoresis and Mass Spectrometry. Molecular & Cellular Proteomics, 2012. 11: 1-12.*

Bryant et al. KRAS: Feeding Pancreatic Cancer Proliferation. Trends in Biological Sciences, 2014. 39(2): 91-100.*

Bonne et al., Genome Medicine, 2012, 4:82. (Year: 2012).*

Zhang et al., PLoS One, 2010, 5(12):e15573 (Year: 2010).* http://www.abcam.com/primary-antibodies/new-resources-guide-for-imaging-reagents, accessed on Oct. 8, 2019, 24 pages.

https://www.aidsmap.com/Accuracy/page/1323395?#ref1323397, Jun. 2019, 4 pages.

http://www.aidsmap.com/Large-US-study-shows-which-HIV-tests-are-most-accurate/page/2812847/, Jan. 2014, 2 pages.

https://www.aidsmap.com/Saliva/page/1322841/, Jul. 2019, 3 pages.

http://www.catie.ca/en/pif/spring-2014/hiv-home-based-testing-potential-benefits-and-ongoing-concerns, 2014, 3 pages.

https://www.cdc.gov/hiv/testing/clinical/, Apr. 22, 2019, 4 pages.

https//www.genome.gov/10000206, Fluorescence In Situ Hybridization Fact Sheet, accessed on Oct. 9, 2019, 2 pages.

https://www.cdc.gov/hiv/pdf/testing/hiv-tests-advantages-disadvantages_1.pdf, accessed on Oct. 8, 2019, 7 pages.

http://www.gsk.com/en-gb/media/press-releases/2014/gsk-data-presented-at-ers-demonstrate-potential-of-blood-eosinophil-levels-to-help-inform-copd-treatment-decisions/, Sep. 8, 2014, 7 pages.

http://www.lungcancerprofiles.com, accessed on Oct. 8, 2019, 2 pages.

http://www.mycancergenome.org/content/disease/lung-cancer/egfr/, 2010-2017, 8 pages.

https://pharmaintelligence.informa.com/products-and-services/data-and-analysis/datamonitor-healthcare, 2019, 3 pages.

http://www.pm360online.com/liquid-biopsy-consistent-with-tumor-biopsy-for-nsclc/, by Jennifer Kelly Shepphird, Feb. 26, 2015, 2 pages.

https://www.questdiagnostics.com/home/physicians/testing-services/specialists/hospitals-lab-staff/specimen-handling/immunohistochemistry.html, 2000-2019, 8 pages.

http://www.uptodate.com/contents/anaplastic-lymphoma-kinase-alk-fusion-oncogene-positive-non-small-cell-lung-cancer, 2019, 10 pages.

Abdolmaleky, H. M. et al., "Genetics and Epigenetics in Major Psychiatric Disorders," Am J Pharmacogenomics, 5(3): 149-160 (2005).

(56) References Cited

OTHER PUBLICATIONS

Balamane, M. et al., "Detection of HIV-1 in Saliva: Implications for Case-Identification, Clinical Monitoring and Surveillance for Drug Resistance," The Open Virology Journal, 4:88-93 (2010).
Buckingham, L., Molecular Diagnostics Fundamentals, Methods and Clinical Applications, Second Edition, Chapter 7, Nucleic Acid Amplification, F. A. Davis Company, 2012, 40 pages.
Burdge, G. C. & Lillycrop, K. A., "Nutrition, Epigenetics, and Developmental Plasticity: Implications for Understanding Human Disease," Annu. Rev. Nutr., 30:315-339 (2010), and Fig. 1, 1 page.
Casado, B. et al., "Advances in proteomic techniques for biomarker discovery in COPD," Expert Rev. Clin. Immunol, 7(1):111-123 (2011).
Chouliaras, L. et al., "Epigenetic regulation in the pathophysiology of Alzheimer's disease," Progress in Neurobiology, 90(4):498-510 (2010).
Costa, E. et al., "Epigenetic Downregulation of GABAergic Function in Schizophrenia: Potential for Pharmacological Intervention?" Mol Interv., 3(4):220-229 (2003).
Dako Danemark A/S 2013. IHC Guidebook, Sixth Edition, Immunohistochemical Staining Methods, 2013, 218 pages.
Di Stefano, A. et al., "Association of increased CCL5 and CXCL7 chemokine expression with neutrophil activation in severe stable COPD," Thorax, 64:968-975 (2009).
Dos-Santos, M. C. et al., "Cell phenotyping in saliva of individuals under psychological stress," Cellular Immunology, 260:39-43 (2009).
Eaves, L. et al., "Resolving multiple epigenetic pathways to adolescent depression," Journal of Child Psychology and Psychiatry, 44(7): 1006-1014 (2003).
Even-Desrumeaux, K. et al., "State of the Art in Tumor Antigen and Biomarker Discovery," Cancers, 3:2554-2596 (2011).
Faner, R. et al., "Lessons from ECLIPSE: a review of COPD biomarkers," Thorax, 69:666-672 (2014).
Feng, W., "Identification of Human Lung Cancer Stem Cell Markers," 2010 Research Grant program Winning Abstract, 2 pages.
Gaester, K. et al., "Human papillomavirus infection in oral fluids of HIV-1-positive men: prevalence and risk factors," Scientific Reports, 4:6592 (2014), 5 pages; doi: 10.1038/srep06592.
George, L. & Brightling, C. E., "Eosinophilic airway inflammation: role in asthma and chronic obstructive pulmonary disease," Ther Adv Chronic Dis, 7(1): 34-51 (2016).
Gernez, Y. et al., "Neutrophils in chronic inflammatory airway diseases: can we target them and how?" Eur Respir J, 35:467-469 (2010).
Hemmes, M. et al., Abstract: "Specimen Collection Within the Cancer Research Network: A Critical Appraisal," Clin Med Res., 8(3-4):191, 1 page.
Ho, S.-M., "Environmental epigenetics of asthma: An update," J Allergy Clin Immunol, 126(3):453-465 (2010).
Iwamoto, K. & Kato, T., "Epigenetic Profiling in Schizophrenia and Major Mental Disorders," Neuropsychobiology, 60:5-11 (2009).
Javaid, M. A. et al., "Saliva as a diagnostic tool for oral and systemic diseases," Journal of Oral Biology and Craniofacial Research, 6:67-75 (2016).
Johnson, L. J. & Tricker, P. J., "Epigenomic plasticity within populations: its evolutionary significance and potential," Heredity, 105:113-121 (2010).
Kappeler, L. & Meaney, M. J., "Epigenetics and parental effects," Bioessays, 32:818-827 (2010).
Kerr, K. M. et al., "Second ESMO consensus conference on lung cancer: pathology and molecular biomarkers for non-small-cell lung cancer," Annals of Oncology, 25:1681-1690 (2014).
Korpanty, G. J. et al., "Biomarkers that currently affect clinical practice in lung cancer: EGFR, ALK, MET, ROS-1, and KRAS," Frontiers in Oncology, 4:204 (2014), 8 pages; doi: 10.3389/fonc.2014.00204.
Koutsokera, A. et al., "Pulmonary biomarkers in COPD exacerbations: a systematic review," Respiratory Research, 14:111 (2013), 12 pages; http://respiratory-research.com/content/14/1/111.

Kuratomi, G et al., "Aberrant DNA methylation associated with bipolar disorder identified from discordant monozygotic twins," Molecular Psychiatry, 13:429-441 (2008).
Lal, R. B. et al., "Fixation and Long-Term Storage of Human Lymphocytes for Surface Marker Analysis by Flow Cytometq," Cytometry, 9:213-219 (1988).
Lassen, K. G. et al., "Analysis of Human Immunodeficiency Virus Type 1 Transcriptional Elongation in Resting CD4+ T Cells In Vivo," Journal of Virology, 78(17):9105-9114 (2004).
Lister, R. et al., "Human DNA methylomes at base resolution show widespread epigenomic differences," Nature, 462:315-322 (2009).
Markman, M. "Genetics of Non-Small Cell Lung Cancer," Aug. 21, 2019, 6 pages; https://emedicine.medscape.com/article/1689988-print.
Matos-Gomes, N. et al., "Psychological Stress and Its Influence on Salivary Flow Rate, Total Protein Concentration and IgA, IgG and IgM Titers," Neuroimmunomodulation, 17:396-404 (2010).
Maunakea, A. K. et al., "Epigenome Mapping in Normal and Disease States," Circ Res., 107:327-339 (2010).
Mastroeni, D. et al., "Epigenetic changes in Alzheimer's disease: Decrements in DNA methylation," Neurobiology of Aging, 2025-2037 (2010).
McGowan, P. O. & Kato, T., "Epigenetics in mood disorders," Environ Health Prev Med, 13:16-24 (2008).
McGowan, P. O. et al., "Epigenetic regulation of the glucocorticoid receptor in human brain associates with childhood abuse," Nature Neuroscience, 12(3):342-348 (2009).
McGowan, P. O. & Szyf, M., "The epigenetics of social adversity in early life: Implications for mental health outcomes," Neurobiology of Disease, 39:66-72 (2010).
Mens, H. et al., "Amplifying and Quantifying HIV-1 RNA in HIV Infected Individuals with Viral Loads Below the Limit of Detection by Standard Clinical Assays," J Vis Exp., (55):2960 (2011), 8 pages; doi: 10.3791/2960.
Mill, J. & Petronis, A., "Molecular studies of major depressive disorder: the epigenetic perspective," Molecular Psychiatry, 12:799-814 (2007).
Noguera, A. et al., "Enhanced neutrophil response in chronic obstructive pulmonary disease," Thorax, 56:432-437 (2001).
O'Neil, J. D et al., "HIV Nucleic Acid Amplification Testing Versus Rapid Testing: It Is Worth the Wait. Testing Preferences of Men Who Have Sex with Men," J Acquir Immune Defic Syndr., 60(4):e119-e122 (2012); doi: 10.1097/QAI.0b013e31825aab51.
Peedicayil, J., "The role of epigenetics in mental disorders," Indian J Med Res, 126:105-111 (2007).
Petronis, A. et al., "Schizophrenia: An Epigenetic Puzzle?" Schizophrenia Bulletin, 25(4):639-655 (1999).
Plazas-Mayorca, M. D. & Vrana, K. E., "Proteomic Investigation of Epigenetics in Neuropsychiatric Disorders: A Missing Link between Genetics and Behavior?" Journal of Proteome Research, 10:58-65 (2011).
Portela, A. & Esteller, M., "Epigenetic modifications and human disease," Nature Biotechnology, 28(10):1057-1068 (2010).
Reynolds, J. D. et al., "Comparison of high density genotyping results from saliva and blood samples on Affymetrix GeneChip® GenomeWide SNP 6.0 arrays," Poster, 1 page.
Righini, C. A. et al., "Tumor-Specific Methylation in Saliva: A Promising Biomarker for Early Detection of Head and Neck Cancer Recurrence," Clin Cancer Res, 13(4):1179-1185 (2007).
Romanus, D. et al., "Cost-Effectiveness of Multiplexed Predictive Biomarker Screening in Non-Small-Cell Lung Cancer," J Thorac Oncol., 10:586-594 (2015).
Rosas, S. L. B. et al., "Promoter Hypermethylation Patterns of p16, $O^6$-ethylguanine-DNAmethyltransferase, and Death-associated Protein Kinase in Tumors and Saliva of Head and Neck Cancer Patients," Cancer Research, 61:939-942 (2001).
Russo, P. et al., "Heritability of body weight: Moving beyond genetics," Nutrition, Metabolism & Cardiovascular Diseases, 20:691-697 (2010).
Saha, S. & Brightling, C. E., "Eosinophilic airway inflammation in COPD," International Journal of COPD, 1(1):39-47 (2006).

(56) References Cited

OTHER PUBLICATIONS

Schilter, H. C. et al., "Effects of an anti-inflammatory VAP-1/SSAO inhibitor, PXS-4728A, on pulmonary neutrophil migration," Respiratory Research, 16:42 (2015), 14 pages; doi:10.1186/s12931-015-0200-z.
Shaya, F. T. et al., "Burden of COPD, Asthma, and Concomitant COPD and Asthma Among Adults," Chest, 136:405-411 (2009).
Sindhu, S. et al., "Saliva: A Cutting Edge in Diagnostic Procedures," Journal of Oral Diseases, vol. 2014, Article ID 168584 (May 2014), 8 pages; http://dx.doi.org/10.1155/2014/168584.
Singh, D. et al., "Eosinophilic inflammation in COPD: prevalence and clinical characteristics," European Respiratory Journal, 44:1697-1700 (2014).
Singh, D. et al., "Sputum neutrophils as a biomarker in COPD: findings from the ECLIPSE study," Respiratory Research, 11:77 (2010), 12 pages; doi:10.1186/1465-9921-11-77.
Sterlacci, W. et al., "Putative Stem Cell Markers in Non-Small-Cell Lung Cancer A Clinicopathologic Characterization," J Thorac Oncol., 9:41-49 (2014).
Thunnissen, F. B. J. M., "Sputum examination for early detection of lung cancer," J Clin Pathol, 56:805-810 (2003).
Tierling, S. et al., "DNA methylation studies on imprinted loci in a male monozygotic twin pair discordant for Beckwith-Wiedemann syndrome," Clin Genet, 79:546-553 (2011).
Tsai, S.-J. et al., "Recent molecular genetic studies and methodological issues in suicide research," Progress in Neuro-Psychopharmacology & Biological Psychiatry, 35:809-817 (2011).
Viet, C. T. & Schmidt, B. L., "Methylation Array Analysis of Preoperative and Postoperative Saliva DNA in Oral Cancer Patients," Cancer Epidemiol Biomarkers Prev, 17(12):3603-3611 (2008).
Vlaanderen, J. et al., "Application of OMICS technologies in occupational and environmental health research; current status and projections," Occup Environ Med, 67:136-143 (2010).
Vyboh, K. et al., "Detection of Viral RNA by Fluorescence in situ Hybridization (FISH)," J. Vis. Exp., 63:e4002 (2012), 5 pages; doi:10.3791/4002.
Wang, D. O. et al., "A quick and simple FISH protocol with hybridization-sensitive fluorescent linear oligodeoxynucleotide probes," RNA, 18:166-175 (2012).
Welham, M. J., "VAP-1: a new anti-inflammatory target?" Blood, 103(9):3250-3251 (2004).
Wu, H. et al., "Is CD133 Expression a Prognostic Biomarker of Non-Small-Cell Lung Cancer? A Systematic Review and Meta-Analysis," PLoS ONE 9(6): e100168 (2014), 8 pages; doi: 10.1371/journal.pone.0100168.
Yamamoto, C. et al., "Airway Inflammation in COPD Assessed by Sputum levels of Interleukin-8," Chest, 112:505-510 (1997).
Yang, J. et al., "Detection of Tumor Cell-Specific mRNA and Protein in Exosome-Like Microvesicles from Blood and Saliva," PLoS One, 9(11): e110641 (2014), 10 pages; doi:10.1371/journal.pone.0110641.
Zhang, F. F. et al., "Physical activity and global genomic DNA methylation in a cancer-free population," Epigenetics, 6(3):293-299 (2011).
Casado et al., "Advances in Proteomic Techniques for Biomarker Discovery in COPD," Expert Rev Clin Immunol. 2011; 7(1):111-123, 15 pages.
Anonymous: "Paraformaldehyde Fixation of Cells", BUMC-Flow Cytometry Core Facility, downloaded from http://www.bu.edu/flow-cytometry/files/2010/10/Paraformaldehyde-Fixation-of-cells.doc, Mar. 7, 2007, pp. 1-4.
Bryant, K. L. et al., "KRAS: feeding pancreatic cancer proliferation," Trends in Biochemical Sciences, 39(2):91-100 (2014).
Langel, K. et al., "Drug Testing in Oral Fluid—Evaluation of Sample Collection Devices", Journal of Analytical Toxicology, vol. 32, Jul./Aug. 2008, pp. 393-401.

* cited by examiner

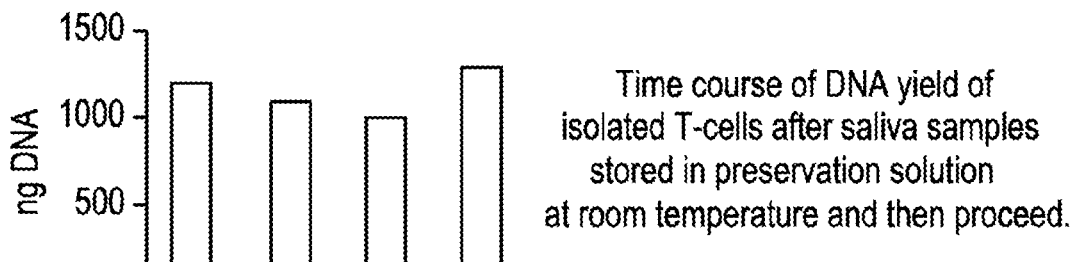
Time course of DNA yield of isolated T-cells after saliva samples stored in preservation solution at room temperature and then proceed.
DNA extracted from isolated T-cells after stored in preservation solution for indicated time.
FIG. 2
FIG. 3
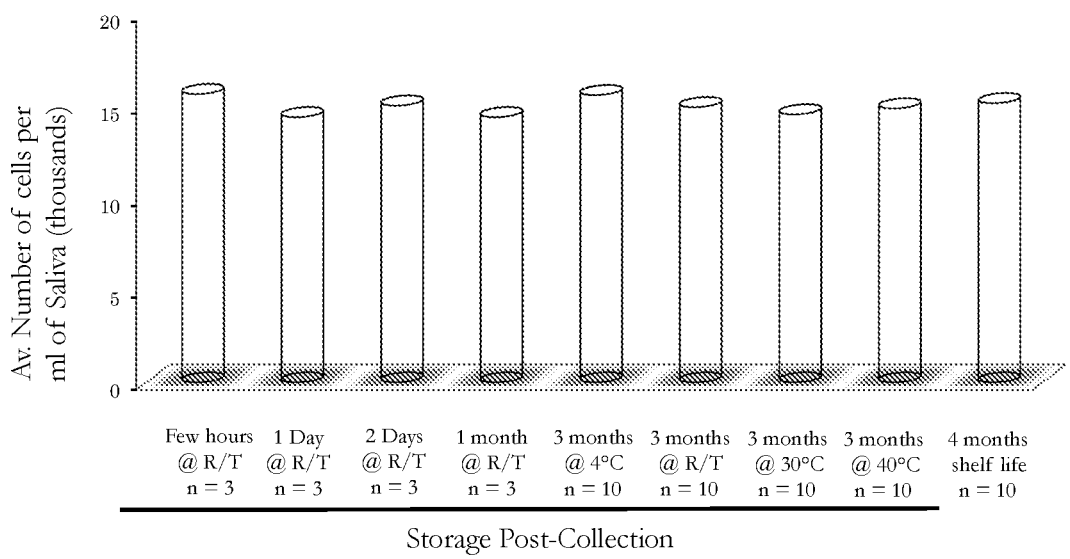

FIG. 7
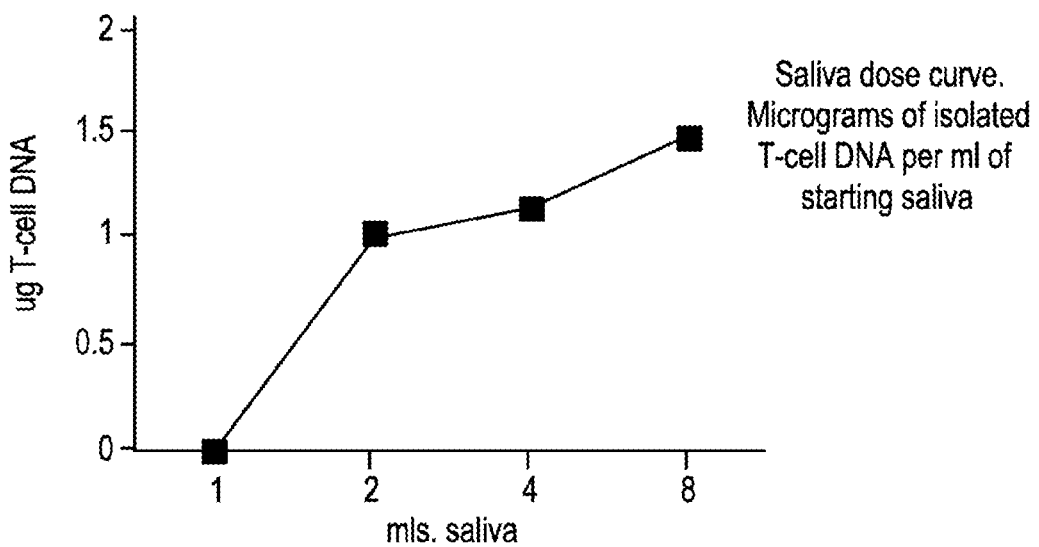
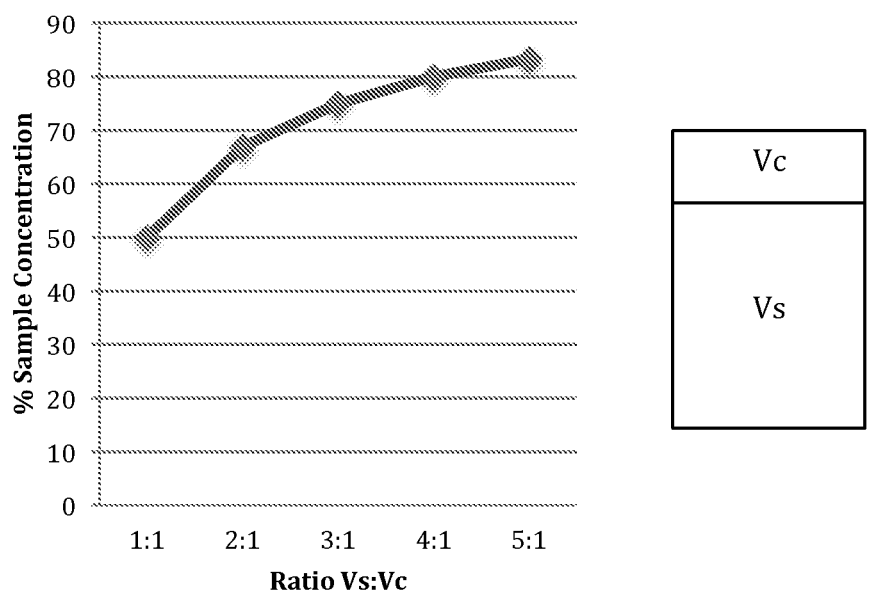
FIG. 8

DEVICES, SOLUTIONS AND METHODS FOR SAMPLE COLLECTION RELATED APPLICATIONS, ANALYSIS AND DIAGNOSIS

FIELD OF THE DISCLOSURE

The disclosure relates to devices, solutions and methods for collecting samples of bodily fluids or other substances, including hazardous and/or toxic substances, and in particular, a naturally expressed bodily fluid (e.g., oral fluids, urine). Additionally or alternatively, the disclosure relates generally to preservation of cells and/or extra-cellular components from such fluids. Additionally or alternatively, the disclosure relates generally to functional genomics. Additionally or alternatively, the disclosure relates to the isolation and/or preservation of cells and/or extra-cellular components from such bodily fluids, for studies in any of: diagnostics, genetics, functional genomics, epigenetic studies, and biomarker discovery (for example). Additionally or alternatively, the disclosure relates to the detection of diseases or infection by using a naturally expressed bodily fluid.

BACKGROUND

Personalized medicine is the customization of treatment to an individual as opposed to the one treatment-for-all model. Personalized medicine involves categorizing a patient based on his or her physical condition and designing an optimal healthcare solution exclusively for that category. The progression of personalized medicine is dependent on the discovery, validation, and commercialization of biomarkers to stratify populations for treatment and for the development of diagnostics for screening and early disease detection.

Epigenetic research has come to the forefront of medical research and is implicated in the etiology of a number of physical and mental illnesses including: cancer, obesity, diabetes, schizophrenia, and Alzheimer's disease (Alike et al, 2010; Grant et al. 2010; McGowen et al., 2009; McGowen and Szyf, 2010; Plazas-Mayorca and Vrana, 2011; and Portela and Esteller, 2010). In addition, Epigenetics may hold particular promise in many scientific and medical areas including but not limited to: cancer, diabetes, drug integrations, drug effectiveness, childhood aggression, suicidal behaviors, aging, inflammation, pain, obesity, schizophrenia, and other mental illnesses (Abdolmaleky et al., 2005; Costa et al., 2003; Iwamoto & Kato, 2009; Kuratomi et al., 2007; McGowan & Kato, 2007; McGowen and Szyf, 2010; Peedicayil, 2007; Petronis et al., 1999; McGowen and Szyf, 2010; Plazas-Mayorca and Vrana, 2011; and Zawia et al., 2009).

A major challenge in the field includes the identification of an appropriate source material for home-based sample collection that is adequate for large-scale epigenetic research including whole-genome-analysis studies. Epigenetics may be the key to understanding the mechanisms of gene-environment interactions, as growing evidence suggests that epigenetic mechanisms may provide a molecular memory of environmental experiences (Ho, 2010; Kappeler and Meaney, 2010; McGowen et al., 2009; McGowen and Szyf, 2010; Portela and Esteller, 2010; Richards, 2008; Russo et al., 2010; Tsai et al., 2010; and Vlaanderen et al., 2010). Preliminary data from some humans suggest that distinct methylation patterns in peripheral blood cells are associated with social behaviors including: childhood aggression, suicidal behaviors, and ageing (Kappeler and Meaney, 2010; McGowen et al., 2009; McGowen and Szyf, 2010; Portela and Esteller, 2010; Russo et al., 2010; Tierling et al., 2010; Tsai et al., 2010; and Zhang et al., 2011).

Due at least in part to the heterogeneous nature of human disease, particularly mental illness, and the complex interaction of contributing etiological factors, studies require large sample sizes to provide reliable and significant effects. However, current research options for sample collection for epigenetic studies do not meet this requirement of "large sample sizes." The need for large sample sizes for studies is also true in order to produce significant effects in regards to studying human-environment interactions, as these interactions are also of a very complex nature with many contributing factors. The ability to perform large-scale "population sized" (subject samples numbering in at least the hundreds to thousands) epigenetic research can introduce a new understanding of human-environment interaction and facilitate the completion of longitudinal studies facilitating the development of epigenetic-based screening diagnostics crucial to the progression of modern medicine. This epigenetic research may lead to a new understanding of how the environment affects our epigenome and how this relates to a person's health outcome, which may further lead to the development of preventative interventions for individuals who are considered high-risk and diagnostics for these health disparities including, but not limited to, diagnosis.

Some epigenetic studies attempting to quantify environmental and other complex interactions in human populations use blood as the source material for experimentation. Blood can restrict the researcher's ability to conduct large population-sized studies as it:

1. generally requires medical supervision,
2. involves invasive procedures for collection,
3. carries stigma that limits participation,
4. is expensive to collect and transport.

Naturally expressed bodily fluids, e.g., saliva and urine, can be an additional or alternative appropriate source material for home-based sample collection as they:

1. do not require invasive techniques,
2. do not have the same stigma as blood,
3. do not require professional supervision,
4. can be inexpensive to collect.

In addition, at least saliva has been shown to contain white blood cells (Dos-Santos et al., 2009). The use of bodily fluids, e.g., oral fluids, urine, may enable large-scale "population-sized" epigenetic research. In addition, home-base sample collection of oral fluids, or urine, may allow for a much wider range of research options available as it can greatly increase participant numbers and samples can be more easily shipped/transported by the subjects from anywhere in the world. For example, the ability to more easily ship samples from anywhere in the world can be particularly useful when samples are from countries that do not have laboratory infrastructure.

An organism's genome is a fixed sequence that contains its hereditary information and is the same in every cell of an organism. An organism's epigenome, by contrast, varies between cell types and changes over the organism's lifetime. Thus, epigenetic studies may include a single cell type as the source of sample material to control for these differences (Johnson and Tricker, 2010; Lister et al., 2009; and Rangwala et al., 2006). For example, human saliva contains numerous cell types, including epithelial cells, cells normally found in the blood (i.e., T-cells and B-cells), bacteria and debris (Dos-Santos et al., 2009 and Viet and Schmidt, 2008). The cells in saliva that are the most important to profile epigenetically are those that come from the blood stream, as these cells carry epigenetic information from the entire body (Kappeler and Meaney, 2010; McGowen and Szyf, 2010; McGowen and Szyf, 2010; Righini et al, 2007; Rosas et al., 2011, Vlaanderen et al., 2010 and Zhang et al., 2011).

Additionally, it may not be practical to use whole saliva DNA as the cells in saliva that are not found in the blood, such as epithelial cells, which make up the vast majority of cells in saliva (Dos-Santos et al., 2009), have the ability to "mask" the epigenetic effects seen in T-cells (cells that originated in the blood) by dampening the effect of the minority of cells (Dos Santos et al., 2009, Lister et al., 2009; and Tierling et al., 2010). To address these concerns AboGen developed a method to separate and extract the different cell types found in bodily fluids such as saliva, by taking advantage of cell-specific markers and isolation techniques (e.g., magnetic). This method uses practical amounts of bodily fluids, such as saliva, to yield enriched cells that can be used for downstream biological applications including large-scale functional genomic studies (example epigenomic studies). For example, saliva sample processing technology allows collected samples to be processed into single cell types and have their epigenomes profiled.

Furthermore, saliva (and other bodily fluids) can present challenges with cell isolation as a source material for blood cells in respect to downstream experimentation for reasons such as:
1. Blood is a transporter fluid while saliva is a digestive fluid that can be rich in proteases, enzymes and secreted substances and urine is an excretory fluid consisting of unwanted waste products.
2. Cells do not survive intact in saliva for long periods. Whereas cells can survive in blood for weeks (or even years for some cell types), cell survival in saliva is typically less than an hour. It is reported that the percentage of cells in saliva that survive after 15, 45 and 90 minutes is only about 66%, 33% and 27%, respectively. Saliva presents, by its physiological nature, an environment hostile to whole cell preservation for analysis or diagnosis. Some studies demonstrate that 95% of the cells are non-viable by 60 minutes (Baron et al., 1999).
3. Some fluids can have a wide pH range and some of the pH values reported, such as for saliva, would result in death if blood reached that pH (saliva is 6.2-7.4; urine is 4.5-8; blood is 7.35-7.45).
4. Some fluids contain more bacteria than blood.
5. Some fluids contain non-cellular material that varies between individuals and interferes with cell isolation.
6. Some fluids include blood cells, such as T-cells, which can be abundant in blood, but may be rare in other naturally expressed bodily fluids, such as saliva or urine, and further vastly outnumbered by other cell types, such as epithelial cells, unlike in blood.
7. The subset of lymphocyte cells in some bodily fluids, such as saliva, greatly differs from the population of those cell types in blood. For example, only CD4+ CD8− T-cells are reported to be found in saliva.
8. Some fluids are produced each day, such as saliva at about a rate of 0.5-1.5 liters per day per person.

Therefore, there is a need for new methods to isolate rare cells (i.e., T-cells) from saliva, oral fluids, and other naturally expressed bodily fluids.

For collecting saliva samples from a large population of people (example: functional genomic studies, or medical diagnostics) who are widely geographically dispersed, several requirements may need to be met for an optimal sample collection device. For example, it may be beneficial to have the sample collection device securely house a toxic preservative solution in a closed chamber. Additionally, the sample collection device may be able to be sent to a donor with the toxic solution safely enclosed. The sample collection device may also allow easy and safe collection of a donor specimen, such as human saliva or urine, with no risk of exposure of the donor to the toxic solution. Furthermore, the sample collection device may allow the donor to safely mix the toxic solution and the specimen (for preservation of the specimen) with no risk of exposure of the donor to the toxic solution or any other hazard. The sample collection device may also allow the donor to send the sample plus the sample collection device to a laboratory for processing generally "as-is" after securely closing the sample collection device. Finally, the sample collection device may further allow a laboratory technician to receive the sample collection device and safely open it for processing with generally no risk of exposure to any hazards.

Additionally, the purification process requires cells to maintain their antigen profiles and the epigenomic profiling requires that their epigenome be maintained. To this end, it is necessary to treat the cells in such a way that they are able to generally maintain these features. Currently available treatments generally do not meet this need. For example, U.S. Pat. Nos. 7,267,980 and 7,749,757 are understood to disclose solutions containing lysine, glycine and formaldehyde for stabilizing cells from blood. U.S. Pat. No. 6,912,932 is understood to disclose reactants that, when mixed together, generate multiple species of formaldehyde ammonium complexes for stabilizing blood samples containing platelets. However, such solutions address principally the physiologically-friendly environment of blood and fail to address the different nature of saliva. The difficulty of preserving cells and extra-cellular components undamaged in saliva should not be underestimated. The solutions referred to above will not protect cells from the physiologically hostile environment of saliva, and especially will not be able to preserve rare cells, already in relatively sparse quantity in saliva, in sufficient number for saliva to be an effective sample medium for analysis or diagnosis in the manner now proposed. Therefore, there is a need for new solutions and methods that will preserve the antigenicity and epigenome of cells in bodily fluids, such as saliva, oral fluids and other naturally expressed bodily fluids, particularly to enable home-based sample collection.

Personalized medicine is the customization of treatment to an individual as opposed to the one treatment-for-all model. Personalized medicine involves categorizing a patient based on his or her physical condition and designing an optimal healthcare solution exclusively for that category. The progression of personalized medicine is dependent on the discovery, validation, and commercialization of biomarkers to stratify populations for treatment and for the development of diagnostics for screening and early detection.

Epigenetic research has come to the forefront of medical research and is implicated in the etiology of a number of physical and mental illnesses including: cancer, obesity, diabetes, schizophrenia, and Alzheimer's disease. In addition, Epigenetics may hold particular promise in the many scientific and medical areas including but not limited to: cancer, diabetes, drug integrations, drug effectiveness, childhood aggression, suicidal behaviors, aging, inflammation, pain, obesity, schizophrenia, and other mental illnesses.

Similar considerations to those discussed above also apply to extra-cellular components carried in saliva, for example, proteins, viruses, and free-floating DNA/RNA. Such components also degrade rapidly due to the hostile environment of saliva. General blood-based preservative techniques would not in practice be effective for saliva, and for this reason saliva has not hitherto been used as a practical alternative medium for studying such extra-cellular components, and especially not remote home-based sample collection. For example, with current techniques, in order to study the extracellular components of saliva, the saliva must immediately be frozen. If freezing is not immediate, this will cause a change in the concentrations of factors such as cytokines due to the degradation of these factors. Examples of studies of saliva extracellular factors only after freezing include the interleukin family of proteins as well as additional cytokines.

WO 2012/177656 and WO 2015/112496 propose devices, solutions and methods for home-collection and preservation of saliva samples suitable for epigenetic research. The entire contents of these documents is hereby incorporated herein by reference as if reproduced here in full.

SUMMARY OF THE DISCLOSURE

The following presents a simplified summary of the disclosure in order to provide a basic, non-limiting, understanding of some aspects of the disclosure.

Some embodiments of the present disclosure build on the principles in WO 2012/177656 and/or WO 2015/112496.

Some embodiments of the present disclosure are defined in the appended claims.

Some embodiments of the present disclosure provide a solution for preserving cells and/or extra-cellular components in a sample of a naturally expressed bodily fluid, such as oral fluids (e.g., saliva or sputum or fluid of lung aspirates) or urine. Optionally the solution may be defined in combination with a device for collecting the fluid sample from a donor.

As used herein, the term "extra-cellular" may refer to any and/or all components that are not whole cells and not within whole cells. For example, "extra-cellular" may refer to the components remaining were the cells to be removed. Extra cellular components may, for example, include any of: proteins, viruses, free-floating DNA and/or free-floating RNA.

Some embodiments of the present disclosure provide a preservative solution that is (e.g. prior to mixing with the bodily fluid) hypertonic with respect to blood.

While not wishing to be bound to any specific theory, the inventors have appreciated that the tonicity (or osmolality) of saliva may be a significant factor making saliva a hostile environment for cell survival. Saliva, especially saliva collected in donated samples, has been found to be hypotonic with respect to blood (and hence to cells). Cells from blood that pass into a person's saliva are subjected to destructive osmosis that draws fluid into cells, causing the cells to swell, become damaged, and ultimately burst. This may explain the low number of cells reported to survive intact in saliva. In effect, saliva is a natural lysing solution that lyses cells, making saliva a counter intuitive medium for obtaining samples of viable whole cells.

By providing a preservative solution that is hypertonic with respect to blood, the solution can, when mixed with a saliva sample, neutralize the tonicity towards an isotonic environment (with respect to blood and/or cells). Such an environment can avoid, or at least significantly reduce, the osmotic pressure on cells in the collected sample, thereby enabling a significantly improved yield of preserved, intact cells.

It may be noted that a hypertonic, non-lysing preservative solution for preserving cells in e.g. saliva, represents a clear distinction from a preservative solution intended for preserving or stabilizing whole cells in a blood sample. This reflects a significant difference between the tonicity of saliva and blood, even if not acknowledged in prior art teachings focusing on preserving blood. A non-lysing blood preservative should be isotonic so as not to change the neutral, isotonic environment of blood, and avoid increasing the osmotic stress on cells. Were a hypertonic preservative solution to be mixed with blood, this would alter the tonicity of the blood, and risk damage to the cells. Similarly, a conventional isotonic blood preservative used to preserve cells in a saliva sample, would fail to protect the cells adequately against the hypotonic environment of saliva, and produce an inadequate yield of preserved cells, as previously mentioned as a deficiency of prior art teachings.

In some embodiments, the naturally expressed bodily fluid may be of a type that is naturally hypotonic to cells, for example but not limited to oral fluids (e.g. containing saliva), and especially but not limited to saliva itself.

As used herein, a fluid may be regarded as isotonic with respect to blood when the fluid has an osmolality generally in the range of 240-320 milliosmoles per litre (mOsm/L) inclusive. The actual osmolality of blood may be generally in the range of 275-295 mOsm/L inclusive, optionally about 290 mOsm/L. The term "isotonic" as used herein may therefore include a margin in which the difference in osmolality, and hence osmotic pressure, is not significant. A fluid may be regarded as hypotonic with respect to blood when having an osmolality less than 240 mOsm/L. A fluid may be regarded as hypertonic with respect to blood when having an osmolality greater than 320 mOsm/L.

In some embodiments disclosed herein, the osmolality of the solution (e.g. prior to mixing with the bodily fluid) may be defined as being optionally about, or at least, (in either case) "n" times 240 Osm/L, where "n" is a natural number between 2 and 15 inclusive. For example, "n" may be 2, 3, 4, 5, 6, 7, 8, 9, 10, 11, 12, 13, 13, 14 or 15.

In some embodiments disclosed herein, the osmolality of the solution (e.g. prior to mixing with the bodily fluid) may be defined as being optionally about, or at least, (in either case) "n" times 275 Osm/L, where "n" is a natural number between 2 and 15 inclusive. For example, "n" may be 2, 3, 4, 5, 6, 7, 8, 9, 10, 11, 12, 13, 13, 14 or 15.

In some embodiments disclosed herein, the osmolality of the solution (e.g. prior to mixing with the bodily fluid) may be defined as being optionally about, or at least, (in either case) "n" times 290 Osm/L, where "n" is a natural number between 2 and 15 inclusive. For example, "n" may be 2, 3, 4, 5, 6, 7, 8, 9, 10, 11, 12, 13, 13, 14 or 15.

Additionally or alternatively, the aggregate salt-ion osmolality in the solution (e.g. prior to mixing with the bodily fluid) may optionally be about, or at least, (in either case) "n" times 290 mOsm/L, where "n" is a natural number between 2 and 15 inclusive. For example, "n" may be 2, 3, 4, 5, 6, 7, 8, 9, 10, 11, 12, 13, 14 or 15.

In some embodiments disclosed herein, the osmolality of the solution (e.g. prior to mixing with the bodily fluid) relative to that of blood may be defined as being optionally about, or at least, (in either case) "n" times that of blood, where "n" is a natural number between 2 and 15 inclusive. For example, "n" may be 2, 3, 4, 5, 6, 7, 8, 9, 10, 11, 12, 13, 14 or 15.

Additionally or alternatively, the concentration of sodium chloride (NaCl) in the solution (e.g. prior to mixing with the bodily fluid) may optionally be about, or at least, (in either case) "n" times a concentration "m", where: "m" is a value in a range between 8.0 and 9.0 grams per liter (g/L) inclusive; and where "n" is a natural number between 2 and 15 inclusive. For example, "n" may be 2, 3, 4, 5, 6, 7, 8, 9, 10, 11, 12, 13, 14 or 15.

Additionally or alternatively, the solution may comprise phosphate-buffered-saline (PBS) in a concentration (e.g. prior to mixing with the bodily fluid) that is optionally about, or at least, (in either case) "n" times a blood-isotonic PBS concentration, where "n" is a natural number between 2 and 15 inclusive. For example, "n" may be 2, 3, 4, 5, 6, 7, 8, 9, 10, 11, 12, 13, 14 or 15.

In some embodiments, a technique for measuring the tonicity/osmolality of a fluid is to measure its electrical conductivity. Conductivity is indicative of ion presence, which may be associated with osmolality. In some embodiments, the solution has a conductivity of at least 15 milli-Siemens/centimeter (mS/cm), optionally about, or at least, (in either case) a value selected from the group: 15.5 mS/cm, 16 mS/cm, 16.5 mS/cm, 17 mS/cm, 17.5 mS/cm, 18 mS/cm, 18.5 mS/cm.

The electrical conductivity may be defined on its own, or optionally in combination with one or more other empirical parameters for qualifying characteristics of the solution, for example, one or both of:
  (i) pH—for example, a value in the range of about 6.4 to about 8.4 inclusive, and in some embodiments, between about 7.2 to about 7.6 inclusive, optionally between about 7.3 and 7.6 inclusive; and/or
  (ii) Density—for example, a value in the range of 1 to 1.015 Kg/liter inclusive, and in some embodiments from 1.0090 to 1.0112 kg/liter inclusive.

In some embodiments, the solution (prior to mixing with a sample of a hypotonic naturally expressed bodily fluid) has a hypertonicity such that, upon mixing with a collected sample of the bodily fluid, the mixture of the solution and bodily fluid together is isotonic, wherein the tonicity is defined with respect to blood.

In some embodiments, the solution (prior to mixing with a saliva sample), has a tonicity such that, upon mixing with a collected saliva sample, the mixture of solution and saliva together is isotonic, wherein the tonicity is defined with respect to blood.

Obtaining an isotonic solution may be advantageous not just during preservation (e.g. fixation) of the saliva sample, but also during a period in which the preserved cells are stored awaiting processing or analysis. For example, preserved and/or fixed cells may still be vulnerable to osmotic pressure effects that can cause the cells to swell and burst and/or collapse and implode depending on the osmotic conditions affecting fluid transfer through the cell wall.

Additionally or alternatively to any of the above, in some embodiments, the solution is able to preserve cells and/or extra-cellular components in a naturally expressed bodily fluid sample (for example, saliva, sputum, fluid of lung aspirates or urine), at least to a predetermined efficacy, for a period of at least one week, optionally at least two weeks, optionally at least three weeks, optionally at least a month, optionally at least two months, optionally at least three months.

For purposes of the disclosure, "preserving" means, e.g., preventing the cells from having their antigens degraded, such that they can be purified or enriched based on their antigens, and preventing alterations in the cellular epigenome. The "epigenome" means the state or pattern of alteration of genomic DNA by covalent modification of the DNA or of proteins bound to the DNA. Examples of such alterations include methylation at the 5 position of cytosine in a CpG dinucleotide, acetylation of lysine residues of histones, and other heritable or non-heritable changes that do not result from changes in the underlying DNA sequence As used herein the term "efficacy" may mean that at least a predetermined percentage of the cells in the original bodily fluid sample are preserved. The predetermined percentage may optionally be at least 50%, at least 55%, at least 60%, at least 65%, at least 70%, optionally at least 75%, optionally at least 80%, optionally at least 85%, optionally at least 90%, optionally at least 95%. (The cell concentration per unit volume may be reduced compared to the original body fluid sample, because the mixing of the original sample with the preservation solution increases the net volume of the mixture, thereby diluting the cell concentration.)

Additionally or alternatively, the efficacy may refer to the number of cells (e.g. of a certain type, e.g. T-cells) per unit volume. For example, the number of (e.g. such) cells may be at least about 5000 per ml, optionally at least about 10000 per ml, optionally at least about 12000 per ml.

Additionally or alternatively, in some embodiments, the solution may have a shelf life at room temperature of at least 1 month, optionally at least two months, optionally at least three months, optionally at least four months.

Additionally or alternatively, in some embodiments, a solution for preserving cells and/or extra cellular components (e.g. any of: proteins, viruses, free-floating DNA and/or free-floating RNA) in bodily fluids, such as oral fluids (e.g. saliva and/or sputum) and urine, is provided for further separation into cell types and extra cellular components, and for downstream analysis. Optionally, for cells, the solution may allow for the cells in saliva to retain their antigenicity and cellular architecture during storage. Additionally or alternatively, optionally for extra-cellular components, the solution may allow for extra-cellular components (for example, proteins) to be preserved against degradation, and/or without preserving bioactivity of an extra-cellular protein. In some embodiments, the solution may preserve both cells, and extra-cellular components in a saliva sample.

The solution can contain at least one chemical fixing agent, such as but not limited to paraformaldehyde, and at least one protease inhibitor. In some embodiments, the solution may further contain, for example, one or more of: at least one antimicrobial agent, serum proteins from human and/or other animal species. Additionally or alternatively, the solution may be buffered at a pH between about 6.4 to about 8.4, and in some embodiments, between about 7.2 to about 7.6.

Chemical fixing of the cells by the preservative can increase the mechanical strength of the cells, enabling the cells to be preserved intact and better to withstand, with time, natural degradation and osmotic pressure. In particular, storing the cells in fixative for more than a few minutes (so called "over-fixing") is reported to increase cell resistance to lysis.

Chemical fixing of extra-cellular components, such as proteins can bind the proteins by cross-linking them with other material, for example, other proteins or DNA. For example, proteins that were biologically bound to other material may be bound more firmly chemically with the same material by the cross-linking. Proteins that were merely in proximity with other material may be bound to that material by cross-linking. The cross-linking may preserve the protein by reinforcing the protein against undesired disintegration into smaller segments (peptides for example).

The cross-linking may be at least partly reversible. Reversing the cross-linking may, for example, be a step in later downstream processing, for example, for the analysis of extra-cellular components such as proteins.

Additionally or alternatively to any of the above, in some embodiments, the solution is substantially free of detergent. Detergents are sometimes used in some processing of biological samples to facilitate penetration through cellular material but, it is believed herein, at the cost of increased cell damage and cell loss. According to some embodiments of the disclosure, avoiding the presence of detergent can enhance the number of preserved cells, which may be especially advantageous bearing in mind the relatively sparse quantity in a saliva sample of certain cells of interest.

As mentioned previously, the solution may optionally be hypertonic with respect to blood.

Additionally or alternatively to any of the above, in some embodiments, a sample collection device is provided containing a preserved sample of a naturally expressed bodily fluid (for example, saliva, sputum or other oral fluid, or urine), the preserved sample being isotonic with respect to blood. Optionally, the preserved sample may be a mixture of (i) a collected sample of the naturally expressed bodily fluid; and (ii) a preservative solution.

Additionally or alternatively to any of the above, some embodiments of the present disclosure provide use of a hypertonic preservation solution for mixing with a sample of a hypotonic naturally expressed bodily fluid, to bring the tonicity of the resulting mixture towards being isotonic, wherein the tonicity is defined relative to blood. Merely as an example, the bodily fluid may be or contain saliva.

In some embodiments, a method for preserving cells in one or more bodily fluids includes contacting collected cells with a solution according to one and/or another embodiment of the present disclosure, which allows the cells to retain their antigenicity and epigenome, for example.

In some embodiments, a method for preserving extra-cellular components in one or more bodily fluids includes contacting a collected sample of bodily fluid with a solution according to one and/or another embodiment of the present disclosure, which allows certain extra-cellular components, for example proteins, to retain their structure, optionally without retaining bioreactivity.

The bodily fluid(s) may naturally expressed, for example comprising one or more of: oral fluid; saliva; sputum; fluid(s) of lung aspirates; urine. In some cases, lung aspirates may also be artificially aspirated or prompted.

In some embodiments, a method for separating certain extra-cellular components (e.g. any of: proteins, viruses, free-floating DNA and/or free-floating RNA) from cells in a chemically fixed bodily fluid (for example, saliva or another oral fluid, or urine), includes centrifuging the sample to cause the sample to separate out into said certain extra-cellular components in liquid form, and a pellet of, for example, cells. The pellet and the liquid components may be treated separately. For example, the liquid components may be processed for analysis of the certain extra-cellular components. Additionally or alternatively, the pellet may be processed for cell analysis. Optionally, the same sample may be provide material for analysis of both (i) cells, and (ii) said extra-cellular components (e.g. any of: proteins, viruses, free-floating DNA and/or free-floating RNA).

In some embodiments, a method for isolating cells from chemically fixed cells collected from a bodily fluid, e.g., saliva or urine, and includes centrifuging the cells to separate, for example, DNA and/or other soluble material from a pellet of cells, bacteria, and debris, enriching white blood cells from other contents of the pellet, and isolating specific cells (e.g., white blood cells) using antibodies conjugated to magnetic beads targeted to cell specific markers.

In some embodiments, methods for isolating a particular type of cell, for example, a type of white blood cell (e.g., lymphocytes), from one or more bodily fluids (e.g., saliva and/or urine), and includes one or more of the following steps (and, depending upon the embodiment, several or all of the following steps): providing a sample of bodily fluid comprising chemically fixed cells, optionally centrifuging the bodily fluid sample to obtain a pellet comprising cells, optionally re-suspending the pellet in a buffer, subjecting the re-suspended pellet to density gradient separation to obtain a layer of a mixture of white blood cell types (including lymphocytes), contacting the mixture of cell types with a solution containing specific binding agents for an epitope found on a particular type of white blood cell, and separating the particular type of white blood cell (including lymphocytes) from the mixture of white blood cell types.

In some embodiments, the specific binding agents may be magnetic beads coupled to antibodies specific to an epitope found on a particular type of white blood cell, and in the separation step may then comprise, for example, magnetically separating the particular type of white blood cell (including lymphocytes) from the mixture of white blood cell types (though other cell separation techniques are within the scope of the disclosure).

In some embodiments, the bodily fluid (e.g., saliva, sputum (or other oral fluid), or urine) can be mixed with a chemical fixative solution and the mixture can be removed from the pellet. The pellet can then be re-suspended in a buffer. The re-suspended pellet may optionally be centrifuged and washed one or more times in the buffer. The washed pellet may then be applied to a hydrophilic polysaccharide mixture to form a gradient. This gradient may be different than that used for blood because the density of the cells in other bodily fluids (e.g., saliva, urine) after chemical fixation for preservation can be different, due to the different density of the preserved cells requiring an alteration in the time, temperature, and/or density of the gradient for the cells to be processed through this density gradient.

Additionally, in some embodiments, the white blood cells can form a layer in the gradient. The white blood cell layer can be extracted from the gradient and placed in another centrifuge tube where it may be washed in a buffer and re-pelleted to remove the remaining gradient mixture. The pellet may then be re-suspended and incubated in a buffer containing antibodies that are conjugated to magnetic beads and specific to antigens that are specific for a cell type to be isolated. In some embodiments, the cell type to be isolated is T-cells and the antigen is a T-cell-specific antigen. In some embodiments, the antigen is CD4. The re-suspended cells in the buffer can be bound by the antibody and subjected to a magnetic field that magnetically attracts the cells bound to the antibody-conjugated magnetic beads to the side of the tube. The remaining liquid may then be removed from the tube and the tube is washed in buffer. Isolated T-cells then remain attracted to the side of the tube and are ready for further processing, such as freezing for later downstream experimentation (for example).

In some embodiments, a method for preserving cells and/or extra-cellular components in a naturally expressed bodily fluid comprises contacting the bodily fluid with the preservation solution according to any of the disclosed embodiments.

The ability to obtain a sample of a naturally expressed bodily fluid, preserved to provide a usable yield of (i) rare or sparsely numbered cells, and/or (ii) extra-cellular components (e.g. any of: proteins, viruses, free-floating DNA and/or free-floating RNA) may provide an alternative technique to blood sampling, for (i) diagnosis of a patient's medical condition, and/or (ii) monitoring the effect of treatment. When used as a diagnostic tool for diagnosing a medical condition to be treated, the process/product may sometimes be referred to herein as a "companion diagnostic". For example, MGMT saliva-based assays measuring MGMT promoter methylation may be used as a companion diagnostic. When used as a monitoring tool for monitoring the effect of treatment (e.g. whether a certain treatment is working, or whether an increase or decrease in dosage is effective, or whether the treatment will work at all), the process/product may sometimes be referred to herein as a "companion validator".

Such techniques may further facilitate the ease of obtaining samples from patients or study subjects, and enable home-collection of samples, which in turn may vastly expand the number of patients or study subjects able to participate in a study, diagnosis or monitoring program.

Techniques used for identifying specific cell types or other biomarkers in blood samples, may also be used (either with or without modification) for identifying such cells or other biomarkers in the naturally expressed bodily fluid.

By way of example, cells or extra-cellular material may be analyzed to indicate or identify one or more of:
(a) Cells with markers (cellular or molecular) that identify regression or aggression of disease. The disease may, for example, be cancer (optionally, but not limited to leukemia). In the case of the fluid being or containing sputum, the disease may be any one or more of: lung cancer, lung carcinoma, non-small cell lung carcinoma (NSCLC), pneumonia, or tuberculosis.
(b) Prenatal cells.
(c) Circulating tumor cells (e.g. metastatic or otherwise).
(d) Rare forms of normal cells, for example, any one or more of:
Premature cells as in myelodysplastic syndrome;
Epithelial cell sub-types indicating disease and not originating from the mouth;
Langerhands cells, for example (but not limited to) diagnosis blood disorders.
(e) one or more biomarkers indicative of obesity.
(f) one or more biomarkers indicative of bacterial infection version viral infection (useful to avoid unnecessary and inappropriate prescription of antibiotics).
(g) one or more biomarkers indicative of autism.
(h) one or more biomarkers indicative of Alzheimer disease.
(i) one or more biomarkers indicative of hetotological disorders.
(i) one or more biomarkers indicative of cardiovascular diseases or disorders.
(k) one or more biomarkers indicative of diabetes
(l) one or more biomarkers indicative of vulnerable clack, for example, relating to immune cell activity and/or immune cell biomarkers.
(m) one or more biomarkers, and/or one or more released factors, indicative of a dormant and/or latent and/or stealth form of a disease or infection. For example, such a disease may be LTBI. Additionally or alternatively, such factors may be peptides and/or cytokines.
(n) Presence of HIV infection in cells, optionally by detecting intracellular HIV virus.
(o) one or more biomarkers indicative of cancer.
(p) one or more biomarkers indicative of chronic obstructive pulmonary disease (COPD).
(q) one or more biomarkers indicative of drug resistant Tuberculosis.
(r) one or more biomarkers suitable for replicating and/or substituting one or more tests from the following categories of blood tests: electrolyte levels; lipid profile tests; vitamin levels, Hepatitis tests; iron deficiency tests; liver function tests; renal profile tests; diabetic screening tests; hemogram tests; thyroid profile tests.
(s) one or more biomarkers indicative of a type of COPD being "asthma COPD overlap syndrome" (ACOS). Optionally, such biomarkers can provide a companion diagnostic to a general diagnosis of COPD, for detecting that the COPD is ACOS. Additionally or alternatively, such biomarkers can provide a companion validator to monitor efficacy of treatment targeting ACOS. Additionally or alternatively, a general diagnosis of COPD may, for example, be performed using the biomarkers referred to in (p) above, and/or the general diagnosis of COPD may be performed using other conventional diagnostic tests.

In some embodiments, techniques used to diagnose a medical condition of a patient, optionally but not exclusively limited to, diagnosis of rare cells in a naturally expressed bodily fluid (e.g. saliva, sputum, urine) may include one or more of:
(a) Flow cytometry;
(b) Fluoresence-activated cell sorting (FACS);
(c) Immunohystochemistry;
(d) Molecular analysis (for example, but not limited to any of: epigenetic; genetic; translational; post-translational);
(e) Cytology.
(f) Protein level (post transcriptional) analysis techniques.
(g) RNA level (transcriptional) analysis to measure gene expression.
(h) DNA, e.g. epigenetic, and/or including DNA methylation and histone modifications.

It is worth noting that while some embodiments of the sample collection devices disclosed herein are set forth for use with the collection of bodily fluids, the same also has particular use with the collection of any other substance, including hazardous and/or toxic fluids.

Although some of the embodiments relate to using a preservative for preserving whole cells and/or extra-cellular material, other embodiments may relate to extracting and preserving nucleic acids in a collected sample. The nucleic acids may be DNA and/or RNA.

For example, a solution may be used that lyses cells in a collected sample to extract nucleic acids, and that preserves the nucleic acids.

By way of example only, reference is made to Annex 1 appended to the present description, the entire content of which is incorporated herein as part of the present disclosure.

Without limiting the present disclosure, an numbered, itemized list of certain features and/or aspects disclosed herein now follows:
Itemization Number:
1. A solution for preserving cells and/extra-cellular components in naturally expressed bodily fluid for further downstream analysis and/or for diagnosis of a medical condition, the solution being hypertonic with respect to blood.

2. The solution of item 1, wherein the naturally expressed bodily fluid comprises one or more selected from the group of: oral fluids; saliva; sputum; urine; fluid of lung aspirates.
3. The solution of item 1 or 2, wherein the naturally expressed bodily fluid is naturally hypotonic.
4. The solution of item 1, 2 or 3, wherein the osmolality of the solution is about, or at least, "n" times 240 mOsm/L, where "n" is a natural number between 2 and 15 inclusive.
5. The solution of item 1, 2, 3 or 4, wherein the osmolality of the solution is about, or at least, "n" times 275 mOsm/L, where "n" is a natural number between 2 and 15 inclusive.
6. The solution of item 1, 2, 3, 4 or 5, wherein the osmolality of the solution is about, or at least, "n" times 290 mOsm/L, where "n" is a natural number between 2 and 15 inclusive.
7. The solution of any preceding item, wherein the tonicity of the solution relative to that of blood is about, or at least, "n" times that of blood, where "n" is a natural number between 2 and inclusive.
8. The solution of any preceding item, wherein the aggregate salt-ion osmolarity in the solution is about, or at least, "n" times 290 mOsm/L, where "n" is a natural number between 2 and 15 inclusive.
9. The solution of any preceding item, wherein the concentration of sodium chloride (NaCl) in the solution is about, or at least, "n" times a concentration "m", where: "m" is a value in a range between 8.0 and 9.0 grams per liter (g/L) inclusive; and where "n" is a natural number between 2 and 15 inclusive.
10. The solution of any preceding item, wherein the solution comprises phosphate-buffered-saline (PBS) in a concentration that is about, or at least, "n" times a blood-isotonic PBS concentration, where "n" is a natural number between 2 and 15 inclusive.
11. The solution of any preceding item, wherein the solution has a hypertonicity such that, upon mixing with a collected sample of the bodily fluid, the mixture of the solution and bodily fluid together is generally isotonic, wherein the tonicity is defined with respect to blood.
12. The solution of any preceding item, wherein the solution has an electrical conductivity of at least 15 mS/cm.
13. The solution of item 12, wherein the solution has at least one of the following further parameters:
(i) a pH value in the range of 6.4 to about 8.4 inclusive, and/or
(ii) a density in the range of 1 to 1.015 kg/liter inclusive.
14. The solution of any preceding item, wherein the solution is effective to preserve cells for a duration selected from: at least two weeks; or at least three weeks, or at least a month, or at least two months; or at least three months.
15. The solution of any preceding item, wherein the solution is effective to preserve cells when kept at a temperature selected as at least one of the following temperatures or temperature ranges: between 4° C. and 40° C.; between 4° C. and 30° C.; about room temperature; about 4° C.; about 30° C.; about 40° C.
16. The solution of any preceding item, wherein the solution has a shelf-life selected from at least one of the following: at least 1 month; at least two months; at least three months; at least four months.
17. The solution of item 11, wherein the shelf-life is shelf-life at room temperature.
18. The solution of any preceding item, wherein the solution is effective to preserve at least a predetermined percentage of cells from an original sample of the body fluid, the predetermined percentage being selected from: at least 50%, at least 55%, at least 60%, at least 65%, at least 70%, at least 75%, at least 80%, at least 85%, at least 90%, at least 95%.
19. The solution of any preceding item, wherein a number of preserved cells or a predetermined type, per ml is at least about 5000, or at least about 10000, or at least about 12000.
20. The solution of any preceding item, wherein the cells are T-cells.
21. The solution of any preceding item, wherein the solution comprises at least one chemical fixing agent and at least one protease inhibitor, buffered at a pH from about 6.4 to about 8.4.
22. A solution, optionally according to any preceding item, for preserving at least extra-cellular components in a naturally expressed bodily fluid for further downstream analysis and/or for diagnosis of a medical condition, wherein the solution comprises at least one chemical fixing agent, and optionally buffered at a pH from about 6.4 to about 8.4.
23. The solution according to item 21 or 22, wherein the chemical fixing agent is selected from the group consisting of aldehydes.
24. The solution according to item 23, wherein the chemical fixing agent is paraformaldehyde.
25. The solution according to item 21, 22, 23 or 24, wherein the chemical fixing agent is present at a concentration of about 1% (v/v).
26. The solution according to any of items 21 to 25, further comprising one or more of at least one antimicrobial agent and serum proteins from human and/or other animal species.
27. The solution according to item 26, wherein the antimicrobial agent is selected from the group consisting of antibacterial and antifungal antibiotics.
28. The solution according to any of items 21 to 27, wherein the or a protease inhibitor is selected from the group consisting of: Aspartic protease inhibitors, Cysteine protease inhibitors, Metallo protease inhibitors, Serine protease inhibitors, Threonine protease inhibitors, Trypsin inhibitors, Kunitz STI protease inhibitor and a combination of any of the foregoing.
29. The solution according to any of items 21 to 28, wherein the or a protease inhibitor is selected from the group consisting of: sodium azide, PMSF, aprotinin, leupeptin, pepstatin, natural or synthetic protease inhibitors, mixtures of protease inhibitors both natural and synthetic, and any combination of the foregoing.
30. The solution according to any of items 21 to 29, wherein the or a protease inhibitor is sodium azide.
31. The solution according to any preceding item, wherein the solution is buffered at a pH of from about 7.2 to about 7.6.
32. The solution according to any of items 21 to 31, wherein the buffer is selected from the group consisting of: barbital, trisphosphate, citrate, cacodylate, other non-phosphate buffers and any combination of the foregoing.
33. The solution according to any of items 21 to 31, wherein the buffer is a phosphate buffer.

34. A method for preserving cells and/or extra cellular components in a naturally expressed bodily fluid comprising contacting the bodily fluid with the preservation solution according to any preceding item.

35. A method for preserving cells and/or extra cellular components in a hypotonic naturally expressed bodily fluid, comprising contacting the bodily fluid with a hypertonic preservation solution, wherein the tonicity is defined relative to blood.

36. A sample collection device for collection of a naturally expressed bodily fluid, the sample collection device containing a preservation solution according to any of items 1 to 33.

37. A sample collection kit including a solution as defined in any of items 1 to 33.

38. A fluid sample for downstream analysis of cells and/or extra cellular components in the fluid sample, the fluid sample comprising a naturally expressed hypotonic bodily fluid mixed with a preservation solution, wherein the sample fluid is generally isotonic, and wherein tonicity is defined with respect to blood.

39. The fluid sample of item 38, wherein the naturally expressed bodily fluid is saliva.

40. A sample collection device containing a sample fluid as defined in item 38 or 39.

41. A method of diagnosing and/or monitoring a medical condition, comprising:
  obtaining a sample of a naturally expressed bodily fluid;
  contacting the sample with a preservative solution for stabilizing cells and/or extra-cellular components in the sample; and
  analyzing stabilized cells and/or extra-cellular components from the sample to identify, diagnose or monitor the medical condition.

42. The method of item 41, wherein the naturally expressed bodily fluid is one or more selected from: an oral fluid; saliva; sputum; urine; fluid of lung aspirates.

43. The method of item 41 or 42, wherein the naturally expressed bodily fluid is *salvia*.

44. The method of item 41, 42 or 43, further comprising the step of contacting the sample with a pre-treatment agent prior to the step of contacting the sample with the preservative solution, the pre-treatment agent configured to stimulate release of one or more factors indicative of a medical condition.

45. The method of item 44, wherein the pre-treatment agent comprises one or more antigens associated with the medical condition.

46. The method of any of items 41 to 45, wherein the method further comprises the step of separating at least certain cells from at least certain extra-cellular components.

47. The method of item 46, wherein the at least certain extra-cellular components include one or more selected from: proteins, viruses, free-floating DNA and/or free-floating RNA.

48. The method of any of items 41 to 47, further comprising a step of enriching the stabilized cells prior to the step of analysis.

49. The method of any of items 41 to 48, further comprising a step of isolating one or more cell types from the stabilized cells prior to the step of analysis.

50. The method of any of items 41 to 49, wherein the step of analyzing comprises identifying cells and/or extracellular components with cellular markers or molecular markers that identify regression or aggression of disease.

51. The method of item 50, wherein the disease is one or more selected from the group consisting of: cancer; leukemia; lung cancer; pneumonia; and/or tuberculosis.

52. The method of any of items 41 to 51, wherein the step of analyzing comprises identifying circulating tumor cells.

53. The method of any of items 41 to 52, wherein the step of analyzing comprises identifying prenatal cells.

54. The method of any of items 41 to 53, wherein the step of analyzing comprises identifying rare forms of normal cells.

55. The method of item 54, wherein the rare form of normal cells comprises one or more selected from the group of: premature cells; premature cells indicative of myelodysplastic syndrome; epithelial cell sub-types indicating disease and not originating from the mouth; and/or Langerhands cells.

56. The method of any of items 41 to 55, wherein the step of analyzing comprises flow cytometry.

57. The method of any of items 41 to 56, wherein the step of analyzing comprises fluorescence-activated cell sorting (FACS).

58. The method of any of items 41 to 57, wherein the step of analyzing comprises immunohystochemistry.

59. The method of any of items 41 to 58, wherein the step of analyzing comprises molecular analysis.

60. The method of item 59, wherein the molecular analysis comprises any one or more selected from the group consisting of: epigenetic analysis; genetic analysis; translational analysis; and/or post-translational analysis.

61. The method of any of items 41 to 60, wherein the step of analyzing comprises cytology.

62. The method of any of items 41 to 61, wherein the step of analyzing comprises identifying a biomarker indicative of obesity.

63. The method of any of items 41 to 62, wherein the step of analyzing comprises identifying a biomarker indicative of a bacterial infection.

64. The method of any of items 41 to 63, wherein the step of analyzing comprises identifying a biomarker indicative of a viral infection.

65. The method of any of items 41 to 64, wherein the step of analyzing comprises identifying a biomarker indicative of autism.

66. The method of any of items 41 to 65, wherein the step of analyzing comprises identifying a biomarker indicative of Alzheimer disease.

67. The method of any of items 41 to 66, wherein the step of analyzing comprises identifying a biomarker indicative of a Hetotological disorder.

68. The method of any of items 41 to 67, wherein the step of analyzing comprises identifying a biomarker indicative of a cardiovascular disease or disorder.

69. The method of any of items 41 to 68, wherein the step of analyzing comprises identifying a biomarker indicative of diabetes.

70. The method of any of items 41 to 69, wherein the step of analyzing comprises identifying a biomarker indicative of vulnerable plack.

71. The method of any of items 41 to 70, wherein the step of analyzing comprises identifying a biomarker indicative of latent tuberculosis infection.

72. The method of any of items 41 to 70, wherein the step of analyzing comprises identifying a factor released by treatment of the sample with an antigen prior to the step of contacting with the preservation solution.
73. The method of item 72, wherein the antigen comprises a peptide of *M. tuberculosis*, and the factor comprises interferon gamma.
74. The method of any of items 41 to 73, wherein the step of analyzing comprises identifying a biomarker indicative of HIV infection.
75. The method of any of items 41 to 74, wherein the step of analyzing comprises identifying HIV virus infection prior to the presence of detectable antibodies in the sample.
76. The method of any of items 41 to 75, wherein the step of analyzing comprises identifying intracellular HIV virus in the sample.
77. The method of any of items 41 to 76, wherein the step of analyzing comprises identifying HIV virus within a t-cell, optionally a CD4+ t-cell.
78. The method of any of items 41 to 77, wherein the step of analyzing comprises assessing the quantity of CD4+ t-cells, for identifying an immune deficiency, optionally indicative of HIV infection and/or AIDS.
79. The method of any of items 41 to 78, wherein the step of analyzing comprises identifying a biomarker: (i) indicative of COPD; and/or (ii) indicative of ACOS; and/or (iii) for distinguishing between ACOS and non-ACOS types of COPD.
80. A method of diagnosing HIV infection, comprising:
providing a preserved sample of a naturally expressed bodily fluid from an individual, optionally saliva; and
identifying intracellular HIV virus in the sample to diagnose HIV infection in the individual.
81. The method of item 80, wherein the step of identifying intracellular HIV virus comprises identifying HIV virus within a t-cell of the sample, optionally a CD4+ t-cell.
82. The method of item 81, wherein the step of providing comprises providing a fixed sample of the naturally expressed bodily fluid.

BRIEF DESCRIPTION OF THE DRAWINGS

Non-limiting embodiments are described below, by way of example only, with reference to the accompanying drawings, in which:—

FIG. 2 shows the time course of DNA yield in samples stored in chemical fixative solution at room temperature after 0, 1, 2 and 7 days, as well as DNA extracted from T-cells from each sample according to some embodiments.

FIG. 3 is a graph demonstrating the preservation of cells in a saliva sample contacted by a preservation solution.

FIG. 7 shows a saliva dose curve of micrograms of isolated T-cell DNA per ml of saliva according to some embodiments.

FIG. 8 is a schematic graph illustrating a variation in sample concentration, per unit volume, in dependence on volume of a preservative composition that is added (Annex 1).

The devices, solutions and methods of sample collection, preservation, isolation and analysis will be better understood in light of the following drawings, detailed description and claims. Like reference symbols in the various drawings indicate like elements.

DETAILED DESCRIPTION OF EMBODIMENTS

Reference is made to the disclosure of WO 2012/177656 and/or WO 2015/112496 on which the present disclosure may build in some embodiments.

In some embodiments, a solution is disclosed for preserving cells and/or extra-cellular components (e.g. any of: proteins, viruses, free-floating DNA and/or free-floating RNA) in one or more naturally expressed bodily fluids, such as saliva, sputum, fluid of lung aspirates, oral fluids, and/or urine. The solution may be beneficial for further separation into cell types and/or extra-cellular components, and downstream analysis that allows for storage of cells and/or extra cellular components in the body fluid. Cells may be preserved to retain their antigenicity and cellular architecture. Extra-cellular components may be preserved to avoid degradation and disintegration. Proteins may be preserved but without preserving their bioreactivity.

In some embodiments, the solution is disclosed in combination with a sample collection device, optionally suitable for home use, or at least without the need to visit a medical laboratory. In some embodiments, the solution is referred to in an "as supplied" state prior to mixing with a collected bodily fluid sample. In some embodiments, the solution is referred to in its state after mixing with a collected bodily fluid sample.

Figure 1:
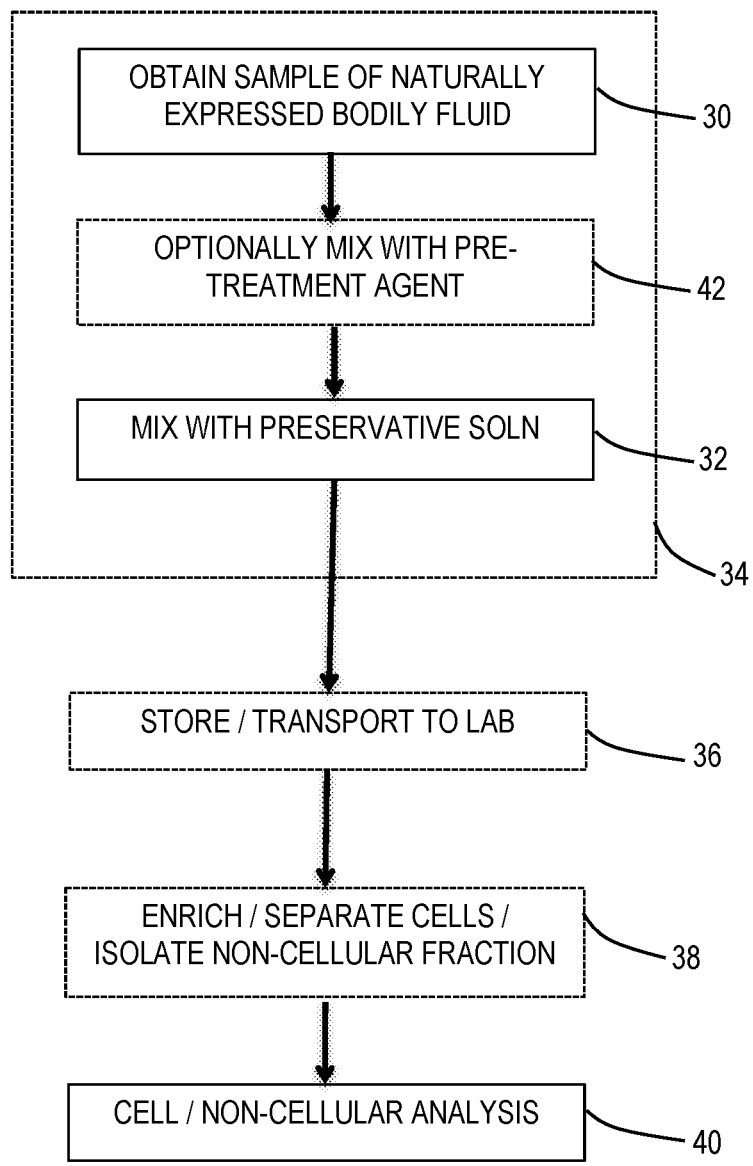
FIG. 1 is a schematic flow diagram illustrating steps for the collection and processing of a sample of a naturally expressed bodily fluid.

Referring to FIG. 1, a technique for collecting and processing a naturally expressed bodily fluid is illustrated. The process will be described in terms of an oral fluid containing saliva, as a most difficult example. However, it will be appreciated that the same principles may be applied to the collection and processing of other naturally expressed bodily fluids. References to saliva may be replaced by any other of such naturally expressed bodily fluids, in particular, oral fluids in general, and/or sputum, and/or fluid of lung aspirates, and/or urine.

Referring to FIG. 1, a first step 30 may be for a donor to donate a sample of fluid, for example, saliva. The donation may be effected by spitting into a collection device, or by collecting saliva by any other technique, such as by using a swab stick.

A second step 32 may be to contact and/or mix the collected saliva sample with a preservative solution for preserving whole cells in the collected saliva sample and/or for preserving extra-cellular components in the collected saliva sample. The solution for preserving cells and/or extra-cellular components may be beneficial for further separation into cell types and/or extra-cellular components, and downstream analysis. As discussed hereinbefore, saliva presents a physiologically hostile environment for cells of interest and for extra-cellular components. Cells of interest may begin to be damaged and destroyed within minutes of the sample being collected. In some embodiments, step 32 may be carried out relatively soon after step 30 in order to avoid or reduce the detrimental effect of saliva on the yield of intact cells and preserved extra-cellular components in the collected sample.

As used herein, "preserving cells" means preventing the cells from having their antigens degraded, such that they can be purified or enriched based on their antigens, and preventing alterations in the cellular epigenome. The "epigenome" means the state or pattern of alteration of genomic DNA by covalent modification of the DNA or of proteins bound to the DNA. Examples of such alteration include methylation at the 5 position of cytosine in a CpG dinucleotide, acetylation of lysine residues of histones, and other heritable or non-heritable changes that do not result from changes in the underlying DNA sequence. Additionally or alternatively, "preserving cells" may mean that the cells in saliva retain their antigenicity and cellular architecture during storage.

As used herein the term "efficacy" of preservation may mean that at least a predetermined percentage of the cells in the original bodily fluid sample are preserved. The predetermined percentage may optionally be at least 50%, at least 55%, at least 60%, at least 65%, at least 70%, optionally at least 75%, optionally at least 80%, optionally at least 85%, optionally at least 90%, optionally at least 95%. (The cell concentration per unit volume may be reduced compared to the original body fluid sample, because the mixing of the original sample with the preservation solution increases the net volume of the mixture, thereby diluting the cell concentration.)

Additionally or alternatively, the efficacy may refer to the number of cells (e.g. of a certain type, e.g. T-cells) per unit volume. For example, the number of (e.g. such) cells may be at least about 5000 per ml, optionally at least about 10000 per ml, optionally at least about 12000 per ml.

Additionally or alternatively, preserving extra-cellular components such as proteins means preventing the proteins from disintegrating or being cut into smaller pieces (peptides for example). Preserving proteins may also involve immobilizing the proteins, by binding them to whatever material the protein may have been biologically bound to prior to preservation, and/or to other material in close proximity that they bind to post preservation. The bioreactivity of the protein may be neutralized, to enable the protein to be analyzed in later downstream steps, for example, by mass spectroscopy.

In some embodiments, prior to the second step 32, an optional pre-treatment step 42 may be carried out, to mix the saliva with a pre-treatment agent, for example, a solution, powder or solid agent. The pre-treatment may in some embodiments be biological or non-biological, or a mixture of biological and non-biological agents. The pre-treatment agent may in some embodiments be used to react with, and/or stimulate release of, and/or otherwise cause production of a certain factor or factors in the saliva. Additionally or alternatively, the pre-treatment agent may stimulate a bio-reactive response of the saliva.

Such a bio-reactive response might be less effective (or might not be effective at all) after the saliva has been preserved, e.g. by fixation.

One example of a pre-treatment agent may be antigens for stimulating or provoking release of certain factors from such cells as lymphocytes to determine if the saliva is from an individual infected with an associated disease and/or infection. For example, the pre-treatment agent may comprise peptides. In one specific example used in the detection of latent tuberculosis infection (LTBI) described later, the peptides may be peptides from *M. tuberculosis*, that are recognized by lymphocytes, and stimulate a bio-response in the form of release of factors such as interferon gamma if the saliva is from a person infected with LTBI. The pre-treatment agent may optionally comprise more than one antigen and/or more than one peptide.

Some embodiments of the present disclosure provide such a preservative solution that is (e.g. prior to mixing with the bodily fluid) hypertonic with respect to blood.

While not wishing to be bound to any specific theory, as explained hereinbefore, it is believed that the tonicity (or osmolality) of saliva may be a significant factor making saliva a hostile environment for cell survival. Saliva, especially saliva collected in donated samples, has been found to be hypotonic with respect to blood. Cells from blood that pass into a person's saliva are subjected to destructive osmotic pressure, drawing fluid into cells, causing the cells to swell, become damaged, and ultimately to burst. This may explain the low number of cells reported to survive undamaged in saliva. It may also explain why, for example, HIV is less transmissible by saliva than by other bodily fluids; cells, including HIV-infected cells, that pass from blood into saliva are not able to survive for long because the cells burst as a result of osmosis. Similar destruction and cellular damage applies generally to cells that pass from blood into saliva. The body compensates for such cell destruction by providing a high rate of blood flow to the salivary gland, enabling replenishment of the cells that perish in the mouth. Blood flow to the salivary gland is reported to be about 100 times greater than blood flow to skeletal muscle in the relaxed muscle state. Blood flow to exercising skeletal muscle increases up to about ten times, but even then the blood flow to the salivary gland still exceeds exercising muscle blood flow vastly by about ten times. This provides further evidence to the hostile environment of saliva, and rapid cell death in saliva thus requiring constant replenishment of cells.

By providing a preservative solution that is hypertonic with respect to blood, the solution can, when mixed with a saliva sample, neutralize the saliva's hypotonicity, and balance the tonicity towards an isotonic environment. Such an environment can avoid, or at least significantly reduce, osmotic pressure on cells in the collected sample, thereby enabling cells to survive undamaged for preservation, and enabling a significantly improved yield of preserved cells for analysis or diagnosis.

Obtaining an isotonic solution may be advantageous not just during preservation (e.g. fixation) of the saliva sample, but also during a period in which the preserved cells are stored awaiting processing or analysis. For example, preserved and/or fixed cells may still be vulnerable to osmotic pressure effects that can cause the cells to swell and burst and/or collapse and implode depending on the osmotic conditions affecting fluid transfer through the cell wall.

In some embodiments, the naturally expressed bodily fluid may be of a type that is naturally hypotonic, for example but not limited to oral fluids (e.g. containing saliva), and especially but not limited to saliva itself.

In some embodiments disclosed herein, the osmolality of the solution (e.g. prior to mixing with the bodily fluid) may be defined as being optionally about, or at least, (in either case) "n" times 240 mOsm/L, where "n" is a natural number between 2 and 15 inclusive. For example, "n" may be 2, 3, 4, 5, 6, 7, 8, 9, 10, 11, 12, 13, 13, 14 or 15.

In some embodiments disclosed herein, the osmolality of the solution (e.g. prior to mixing with the bodily fluid) may be defined as being optionally about, or at least, (in either case) "n" times 275 mOsm/L, where "n" is a natural number between 2 and 15 inclusive. For example, "n" may be 2, 3, 4, 5, 6, 7, 8, 9, 10, 11, 12, 13, 13, 14 or 15.

In some embodiments disclosed herein, the osmolality of the solution (e.g. prior to mixing with the bodily fluid) may be defined as being optionally about, or at least, (in either case) "n" times 290 mOsm/L, where "n" is a natural number between 2 and 15 inclusive. For example, "n" may be 2, 3, 4, 5, 6, 7, 8, 9, 10, 11, 12, 13, 13, 14 or 15.

Additionally or alternatively, the aggregate salt-ion osmolality in the solution (e.g. prior to mixing with the bodily fluid) may optionally be about, or at least, (in either case) "n" times 290 mOsm/L, where "n" is a natural number between 2 and 15 inclusive. For example, "n" may be 2, 3, 4, 5, 6, 7, 8, 9, 10, 11, 12, 13, 14 or 15.

In some embodiments disclosed herein, the osmolality of the solution (e.g. prior to mixing with the bodily fluid) relative to that of blood may be defined as being optionally about, or at least, (in either case) "n" times that of blood, where "n" is a natural number between 2 and 15 inclusive. For example, "n" may be 2, 3, 4, 5, 6, 7, 8, 9, 10, 11, 12, 13, 14 or 15.

Additionally or alternatively, the concentration of sodium chloride (NaCl) in the solution (e.g. prior to mixing with the bodily fluid) may optionally be about, or at least, (in either case) "n" times a concentration "m", where: "m" is a value in a range between 8.0 and 9.0 grams per liter (g/L) inclusive; and where "n" is a natural number between 2 and 15 inclusive. For example, "n" may be 2, 3, 4, 5, 6, 7, 8, 9, 10, 11, 12, 13, 14 or 15.

Additionally or alternatively, the solution may comprise phosphate-buffered-saline (PBS) in a concentration (e.g. prior to mixing with the bodily fluid) that is optionally about, or at least, (in either case) "n" times a blood-isotonic PBS concentration, where "n" is a natural number between 2 and 15 inclusive. For example, "n" may be 2, 3, 4, 5, 6, 7, 8, 9, 10, 11, 12, 13, 14 or 15.

In some embodiments, the solution (prior to mixing with a sample of a hypotonic naturally expressed bodily fluid) has a hypertonicity such that, upon mixing with a collected sample of the bodily fluid, the mixture of the solution and bodily fluid together is isotonic, wherein the tonicity is defined with respect to blood.

In some embodiments, the solution (prior to mixing with a saliva sample), has a tonicity such that, upon mixing with a collected saliva sample, the mixture of solution and saliva together is isotonic, wherein the tonicity is defined with respect to blood.

The preservation solution may contain at least one chemical fixing agent, such as but not limited to paraformaldehyde, and at least one protease inhibitor. In some embodiments, the solution may further contain one or more of at least one antimicrobial agent, and serum proteins from human and/or other animal species. The solution can be buffered at a pH from between about 6.4 to about 8.4, preferably from between about 7.2 to about 7.6.

In some embodiments, concentrations of agents in the following description can be those of the sample preserving solution itself. Depending upon the bodily fluid, and in the case of saliva, about an equal volume of solution and body fluid can be mixed together. This preferably results in the cells from the body fluids retaining their antigenicity and DNA integrity for at least one week at room temperature.

In some embodiments of the disclosure, the volume of preservation solution held within the device and deployed may be between about 100 and about 500 ml, which is relevant, for example, for the preservation of cells in urine. As such, the preservation solution for urine may be anywhere between about ten times (10×) concentrated solution to a one-point five time (1.5×) solution for urine.

A "chemical fixing agent", according to some embodiments, is a chemical cross-linking compound used to alter cell components such that the cells resist degradation. The chemical fixing agents can also serve to cross-link histones and other DNA-binding proteins to the DNA. Such agents may be known in the art and include, without limitation, paraformaldehyde, formaldehyde, formalin, aldehydes, alcohol, oxidizing agents, Mercurials, Picrates, Hepes-glutamic acid buffer-mediated organic solvent protection effect (HOPE), fixative combinations such as Zambonis fixative, combinations of aldehydes, and synthetic cross-linking reagents. In some embodiments, the chemical fixing agent is paraformaldehyde. In some embodiments, the chemical fixing agent is present at a concentration of about 1% (v/v).

Chemical fixing of extra-cellular components, such as proteins can bind the proteins by cross-linking them with other material, for example, other proteins or DNA. For example, proteins that were biologically bound to other material may be bound more firmly chemically with the same material by the cross-linking. Proteins that were merely in proximity with other material may be bound to that material by cross-linking. The cross-linking may preserve the protein by reinforcing the protein against undesired disintegration into smaller segments, e.g. avoid being broken down into peptides.

For example, the aldehyde group of paraformaldehyde reacts with nitrogen and other atoms of proteins. This reaction causes the formation of methylene bridges between proteins that are close by. This "traps" DNA (e.g. fixation causes proteins bound to DNA (transcription factors for example) to be immobilized in place due to the reaction with the fixative). Not only can DNA be captive between these methylene bridges, so can lipids, carbohydrates, DNA, and RNA.

The cross-linking may be at least partly reversible. Reversing the cross-linking may, for example, be a step in later downstream processing, for example, for the analysis of extra-cellular components such as proteins. For example, bacterial proteins and human proteins may have cross-linked with each other or free floating DNA. Reversing the cross-linking later downstream enables analysis.

To protect the cells from degradation by proteases present in the body fluids, in some embodiments, the solution can contain at least one protease inhibitor. In some embodiments, the protease inhibitor can be selected from the group consisting of Aspartic protease inhibitors, Cysteine protease inhibitors, Metalloprotease inhibitors, Serine protease inhibitors (e.g., serpins), Threonine protease inhibitors, Trypsin inhibitors, and Kunitz STI protease inhibitor. Some specific, non-limiting, examples include sodium azide, PMSF, Aprotinin, leupeptin, pepstatin, natural or synthetic proteinase inhibitors, and cocktail mixtures of protease inhibitors. Suitable concentrations of these inhibitors can include, without limitation, PMSF (Phenylmethylsulfonyl fluoride) Serine proteases at about 0.1-1 mM, Benzamidine Serine proteases at about 1 mM, Pepstatin A Acid proteases at about 1 μg/ml, Leupeptin Thiol proteases at about 1 g/ml, Aprotinin Serine proteases at about 5 μg ml, and Antipain Thiol proteases at about 1 μg/ml. In certain embodiments, the protease inhibitor is sodium azide at a concentration of about 0.01% (w/v).

To prevent damage to the cells from microbial contamination, some embodiments of the solution contain at least one antimicrobial agent. Suitable antimicrobial agents include, without limitation, antibacterial and antifungal antibiotics.

Preservation of cell architecture is enhanced by the presence of serum proteins, which may optionally be added to the solution in some embodiments. Additionally serum proteins may be used to neutralize osmotic difference between cells and solution. These can be from human or other animal sources. In some cases, whole serum may be used. For example, fetal bovine serum may be added, in some embodiments at about 1% (v/v).

Additionally or alternatively to any of the above, in some embodiments, the solution is substantially free of detergent. Detergents are sometimes used in some processing of biological samples to facilitate penetration through cellular material (by antibodies conjugated to fluorescent dyes for example) but, it is believed herein, at the cost of increased cell damage and cell loss. According to some embodiments of the disclosure, avoiding the presence of detergent can enhance the number of preserved cells, which may be especially advantageous bearing in mind the relatively sparse quantity in a saliva sample of certain cells of interest.

The solution according to the disclosure may include any combination of the foregoing embodiments.

In some embodiments of the disclosure, a method for preserving cells and/or extra-cellular components in one or more bodily fluids is disclosed. The method for preserving the cells and/or extra-cellular components can comprise contacting the body fluids with the solution according to the present disclosure. The body fluids can contain a variety of cell types and/or extra cellular components, and the cells and/or extra-cellular components in the body fluids can be preserved by the solution according to the present disclosure. While not critical to the present disclosure, a ratio of solution to body fluids of from about 1 to 1 is typically used.

The following examples are intended to further illustrate some embodiments of the solutions and methods for preserving cells and/or extra cellular components in body fluids and are not to be construed to limit the scope of this disclosure.

For example, a solution of PBS pH 7.4, 1% Paraformaldehyde, 1% FBS, and 0.01% NaN3 can be added at a 1:1 ratio with saliva, then T-cells can be purified and DNA extracted. The results of such a process are shown in FIG. 2. These results can demonstrate that the integrity of the antigenicity and DNA of T-cells was maintained for at least one week.

As shown in FIG. 3, further testing has demonstrated the efficacy of the solution in preserving T-cells in a saliva sample for extended durations, even at elevated temperature, and even after an extended shelf life.

In FIG. 3, the vertical axis represents the number of T-cells (in thousands) per ml of a saliva sample mixed with the preservation solution in a 1:1 ratio, as determined by analysis. The cell concentration is effectively halved compared to the original saliva sample, as a result of the 1:1 mix with the preservation solution.

The first (leftmost) column indicates the number of cells in three samples stored a room temperature for a few hours after sample collection and mixing with the preservation solution. The first column acts as a benchmark for assessing the cell numbers in other samples.

The second, third and fourth columns compare the number of cells in three groups of three samples each, stored at room temperature for a day, two days and 1 month, respectively, after sample collection and mixing with the preservation solution. The second to third columns show very little variation with each other or with the first column.

The fifth, sixth, seventh and eighth columns compare the number of cells in groups of ten samples each, stored for a period of three months after sample collection and mixing with the preservative solution, kept respectively at 4° C., room temperature, 30° C. and 40° C. Ten samples (instead of three samples) were used, because the test was focused on long-term preservation. The fifth to eighth columns show very little variation with each other or with the first column.

The final column repeats the test for the second column, using a sample group of ten samples, and using a preservation solution that has been stored (pre-use shelf-term) for 4 months. As above, ten samples (instead of three samples) were used, because the test was focused on demonstrating extended shelf life.

The graph illustrates that the preservative solution is highly effective at preserving T-cells in a saliva solution for an extended duration, over a wide range of temperature conditions, and even after an extended shelf-term. The solution may have a similar or corresponding preservation capability for other types of cells. The deviation amongst the cell numbers in the different columns can be explained at least by the usual differences in cell numbers from different people donating the samples and/or different samples even from the same person. The number of cells per ml is also eminently satisfactory for permitting downstream cell analysis.

Referring again to FIG. 1, steps 30 and 32, and optional step 42, may be carried out using any suitable apparatus or device(s). In a simple technique, step 32 and/or step 42 may be carried out manually by opening a separate container containing the preservative solution and/or pre-treatment agent, and manually adding the preservative solution and/or pre-treatment agent to the collected sample, and/or manually mixing the solution with the collected sample. However, in some embodiments, steps 30 and 32, and optionally step 42, may be carried out together (at 34) using a dedicated sample collection device 10 illustrated in FIG. 4 or 5. The device 10 may be of a type that may be suitable for home use, or at least without the need to visit a laboratory. The sample collection device 10 may, for example, be portable and/or be provided to a user at home (for example, via a postal or courier delivery), for the user to donate the sample of naturally expressed bodily fluid. Alternatively, the sample collection device 10 may also be convenient for laboratory or hospital use.

Figure 4:
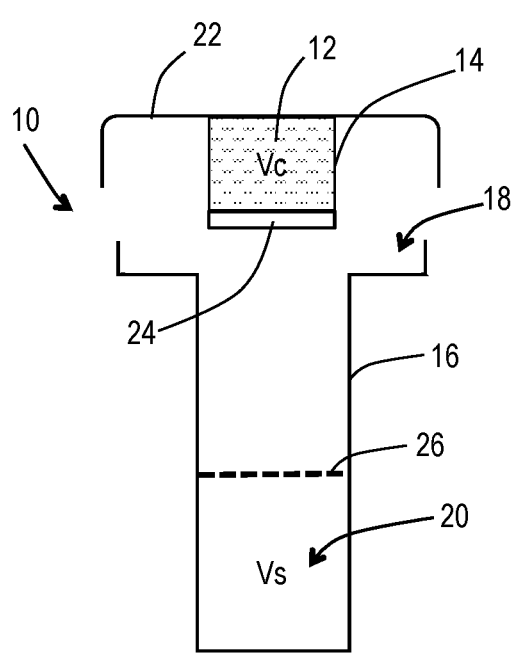
FIG. 4 is a schematic section through a first example sample collection device.
Figure 5:
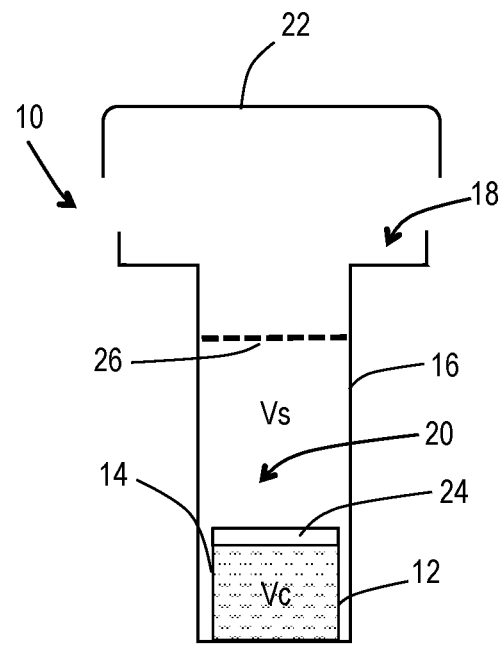
FIG. 5 is a schematic section through a second example sample collection device.

FIGS. 4 and 5 illustrate two alternative examples of collection device 10. The device 10 may generally comprise a first body (e.g. tube) 16 having a mouth 18 and defining a collection region 20 for the naturally expressed bodily fluid introduced into the device through the mouth 18. The device 10 may further comprise a second body (e.g. closure) 22 attachable to or over the mouth 18 to seal the device 10 closed after the donated sample has been introduced. The preservative solution 12, and/or a pre-treatment agent, may optionally be stored in at least one internal chamber 14 of the device, and released to mix with the collected bodily fluid sample when, for example, the user seals the device closed or performs some other manipulation of the device 10. In the example of FIG. 4, the chamber 14 containing the preservative solution 12 is provided in the second body (e.g. closure) 22. In the example of FIG. 5, the chamber 14 containing the preservative solution 12 is provided in the first body (e.g. tube) 16. In either example, the chamber 14 is configured to be opened by a mechanism (shown schematically at 24), to communicate with the collection region 20. The opening mechanism 24 may be responsive to fitting the second body (e.g. closure) 22 to the first body (e.g. tube) 16, or to some other manual manipulation of the device 10. Various mechanism 24 are envisaged, including but not limited to one or more selected from: release of an internal closure or cap, opening of a tap, rupture of a frangible wall, removal or displacement of an internal cover, relative rotation of a cap or nut.

In the illustrated examples, only a single chamber 14 is illustrated, e.g. for the preservative solution. If desired, a further chamber (not shown) may be provided for the optional pre-treatment agent, if used. The further chamber may be configured to be opened by the above opening mechanism, or a second opening mechanism. The further chamber may, for example, be opened before the chamber containing the preservative solution. In some embodiments, a sequential opening mechanism may be configured to only release the preservative solution after the pre-treatment agent has first been released.

Optionally, further details of exemplary constructions of device 10 and opening mechanisms 24 are provided in the aforementioned WO 2012/177656 incorporated herein by reference.

The device 10 may be configured for collection of a predetermined sample volume "Vs" of the naturally expressed bodily fluid. The device may, for example, include a visual fill scale, or a fill line (e.g. indicated at 26) or other indicia, to indicate when the predetermined sample volume Vs has been attained. In some embodiments, the sample collection space may have a size that is equal to the predetermined volume Vs, or the sample collection space may be larger in volume. By way of example only, the predetermined volume Vs may in some embodiments be at least about 1 ml, or at least about 2 ml, or at least about 3 ml, or at least about 4 ml, or at least about 5 ml, or more. By way of example only, the predetermined volume Vs may in some embodiments be not more than about 5 ml, or not more than about 4 ml, or not more than about 3 ml, or not more than about 2 ml, or not more than about 1 ml. By way of example only, in some embodiments, the predetermined volume Vs may in some embodiments be from about 1 ml to about 5 ml, optionally from about 1 ml to about 4 ml, optionally from about 1 ml to about 3 ml, optionally from about 1 ml to about 2 ml. By way of example only, the predetermined volume Vs may in some embodiments be about 1 ml, or about 2 ml, or about 3 ml, or about 4 ml, or about 5 ml.

In some embodiments, the volume "Vc" of the preservative solution 12 may be not substantially larger than, or optionally smaller than, the predetermined sample volume Vs. The preservative solution volume Vc may be same size as the interior space of the chamber 14 in order to fill the chamber 14, or the preservative solution volume Vc may smaller, partly filling the chamber 14.

By making the preservative solution volume Vc not substantially larger than, or optionally smaller than, the predetermined sample collection volume Vs, the volume increase when mixing the preservative solution 12 with the collected sample, can be equally small. The volume increase may be equivalent to dilution of the sample in terms of cell concentration per unit volume.

Referring again to FIG. 1, at step 36, the collected sample may be stored and/or transported to a laboratory for processing (optionally via an intermediary). For example, in the case of a sample having been donated at home, the collection device 10 may be sent via courier or postal services to a laboratory or to an intermediary for onward transportation. The time for transportation and/or storage prior to analysis by a laboratory may range from a few minutes, to hours, days, weeks or even months. The ability of the preservation solution to stabilize and preserve whole cells and/or extra-cellular components in the bodily fluid sample for extended periods, and over a wide range of temperatures, enables a wide range of analysis and diagnostic tools to be used for processing the naturally expressed bodily fluid as a viable alternative to sampling a patient's blood. Moreover, the yield of preserved cells in the sample, including the ability to preserve even rare or sparsely numbered cells, and the yield of extra-cellular components, opens the door to using a naturally expressed bodily fluid for new medical analysis, diagnostic and treatment monitoring applications.

At optional step 38, the preserved sample may be processed to enrich cell concentration and/or to isolate selected cell types and/or to separate certain extra-cellular components (e.g. any of: proteins, viruses, free-floating DNA and/or free-floating RNA).

In some embodiments of the present disclosure, a method is disclosed which provides a sample of one or more body fluids, such as saliva or urine, comprising chemically fixed cells and/or chemically fixed extra-cellular components, and optionally centrifuging the body fluid sample. Centrifuging may separate out certain extra-cellular components (e.g. any of: proteins, viruses, free-floating DNA and/or free-floating RNA) from a pellet of cells; including bacteria and debris.

Depending on the particular material of interest, either the pellet, or the liquid extra-cellular components, or both, may be further processed or analyzed.

For example, the method can further include enriching white blood cells, including lymphocyte cells, from other contents of the pellet. Additionally, specific cells may be isolated using antibodies conjugated to magnetic beads targeted to cell specific markers.

In some embodiments, the disclosure provides a method for isolating a particular type of white blood cell, specifically including, but not limited to lymphocytes, from bodily fluids (i.e., saliva, urine, etc.), comprising, for example one or more (and in some embodiments, several or all of the steps): providing a body fluid sample comprising chemically fixed cells, optionally centrifuging the body fluid sample to obtain a pellet comprising cells, optionally re-suspending the pellet in buffer, subjecting the re-suspended pellet to density gradient separation to obtain a layer of a mixture of white blood cell types (including lymphocytes), contacting the mixture of cell types with a solution containing specific binding agents for an epitope found on a particular type of white blood cell, and separating the particular type of white blood cell (including lymphocytes) from the mixture of white blood cell types.

In some embodiments, the specific binding agents can include magnetic beads coupled to antibodies specific to an epitope found on a particular type of white blood cell, and separating may comprise magnetically separating the particular type of white blood cell (including lymphocytes) from the mixture of white blood cell types, though any method (and corresponding system/device) for separating cell types from one another is within the scope of this disclosure. Magnetic separation is but one method for doing so.

The cells can be chemically fixed prior to being subjected to the method according to this disclosure. The cells can be chemically fixed by, e.g., contacting a sample of saliva with a chemical fixation solution. This is done to preserve the cells over time at ambient temperatures. This can also allow for a complete study of the epigenome as it allows histone modifications and other protein-DNA interactions to be studied from the deposited body fluid samples. Histones must be chemically fixed to the DNA in order to be studied.

Without fixation, the histones generally cannot remain bound to the DNA and the proteins can degrade over time.

In some embodiments, the buffer can comprise sodium azide, the buffer can comprise phosphate buffered saline and sodium azide, In some embodiments, the buffer may further comprise fetal bovine serum. In some embodiments, the buffer is at a pH from between about 7.2 to about 7.6.

In some embodiments, the cells are washed once in buffer. This in practice removes soluble material and in the case of saliva it removes what has been classified as the "buccal" layer (Dos-Santos et al, 2009).

In some embodiments, the mixture of white blood cells is washed one or more times in buffer prior to separating. This is preferably done to remove any remaining density gradient solution from the mixture of cell types.

In the process, the antibodies may bind to the particular type of white blood cells, thus binding the particular type of white blood cells to the magnetic beads. The particular type of white blood cells can then be separated from any other cell types by placing the magnetic beads in a magnetic field and removing any remaining liquid to obtain isolated cells of the particular type of white blood cells.

In some embodiments, the particular type of white blood cells can be a lymphocyte, where the lymphocyte may be a T-cell. In such embodiments, the antibodies used may be specific to an antigen specific to T-cells (e.g., the antigen being CD4). In some embodiments, the isolated blood cells may then be frozen prior to further processing, such as prior to epigenetic analysis.

The following example is intended to further illustrate an example method embodiment of the present disclosure and is not intended to limit the scope of the disclosure.

Example 1: Isolating T-cells from a bodily fluid (e.g., saliva). Saliva is collected, and the saliva is mixed with preservation solution. The cells are then pelleted by centrifugation and the processing solution is removed. The cells are then re-suspended in about 6 ml buffer (PBS, pH 7.4), 1% FBS, 0.01% NaN3), then washed once in a buffer and re-pelletted. The pellet is re-suspended in about 6 mL of PBS-15 FBS-0.01% NaN3 and subjected to density gradient centrifugation using 1.082-1.072 g/ml of Ficoll<®> (GE Healthcare). The white-blood cells are spun to the interface of the polysaccharides and buffer while the bacteria, debris, and any other particulate matter are pelleted at the bottom of the tube. The cells are extracted from the tube and placed in a new tube. The cells are then washed in Hank's Balanced Salt Solution once and then washed with the PBS-NaN3-FBS buffer once to remove remaining density gradient solution that may have been taken up while extracting the white blood cells from the interface.

Figure 6:
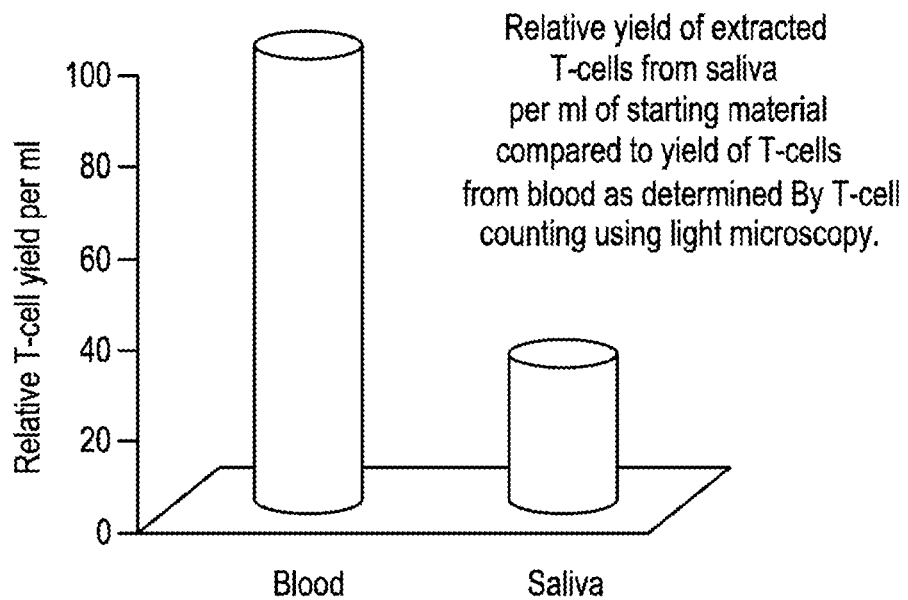
FIG. 6 is a chart illustrating the relative yield of extracted T-cells per ml of starting material (e.g., sample of bodily fluid), as compared to a yield of T-cells from blood.

The sample now includes highly enriched white-blood cells with minimal bacteria and minimal debris. This step can also greatly decrease other cell types, such as epithelial cells. The cells can then be incubated in buffer (PBS-NaN3-FBS) with an antibody targeted against CD4 conjugated to magnetic beads (Dynabeads® Invitrogen®). The samples can then be placed in a magnetic field, the beads brought to the side of the tube, and the liquid removed. The liquid may contain everything not bound to the beads through the antibody. The T-cells can be bound to the antibody and not removed due to the magnetic field. The beads and the attached cells can be washed in buffer to eliminate any non-specific or weak binding of other cells, bacteria, or other debris found in bodily fluids, such as saliva or urine. The cells can then be frozen for later downstream processing and analysis. The isolation of T-cells can be confirmed by light microscopy (T-cells are very distinct compared to epithelial cells and bacteria) (see FIG. 6). Additionally, flow cytometry and F.A.C.S. analysis using antibodies against CD3, CD4, and CD8 can confirm visual assessment of the isolated cells. The T-cells may then be tittered from the body fluid to determine the number of T-cells per unit of body fluid (ml) in order to determine the amount of body fluid, such as saliva or urine, for an adequate number of cells for downstream experimentation (see FIGS. 6 and 7). The isolated cells can be shown to have DNA devoid of degradation and appropriate for downstream use (see FIG. 2).

Referring again to FIG. 1, at step 40, the sample of interest (optionally enriched, or with cell types separated and/or isolated from step 38) is further processed for analysis or diagnosis. As mentioned above, step 40 may be carried out on separated cells, or on separated extra-cellular components. Optionally, a collected sample may provide both a whole cell sample and an extra-cellular component sample, and step 40 may be performed separately for each. Step 40 may include the same or similar analysis for each, or may include different analyses.

The ability to obtain a sample of a naturally expressed bodily fluid, preserved to provide a usable yield of rare or sparsely numbered cells, and/or extra cellular components, may provide an alternative technique to blood sampling, for diagnosis and/or monitoring of a patient's medical condition. Cellular and extra-cellular analyses may be used as a companion diagnostic and/or as a companion validator.

Techniques used for identifying specific cell types or other biomarkers in blood samples may also be used (either with or without modification) for identifying such cells or other biomarkers in the naturally expressed bodily fluid.

By way of example, cells and/or extra cellular components may be analysis to diagnose, indicate, identify and/or monitor one or more of:

(a) Cells with markers (cellular or molecular) that identify regression or aggression of disease. The disease may, for example, be cancer (optionally, but not limited to leukemia). In the case of the fluid being or containing sputum, the disease may be any one or more of: lung cancer, lung carcinoma, non-small cell lung carcinoma (NSCLC), pneumonia, or tuberculosis.

(b) Prenatal cells.

(c) Circulating tumor cells (e.g. metastatic or otherwise).

(d) Rare forms of normal cells, for example, any one or more of:
  Premature cells as in myelodysplastic syndrome;
  Epithelial cell sub-types indicating disease and not originating from the mouth;
  Langerhands cells, for example (but not limited to) diagnosis blood disorders.

(e) one or more biomarkers indicative of obesity (discussed below);

(f) one or more biomarkers indicative of bacterial infection version viral infection (useful to avoid unnecessary and inappropriate prescription of antibiotics). For example:
  TRAIL proteins (TNF-related apoptosis inducing ligands) can be used to discern infection (bacteria v. virus). This is very useful to combat antibiotic resistant bacteria.
  TRAIL proteins are cytokines that are secreted by most cells and as ligands induce the process of apoptosis.

(g) one or more biomarkers indicative of autism. For example:
  Oxytocin—influences the establishment of affiliative bonds. Negatively oxytocin in ASD is negatively correlated with 5-HT. UPolymophisms of the OXTR gene, encoding for the oxytocin receptor are associated with autism, pair-conding, social behavior, emotional affect, and ASD traits.

Melatonin—well established to play a role in circadian and seasonal rhythms and in the modulations of immune responses and neuronal plasticity. Welatonin is synthesized from 5-HT, which is transformed into N-acetlyserotonin and then melatonin via the enzyme: acetylserotonin methyltransferase (ASMT). A process inhibited by day time/light. Low levels of melatonin in the plasma of ASD patients seems to be due to a lack of this ASMT enzyme (epigenetic (DNA, protein, and RNA applicable analysis). ASMT gene variants are associated with ASD. The same gene also hosts disruptive coding mutations in six of 398 (1.51%) ASD individuals, compared to none of 437 controls.

Immunological Biomarkers of Autism (Extcellular and Intracellular):

Elevated IL-1 (interleukin 1)

Elevated IFN-γ (interferon gamma)

Over production of the anti-inflammatory cytokine, IL-10 (interleukin 10)

Abnormal post-thymic maturation of T-lymphocytes with increased naïve and decreased differentiated (ie CD4+ and CD8+) T cell counts.

(h) one or more biomarkers indicative of Alzheimer disease.

(i) one or more biomarkers indicative of hetotological disorders.

(i) one or more biomarkers indicative of cardiovascular diseases or disorders.

(k) one or more biomarkers indicative of diabetes (l) one or more biomarkers indicative of vulnerable clack, for example, relating to immune cell activity and/or immune cell biomarkers.

(m) one or more biomarkers, and/or one or more released factors, indicative of a dormant and/or latent and/or stealth form of a disease or infection. For example, such a disease may be LTBI. Additionally or alternatively, such factors may be peptides and/or cytokines.

In some examples, a pre-treatment agent may be added (step 42 of FIG. 1 described above) to the saliva before the preservation step. The pre-treatment agent may, for example, comprise antigens to a disease or infection to be detected, for provoking or stimulating release of certain factors in saliva if from an individual with the disease or infection. LTBI may be detected by using a pre-treatment agent of antigens (e.g. peptides from *M. tuberculosis*), recognized by lymphocytes and causing the release of factors such as Interferon Gamma in the saliva from an infected individual. The released factors, such as Interferon Gamma, can subsequently be assayed from the preserved saliva (e.g. quantitatively or qualitatively), and a diagnosis can be made.

Additionally or alternatively, in some examples, lymphocytes, for example, t-cells, may be analyzed epigenetically (including transcriptional and/or translational analysis) for LTBI based on the changes that cause cells to release interferon gamma when peptides from *M. tuberculosis* are added to cells. This may be done with, or without, the addition step 42 using a pre-treatment agent with, for example, antigens.

(n) Presence of HIV infection in cells.

There now follows a non-limiting discussion relative to HIV infection. Additional and/or alternative examples are also explained further below.

Any of the current saliva-based released antibodies/factors tests may be enhanced by the use of the preservation techniques of the present disclosure.

However, the current saliva-based techniques suffer from the drawback that they rely on the human immune system to generate antibodies/factors that can be detected, which generally involves a delay of at least 6 weeks. Such techniques may be classed as based on extra-cellular factors. During this time, existing saliva-based tests fail to diagnose the presence of HIV infection in an individual, which may in some cases lead to misleading results and/or may lead to the individual spreading the infection unknowingly to others.

The present disclosure also proposes use of saliva (or another naturally expressed bodily fluid) to enable detection of HIV infection (i) in the period before the body's immune system generates antibodies/factors than can be detected; and/or (ii) without the at least 6 weeks delay following infection of an individual.

In some embodiments, the present disclosure permits the analysis of HIV virus within preserved infected cells of saliva (or another naturally expressed bodily fluid). Blood cells, for example, t-cells including CD4+ t-cells may be preserved and/or isolated and/or analyzed to identify the presence of HIV virus within the cell. The disclosure thus permits intracellular analysis from e.g. saliva, enabling the detection of HIV virus much earlier after infection than the above extra-cellular tests, for example, earlier by at least 6 weeks or more.

In some embodiments, within t-cells, the viral RNA or the reverse transcriptased DNA or the proteins that the virus brings with it (e.g. any of reverse transcriptase, proteases, ribonuclease and integrase) may be analyzed.

In some embodiments, after preservation of e.g. saliva, and isolation of the CD4+ t-cells, the cells may be lysed and the DNA and/or RNA and/or intracellular proteins obtained and/or isolated. Optionally, PCR may be performed with probes targeting unique sequences of the HIV virus. Additionally or alternatively, the diagnostic platform could look at the proteins that during early infection HIV uses to integrate into the DNA genome. Such analysis may be proteomic in nature, and could include, merely by way of example, assays such as mass spectroscopy, ELISA, or other antibody mediated analysis. Antibody analysis may be performed in respect of the proteins of the HIV virus (rather than those released by the immune cells as described above).

Additionally or alternatively, the measurement of the number of CD4+ cells in the sample (e.g. saliva) may itself be indicative of HIV infection, because HIV actively eliminates CD4+ cells from the body's immune repertoire, causing AIDS. In some embodiments of the present disclosure, the number of CD4+ cells may be assessed, for example, by flow cytometry and/or FACS to provide such an indication from a preserved sample.

(o) one or more biomarkers indicative of cancer.

(p) one or more biomarkers indicative of chronic obstructive pulmonary disease (COPD).

(q) one or more biomarkers indicative of drug resistant Tuberculosis.

(r) one or more biomarkers suitable for replicating and/or substituting one or more tests from the following categories of blood tests: electrolyte levels; lipid tests; vitamin levels; Hepatitis tests; iron deficiency tests; liver function tests; renal profile tests; diabetic screening tests; hemogram tests; thyroid profile tests.

(s) one or more biomarkers indicative of a type of COPD being "asthma COPD overlap syndrome" (ACOS).

Optionally, such biomarkers can provide a companion diagnostic to a general diagnosis of COPD, for detecting that the COPD is ACOS. Additionally or alternatively, such biomarkers can provide a companion validator to monitor efficacy of treatment targeting ACOS. Additionally or alternatively, a general diagnosis of COPD may, for example, be performed using the biomarkers referred to in (p) above, and/or the general diagnosis of COPD may be performed using other conventional diagnostic tests.

Regarding (a) above, more information about non-small cell lung carcinoma (NSCLC) is now explained by example only. Roughly 80% of all lung carcinoma is NSCLC (5). Early diagnosis and treatment for NSCLC optimizes outcomes (12). A major component of conventional diagnosis involves direct visualization of suspected cancer cells microscopically (6). This is an established laboratory application involving lung biopsy material.

In contrast, sample collection of oral fluid using the techniques of the present disclosure may provide easier access to a source of respiratory cancer cells. It is believed that oral fluid testing may provide a "liquid biopsy" able to at least support and even enhance current clinical practice (3, 4, 7). It is believed that oral fluid diagnostics may extend to other cancers (48), as well as several other diseases amenable to this matrix (49).

The detection and identification of putative cancer cells, and particularly cancer stem cells (CSC) is an active part of current cancer research and patient management (8). Relying on recent scientific research data findings, it is believed that a modest biomarker panel to allow identification of NSCLC/CSC (in already diagnosed patients) may provide significant advantages.

Example biomarkers may include CD133 and/or EpCAM (10,11). Additionally or alternatively, example biomarkers may include EGFR and/or ALK.

Some biomarkers may, for example, be detected in preserved whole cells of a bodily fluid sample. Additionally or alternatively, some biomarkers may, for example, de detected in a preserved sample of lysed cells from a collected bodily fluid (for example, using a preservation solution that accesses nucleic acids in some embodiments of the present disclosure—optionally see Annex 1).

CD133 is a biomarker strongly associated with immortalized (stem cell) cells, and EpCAM (epithelial cell adhesion molecule) is a well-known biomarker expressed exclusively in epithelia and epithelial-derived neoplasms. EpCAM can be used as diagnostic marker for various solid tissue cancers. It appears to play a role in tumor genesis and metastasis of carcinomas. As such, it can also act as a potential prognostic marker and as a potential target for immunotherapeutic strategies. EpCAM capture/detection is a critical component of existing circulating tumor cell (CTC) assays in whole blood, already in clinical practice.

Used together as a reflex and monitoring clinical assay via the techniques of the present disclosure, a physician may obtain valuable information on patient progress and prognosis. The repertoire of such additional targets (gene rearrangements, SNPs), amenable to testing may be extensive for any tumor and the subject of active research (5, 6, 13).

An advantage is that the techniques of the present disclosure may enable patient sample procurement and stabilization to be achieved more easily than with other approaches. Follow-on assays may be facilitated with retained patient material via the "liquid biopsy" proposition (14). There are a myriad of attractive biomarkers (5, 6, 13) that might be evaluated by reflex testing. For example, in patients diagnosed with NSCLC, it is highly advantageous to be able to determine early drug treatment and subsequent options as drug resistance unfortunately develops via genomic sequence mutation, and may occur at any time prior to or during drug treatment.

Two assays that may be relevant to patient management involve testing for mutations in any of several genes known to be involved with therapeutic drug resistance and monitoring (5, 6, 15, 16). In advanced cases, mutations in the epidermal growth factor receptor gene (EGFR), and chromosomal rearrangements in the ALK gene may be significant for drug choice. At a finer level, several other genes are also important to disease treatment such as VEGF, but EGFR/ALK are a major immediate focus of therapeutic modulation (50).

The EGFR specific drugs Gefitinib (Iressa)-Astra Zeneca, Erlotinib (Tarceva)-Genentech, Afatinib (Gllotrif)-Boehringer Ingelheim require analysis and monitoring of EGFR sequence changes. The ALK focused drugs Crizotinib (Xalkori)-Pfizer, and Ceritinib (Zykadia)-Novartis also require monitoring of patient gene rearrangements.

Important advantages may be achieved in relation to initial and ongoing patient gene sequence vigilance. These tests may be facilitated via tumor cell interrogation, for example, using a preserved lysed bodily fluid sample (for example, using the techniques of Annex 1).

Assays may be performed via advanced cytological methods (e.g. IHC, FISH) (9, 18) based on preserved whole-cell samples, or more directly by nucleic acid hybridization testing using preserved lysed samples (for example, using the techniques of Annex 1 optimized to isolate nucleic acid (19).

Envisioned is a test using CD133/EpCAM interrogation of oral fluid borne cells, optionally followed by reflex assay of (but not limited to) drug resistance associated genes such as EGFR/ALK. Approximately 10% of NSCLC tumors will exhibit the EGFR or ALK mutations (50).

Regarding (e) above, more information is now explained by example only. Global and gene specific changes in epigenetics (DNA methylation and histone acetylation) have been correlated to obesity. Selected genes whose expression is likely causally related to obesity (protein and RNA level of analysis):
Leptin (LEP)
Leptin receptor (LEPR)
Brain derived neurotrophic factor (BDNF)
Proopiomelanocortin (POMC)
Single minded homologue 1 (SIM1)
Neurotrophic tyrosine kinasereceptor type 2 (NTRK2)
FTO (fat mass and obesity)
Selected Epigenetic Biomarkers, Shown to be Linked with Obesity:

| | |
|---|---|
| GNB3 | Encodes β3-subunit protein which is involved in the process of hypertension and obesity |
| MTHFR | Gene encodes methylenetetrahydrofolate reductase that is shown to be associated with increased fasting homocysteine. Polymorphism is shown to be associated with lipid metabolism in the elderly women |

-continued

| Gene | Description |
|---|---|
| CNR1 | Associated with low HDL dyslipidemia and a common haplotype of CNR1 could be a protective factor of obesity-related dyslipidemia |
| BDNF | Role in the development of several neuronal systems, via energy homeostasis, has an effect on glucose and lipid metabolism in obese diabetic animals |
| FAAH | Encodes fatty acid amide hydrolase and plays an important role in the development of obesity |
| ADRB1 | Shown to mediate in lipolysis and thus is important for obesity> Mediates sympathetic nervous system and stimulation of brown adipose tissue thermogenesis |
| SH2B1 | Binds leptin to its receptor, and thus increases the JAK2 activation which is involved in the insulin and leptin signaling |
| PCSK1 | Encodes prohormone convertase 1/3 that is a vital enzyme in the regulation of a majority of neuroendocrine body weight control (novel homozygous missense mutation in PCSK1 leads to early-onset obesity) |
| NPY2R | Presynaptic receptor playing an inhibitory role in the control of appetite regulation, and thus influences the development of obesity |
| FAIM2 | Fas apoptotic inhibitory molecule 2 is an anti-apoptotic gene. Mutations of FAIM2 which interferes with Fas-mediated cell death confer risk for obesity |
| SERPINE1 | Encodes a member of serine proteinase inhibitor which influences plasma PAI-1 activity with relation to obesity |
| PON1 | Serum paraoxonase-1 is an an enzyme associated with HDL-C could be a protector against oxidative damage in obesity |
| CETP | Protein product transfers cholesterylesters from HDL to pro-atherogenic apoB-lipoproteins and thus has an impact on the lipid and HDL metabolism |
| UPC1 | Encodes uncoupling protein 1 that is mediated by long-chain fatty acids (LCFAs) from brown adipose tissue. (UCP1 expression in adipose tissue has an impact on regulating the thermogenesis and lipolysis. Mitochondrial uncoupling by UCP1 has emonstrated to be a target in antiobesity therapies) |
| ABCA1 | Gene product mediates the transport of cholesterol, phospholipids, and other metabolites. Exercise has an impact on ABCA1 expression along with increased HDL levels in obese boys |
| APOE | Fundamental role with ligand-receptor in uptaking lipoproteins, and thus participates in the lipid metabolism. In addition, APOE correlates with inflammation in adipose tissue in high-fat diet-induced obesity |
| FABP3 | Its methylation in peripheral white blood cells is associated with plasma total cholesterol, insulin sensitivity and blood pressure |
| PGC | Epigenetic alterations were associated with reduced mitochondrial density and increased plasma free fatty acid concentration |
| MC4 | Hypomethylation has a direct impact on appetite and intake, and thus influences risk of obesity |

Referring to (n) above, the following provides additional and/or alternative example information. There have been tremendous advances in the last decade regarding the amplification, detection and sequencing of nucleic acids (27, 37, 38 generic reviews). Reagents, primer sequences, and protocols exist and are readily available. Other than high throughput and esoteric testing, there continues to be a need for facile sample handling and processing in otherwise routine applications. Saliva, and oral fluid in general, have recently seen advances as novel matrices for nucleic acid testing (39, 40, 41). There is much interest in utilizing this relatively "user friendly" fluid for a variety of gene/sequence detection methods (42).

A saliva based test for BRACA1 gene sequence (breast cancer predisposition) was announced to be in development (Color Genomics), and showed early utility as a surrogate for the existing cellular blood based test. Most established providers of gene sequence platforms have accommodated specific protocols for saliva matrix (43), and thus there is good reason to expect saliva to be able to be used for the detection of other infectious agents, analytes, and nucleic acid sequence alterations in the future (44, 45).

A relevant collection of resource links herein for further reference (47, 48) is provided concerning usable techniques.

An example biomarker for HIV Sequence Detection may be CD4 cells, for example, for analysis via FISH/IHC methods. A further biomarker detection via PCR is also discussed later below.

The techniques disclosed herein provide a saliva sample collection device that allows for the preservation and isolation of a spectrum of cells from saliva or induced sputum. These cells may be visualized by several microscopic methods (9). As described above for NSCLC, this existing system also allows for the interrogation of fixed cells by a myriad of immuno-histochemical methods (IHC) (18). This analysis may include the detection of CD4 cells displaying any of several HIV protein biomarkers. An abundance of IHC qualified detection antibodies are commercially available for this purpose (9). The sample collection techniques disclosed herein may be amenable to sequence specific nucleic acid amplification and detection methods such as gene specific FISH (fluorescence in situ hybridization) (51). This is a well-accepted and important methodology, similar to cytological analysis, that allows for the detection of DNA/RNA sequences (both native genomic and viral) within fixed cells by common microscopy and imaging techniques. There are well accepted and validated protocols available for this methodology. The selection of optimized hybridization probes and PCR primers, directed at various genome regions of the HIV virus, is well understood and readily available (52).

The detection of specific HIV virus sequences, both as integrated provirus, as well as virion particles, involves the treatment of microscopic slides, containing the preserved oral fluid cells, with "labeled" hybridization probes specific to well-known HIV genomic sequences. In CD4 cells in particular, where the life cycle of the virus is best understood, chromosomally integrated "provirus" sequences will hybridize to the chemically labeled probes and be subsequently visualized (2). Sensitive protocols exist that are validated for low copy virus loads as well (54). These probes are synthetic matches to the virus genome sequences, and would carry any of several available signal generating "label" moieties (biotin/streptavidin, ferritin, HRP enzyme, fluors, etc.).

A further or alternative example biomarker for HIV Sequence Detection may involve PCR. The detection of HIV sequences by PCR is technically straightforward, with many available reagent systems and amplification detection options available. Sequences, probes and primers are well understood and obtainable. Many well established protocols exist (37, 38, 47 by review).

Both HIV virus and anti-HIV antibodies can be detected in saliva, providing an alternative to blood to detect HIV antibodies to diagnose HIV infection (42, 43). Saliva HIV antibody tests, with specialized devices for proper saliva specimen collection, are currently licensed by the U.S. Food and Drug Administration (FDA) (e.g. OraSure). These tests are used in resource-limited settings as well as domestic public health clinics where rapid testing and ease of use are preferred.

The Centers for Disease Control (CDC) has included rapid and frequent HIV testing as part of its policy recommendations for HIV prevention programs (cdc.gov). In the case of virion particles, limited data indicates that while lateral infectivity may be low, viral genomic sequences may be detectable by sensitive PCR "viral load" assays nevertheless. This appears to be especially true during the early phases of infection, and perhaps during the "window" period during which antibodies first appear (39, 40, 55).

Early studies showed that between 42%-91% of individuals with early HIV infection were positive by sensitive PCR assays using saliva matrix (41, 55). Indeed, dramatic reductions of HIV RNA were seen in patients commencing combination drug therapy. Thus, an oral fluid/saliva sample collection device, capable of seamlessly integrating with a well formatted HIV specific PCR detection system, has the potential to offer tremendous advantage in the clinical and surveillance settings.

Referring to (p) above, more information is now explained by example only. COPD is a complex respiratory inflammatory disease that is quite difficult to unequivocally diagnose (20, 21, 22). It presents with clinical symptoms similar to other respiratory syndromes, and leads to complex serum biomarker alterations that are not in themselves specific, other that as indicators of system wide "inflammation". However, it is understood to be the fourth highest cause of death in the world. While it is not currently curable, there are treatments to extend life.

Using the principles of the present disclosure, one or more of the following biomarkers may be suitable for detecting the COPD in a collected bodily fluid sample: VAP-1; CD44; CD11b; eosinophil level (e.g., oral fluid eosinophil level and/or sputum eosinophil level).

There is significant ongoing discussion regarding the most appropriate diagnostic biomarker(s) options for therapeutic management. Recent research data have identified additional new biomarkers of inflammation and disease progression, and the field is rapidly identifying more specific cellular markers, of both infiltration and inflammation, that may provide more efficacious intervention (23, 24). The sample collection and analysis techniques described herein may provide a facile tool with which to directly evaluate early cellular diagnostic indicators of respiratory decline, and contribute to early therapeutic intervention.

While many of the current biomarkers of respiratory/inflammatory disease are soluble analytes, easily and routinely measured in the blood, - - - there is also emerging data to indicate that invasive neutrophils and eosinophils play a significant role in airway decline (25, 26, 27, 28, 29).

One recent study has identified a novel biomarker VAP-1 (30), present on airway endothelial cells, as a molecular "brake" element, early in the adhesion cascade, that consequently is responsible for mediating and moderating infiltrating neutrophils involved in the inflammatory process. Experimental drugs that inhibit this ligand have been shown to have a dramatic effect in animal models of respiratory disease, and COPD models in particular.

Integral to the proper functioning of neutrophils in lung defense is their ability to egress from the microvasculature and migrate through tissues to the targeted site. Upon injury of organs, neutrophils up-regulate expression of specific cell surface receptors (such as CD44 and CD11b co-expression, and others), and these biomarkers subsequently bind to adhesion molecules on endothelial cells, such as VAP-1 (31, 32, 33). Enabling neutrophil transmigration through the endothelial cell lining into the underlying parenchyma is essential for health, but if this process is not limited, uncontrolled inflammation ensues. CD44 and CD11b, on neutrophil PBMCs, have been shown to have such up-regulatory behavior, and may serve as early indicators of COPD related airway neutrophil infiltration, as well as perhaps allowing ongoing monitoring of disease progression or therapy. In fact, the belief that specific subsets of infiltrating neutrophils (e.g. as measured in sputum) may propagate or exacerbate COPD has generated interest in novel therapies.

Additionally or alternatively, eosinophil levels may provide a further indication as a biomarker, especially for ACOS (see the example for (s) further below).

Regarding (q) above, more information about tuberculosis is now explained by example only. The diagnosis and treatment of *M. tuberculosis* continues to be a major health concern both in developing as well as developed countries. It has become clear in the last decade that the bacterium may develop resistance to the limited armament or therapeutic drugs currently available. Additionally, understanding the individual patient's status, as far as type and frequency of resistance associated mutations, would allow the physician to better treat and even anticipate threatening shifts and outbreak of new infectious agents. This is a technical challenge involving nucleic acid sequence analysis and extensive gene data bases pertaining to drug resistance alleles. As the infectious organism is clearly a respiratory tract agent, the techniques of the present disclosure, including the ease and safety of patient management, may provide important advantages for patient management.

Some biomarkers may, for example, be detected in preserved whole cells of a bodily fluid sample. Additionally or alternatively, some biomarkers may, for example, de detected in a preserved sample of lysed cells from a collected bodily fluid (for example, using a preservation solution that accesses nucleic acids in some embodiments of the present disclosure—optionally see Annex 1).

Regarding (r) above, it was not hitherto feasible to replace routinely done blood testing with saliva based tests. However, by using the techniques of the present disclosure, most routine blood testing (most of the complete blood count and the evaluation of many diagnostic markers) can now become feasible with saliva.

Below is a table which lists many (but not all) tests commonly ordered by a physician necessitating a blood draw (first column). This first column lists a variety of tests, evaluating most of the critical factors in blood that taken together ensure the health and proper equilibrium of a patient. Most of these tests are not specific stand-alone diagnostics, but factors that contribute and assist in diagnosis. The middle column indicates the feasibility, as currently believed, of implementing a substitute and/or replacement test using the techniques of the present disclosure, and a saliva sample instead of a blood sample. The right column indicates whether or not currently available, commercial saliva kits for genetic analysis may be used to perform these tests, according to best belief and understanding.

Categories of Blood Factors Evaluated:

Electrolytes: Blood electrolytes are routinely ordered for the monitoring and evaluation of a patient's general health. Electrolyte measurements allow for the detection of any disequilibrium in the body and the monitoring of acid-base imbalances. An imbalance of any individual electrolyte warrants further investigation and monitoring, and/or may be indicative of a larger health problem.

Lipids: The lipids contained in blood are evaluated as part of the cardiac risk assessment screening to assess whether or not a patient is at risk of developing cardiovascular disease. Accordingly, these tests also help determine a patient's need for medication and/or changes in medication posology.

Vitamins: Vitamin D and vitamin B12 often require measurement to determine deficiency, or adequate supplementation if deficiency. Further, vitamin B12 is often examined in the diagnosis of neuropathy and certain anemias.

Hepatitis: HBsAg is a surface antigen on the Hepatitis B virus. Detection of this factor in blood confirms a diagnosis of Hepatitis B.

Iron Deficiency Profile: These tests are used to evaluate the levels of iron in a patient's body, whether too much or too little and the corresponding need for supplementation.

Liver function tests: To screen for, detect and monitor liver inflammation and liver disease. Both acute and chronic liver inflammation as well as liver damage are evaluated by the fluctuations of these factors and enzymes.

Renal profile: This panel of tests assist in the management and diagnosis of conditions with renal implications. These tests may constitute part of routine blood work simply to ensure the proper functioning of the kidneys, or may serve to screen and/or follow a patient who has or is at risk of developing kidney disease.

Diabetic Screening: These are tests ordered to diagnose whether a patient is diabetic, as well as assist in monitoring and managing the patient's diabetes by evaluating the level of control on blood sugar.

Hemogram: Also known as a complete blood count (CBC), is a broad screening tool evaluating a patient's general health and detecting numerous disorders, such as anemia, infections and certain cancers. CBCs include an assessment of the cellular components of blood (red blood cells, white blood cells, platelets and their ratios) as well as the measurements of various aspects and factors in blood.

Thyroid Profile: A panel of tests to assess the proper functioning of the thyroid gland or to diagnose an imbalance indicating a thyroid disorder.

The table referred to above now follows:

| Individual tests and factors detected/measured from blood samples | FEASIBILITY TO DETECT/MEASURE WITH SALIVA COLLECTED AND/OR STORED AND/OR PROCESSED AS DESCRIBED HEREIN | Feasibility of test with saliva genetics kits |
|---|---|---|
| Electrolytes (4) | | |
| Sodium | Yes | Not known |
| Potassium | Yes | Not known |
| Chloride | Yes | Not known |
| Bi-carbonate | Yes | Not known |
| LIPID (9) | | |
| Total Cholestrol | Yes | No |
| HDL Cholestrol | Yes | No |
| Triglyceride | Yes | No |
| LDL Cholestrol | Yes | No |
| VLDL Cholestrol | Yes | No |
| TC/HDL Ratio | Yes | No |
| TG/HDL Ratio | Yes | No |
| HDL/LDL Ratio | Yes | No |
| LDL/HDL Ratio | Yes | No |
| Vitamins (2) | | |
| Vitamin D | Yes | No |
| Vitamin B12 | Unsure (B12 binding proteins present) | No |
| Heptits B | | |
| HBSAG | Yes | No |
| Iron Defficiency Profile (3) | | |
| Total Iron | Yes | Not known |
| TIBC | Yes | No |
| % Transferrin Saturation | Yes (Saliva transferrin) | No |
| Liver Function Test (13) | | |
| Total Bilirubin | Yes | No |
| Direct Bilirubin | Unsure | No |
| Indirect Bilirubin | Unsure | No |
| Alkaline Phosphatase | Yes | No |
| SGOT | Yes | No |
| SGPT | Yes | No |
| GGT | Yes | No |
| Total Proteins | Yes | No |
| Albumin | Yes | No |
| Globulin | Yes | No |
| Albumin/Globulin Ratio | Yes | No |
| Total Proteins/Albumin Ratio | Yes | No |
| AST/ALT Ratio | Yes | No |
| Renal Profile (7) | | |
| Urea | Yes | Not known |
| Creatinine | Yes | Not known |
| Blood Urea Nitrogen (BUN) | Yes | Not known - but unlikely |
| BUN/Creatinine Ratio | Yes | Not known |
| Uric Acid | Yes | Not known |
| Calcium | Yes | No |
| Serum phosphorus | Yes (Salivary phosphatase) | Not known |
| Diabetic Screening (3) | | |
| HbA1c | Not direct equivalent but Saliva equivalent: 1,5 anhydroglucitol | No |
| Avarage Blood Glucose | Yes (Salivary glucose) | Not known |
| FBS | Yes | Not known |
| Hemogram (21) | | |
| Luecocytes (WBC) count | Yes | No |
| Neutrophils | Yes | No |

| Individual tests and factors detected/measured from blood samples | FEASIBILITY TO DETECT/MEASURE WITH SALIVA COLLECTED AND/OR STORED AND/OR PROCESSED AS DESCRIBED HEREIN | Feasibility of test with saliva genetics kits |
|---|---|---|
| Lymphocytes | Yes | No |
| Monocytes | Yes | No |
| Eosinophils | Yes | No |
| Basophils | Yes | No |
| Atypical Lymphocyte (ALY) | Yes | No |
| Large Immature Cells (LIC) | Yes | No |
| Neutrophils-Absolute Count | Yes | No |
| Lymphocytes -Absolute Count | Yes | No |
| Monocytes-Absolute Count | Yes | No |
| Eosinophils - Absolute count | Yes | No |
| Basophils - Absolute Count | Yes | No |
| Atypical Lymphocyte (ALY)-Absolute | Yes | No |
| Large Immature Cells (LIC)-Absolute | Yes | No |
| Mean Corpuscular Volume (MCV) | Yes | No |
| Erythrocyte Sedimentation Rate (ESR) | Yes | No |
| WBC Morphology | Yes | No |
| Immature Cells | Yes | No |
| Blast Cells | Yes | No |
| Hemoparasites | Yes (Some, but unsure about all) | No |
| Thyroid Profile (3) | | |
| T3 | Yes | No |
| T4 | Yes | No |
| TSH | Yes | No |

Regarding (s) above, more information about "asthma COPD overlap syndrome" (ACOS) is now explained by example only. ACOS is a condition that occurs when a patient suffers from both COPD and asthma. As already explained for (p) above, "chronic obstructive pulmonary disease" (COPD) is a disease that affects nearly 5% of the population and is associated with both high morbidity and mortality. The disease state is characterized by chronically poor airflow in patients and involving both emphysema and chronic bronchitis. Recently a new subtype of COPD, "asthma COPD overlap syndrome" (ACOS) has been found to afflict between 10-40% of all patients (Leena George, 2016). ACOS is a condition that presents the symptoms of COPD and asthma as well as a mixed pathology, all lending to it being a more extreme form of COPD. Typically the age of onset for ACOS is earlier than other COPD patients and the cost of medical care per annum for these patients is three times as high (asthma patients: $2307, COPD patients: $4879, ACOS patients: $14917) (Fadia T. Shaya, 2009).

ACOS has been jointly defined by GOLD (Global initiative for chronic Obstructive Lund Disease) and GINA (Global Initiative for Asthma) as, "characterized by persistent airflow limitation with several features usually associated with asthma and several features usually associated with COPD". Due to the vagueness of this definition, ACOS is currently not only inadequately defined but also challenging to diagnose based on presentation in clinic. However, correct diagnosis is important because it is understood that patients suffering from ACOS may respond sub-optimally to usual COPD treatments. Conversely, ACOS treatments are expensive, and should be targeted on patients with conditions mostly likely to be treated successfully.

The sample collection, preservation and analysis techniques described herein may be especially suited to allow preservation and subsequent staining and enumeration patient eosinophil counts, while simultaneously allowing for detection of other significant cells and associated biomarkers from the same sample (see above). These techniques may offer clinicians a valuable new theranostic tool with which to evaluate and monitor the treatment of COPD patients.

As further clinical data develops, this application may also play a role in the differential diagnosis of, for example, asthma.

ACOS has been shown to be more responsive to certain medications that can help manage patients at stable state and more importantly, manage and prevent exacerbations. One such group of medications is inhaled and oral corticosteroid therapy. Steroids are considered a broad-spectrum approach to managing ACOS due to their ability to decrease eosinophilic bronchial mucosal inflammation (Leena George, 2016). Other narrow-spectrum therapeutics are currently being investigated for use in ACOS that would specifically target eosinophilic/Th-2-mediated inflammation (Leena George, 2016). Such therapeutics have the potential to not only improve the quality of life of ACOS patients by managing symptoms and exacerbations, but also to decrease the medical costs and ascribed economic burden.

Based on this understanding of ACOS and the therapeutics in the pipeline, it becomes of greater importance that an adequate and efficient diagnostic tool be developed that can not only aid in the diagnosis of ACOS but also act as a companion diagnostic and/or companion validator to validate the efficacy of therapeutics. The traditional options of blood testing and bronchoscopy each have their limitations and disadvantages. Sputum testing has been shown to be advantages in COPD patients due to the local infiltration of inflammatory cells, thus suggesting that a higher concentration of inflammatory cells, such as eosinophils may be present in sputum. However, sputum samples are also cumbersome and challenging to obtain. Oral fluid has been shown to contain saliva and sputum, and due to increased sputum production in COPD/ACOS patients, oral fluid may present a non-invasive means for diagnosis and evaluation of many cellular and inflammatory biomarkers. Use of the techniques described herein for the preservation of all the contents of oral fluid, and isolation and evaluation of eosinophils and key biomarkers, can provide significant advantages not hitherto achieved nor envisaged.

Having discussed biomarkers that may be detected or analysed for different medical conditions, the following description now explains different techniques that may be used to perform, for example, many of the above.

In some embodiments, techniques used to diagnose or monitor a medical condition of a patient, optionally but not exclusively limited to, analysis of rare cells in a naturally expressed bodily fluid (e.g. saliva, sputum, urine), and/or analysis of extra-cellular components, may include one or more of:

(a) Flow cytometry;
(b) Fluorescence-activated cell sorting (FACS);
(c) Immunohystochemistry;
(d) Molecular analysis (for example, but limited to any of: epigenetic; genetic; translational; post-translational);
(e) Cytology.
(f) Protein level (post transcriptional) analysis techniques.
(g) RNA level (transcriptional) analysis to measure gene expression.
(h) DNA, e.g. epigenetic, and/or including DNA methylation and histone modifications.

The following further examples are intended to further illustrate an example method embodiment of the present disclosure and are not intended to limit the scope of the disclosure.

Example 1: Flow cytometry may be used to diagnose various forms of cancer. It is a test used by, for example, the Cancer Treatment Center of America to diagnose, for example, leukemia and lymphoma. Flow cytometry may also be used for the analysis of other types of cells, for example, platelets cells in blood. For example, Quest Diagnostics utilizes flow cytometry to diagnose paroxysmal nocturnal hemoglobinuria (PHN).

Example 2: FACS may be used to diagnose various cellular markers including those for cancer. It is a test used by, for example, Quest for the diagnostic of cellular markers such as CD57, CD8, CD3. FACS analysis can also be useful for monitoring the status of HIV/AIDS treatment via examining CD4 testing; BD Biosciences, for example, offers FACSCount™, a system designed for dependable CD4 testing. FACS analysis is also used for assessing forms of cells death and mitochondrial damage; EMD Millipore, for example, offers a variety of tests to assess cellular health and integrity.

Example 3: Immunohistochemistry may be used to diagnose various cellular markers including those for cancer and other disorders/diseases. It is a test used by, for example, Quest for the diagnostic of numerous cellular markers involved in disease. Merely by way of example, reference may be made to questdiagnostics.com.

Immunohistochemistry may also be used in the diagnosis of carcinomas and some sarcomas via detection of cytokeratins. Invitrogen, for example, offers an immunohistochemistry kit for the detection of cytokeratins.

Example 4: Molecular analysis (for example, but not limited to any of: epigenetic; genetic; translational; post-translational); Molecular analysis, for example is used by Qiagen and other companies to assess the DNA methylation and other epigenetic marks for diagnosis of various diseases such as cancer by methods including bisulfite sequencing and methylated DNA precipitation (MDIP). Molecular analysis is used for example, by the American Cancer Treatment Center of America, for the molecular profiling of various biomarkers found in the DNA of tumor-tissue samples. Such testing enables not only the diagnosis of cancers, for example, colorectal cancer, facilitates individualized-treatment.

Example 5: Cytology may be used to diagnose various cellular markers including those for thyroid cancer and other disorders/diseases. It is a test used by, for example, Quest for the diagnostic thyroid cancer. Merely by way of example, reference may be made to questdiagnostics.com.

Example 6: Protein level (post transcriptional). Examples of downstream analysis techniques may include: mass spectrometry, western blot, and analysis of proteomic biomarker panels using arrays. The analysis of intracellular proteins expression (levels) could be used to analyses the effects of a drug, chemical, non-chemical inhibitor, or biological inhibitor of a protein or a series of proteins.

This includes the measurement on the effect of knockdown/knockout/inhibition or activation on genes that may alter the RNA or protein or non coding DNA sequence. This includes proteins/RNA of the epigenome (enzymes such an the DNA methylases, DNA demethylases, histone methylases, histone demethylases, histone actetylases, and histone deacetylases etc (specifically this includes the enzymes DNMT1/2/3 and all subtypes, MBD2, MeCP2, and all histone modifying enzymes such as histone (de) actetylses (de) methylases etc.) and may be in conjuncture with analysis of the epigenetic downstream effect(s) (such as DNA methylation or a modification of the histone at either a global or gene specific level and or the analysis of RNA and or DNA).

Example 7. RNA level (transcriptional) to measure gene expression. There are numerous candidate genes identified in the literature used either individually or on a panel to discern diseases/disorders or used as companion diagnostics or biomarkers for pharmacologic and/or therapeutic intervention of numerous diseases and disorders including cancer, neurological diseases, orphan disease, and diseases/disorders of children. Furthermore, the different types of RNA can be analyzed from the isolated cells (these include microRNA and messenger RNA etc.). The analysis techniques include PCR, genome wide arrays, and biomarker panels (to name a few).

RNA downstream applications may include analyzing the cells for RNA or mRNA interferences using inhibitors such as siRNA or other chemical and/or non chemical inhibitors. This includes measuring the level or RNA by various forms of PCR, expression arrays (examples include affymetrix or agilent human genome expression arrays and custom arrays that may or may not include known biomarkers for a particular disease or disorder).

Example 8. DNA (genetic and epigenetic including DNA methylation and histone modifications). This may include techniques such as use with biomarker panels, bisulfite sequencing analysis, methylated immuno precipitation analysis, and whole genomic array platforms (agilent, affymetrix, and customized arrays including those based on gene panels).

DNA analysis may be used to measure the effect of the inhibition of methylation and demethylation both globally and gene specific. In the case of global inhibitors could include those biological and chemical (5azaC for example). In addition, it could be used to measure the effect on the histones using, for example, arrays, western blot, and mass spectrometry.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, any logic flow depicted in the accompanying figures and described herein does not require the particular order shown, or sequential order, to achieve desirable results. Other implementations may be within the scope of at least some of the following exemplary claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to collection, preservation, separation and isolation of cells from bodily fluids (e.g., saliva, urine), as well as the collection of other substances, including toxic and/or hazardous substances/fluids (as well as the preservation, separating and isolation of components thereof). In other words, elements from one or another disclosed embodiments may be interchangeable with elements from other disclosed embodiments.

REFERENCES (INCORPORATED HEREIN BY REFERENCE)

Abdolmaleky, H. M., Thiagalingam, S., Wilcox, M. (2005). Genetics and epigenetics in major psychiatric disorders: dilemmas, achievements, applications, and future scope. American Journal of Pharmacogenomics. 5(3):149-60.

Alika K. Maunakea, Iouri Chepelev, Keji Zhao. 2010. Epigenome Mapping in Normal and Disease States. Circ. Res. 107; 327-339

Baron S, Poast J, Cloyd M W. Why Is HIV Rarely Transmitted by Oral Secretions?: Saliva Can Disrupt Orally Shed, Infected Leukocytes. Arch Intern Med. 1999; 159 (3):303-310.

Becker, M. A., & Dos-Santos, M. C. (2010). Psychological stress and its influence on salivary flow rate, total protein concentration and IgA, IgG and IgM titers. Neuroimmunomodulation. 17(6):396-404.

Burdge, G. C., & Lillycrop, K. A. (2010). Nutrition, Epigenetics, and Developmental Plasticity: Implications for Understanding Human Disease. Annu. Rev. Nutr. 30:315-39.

Chouliarasa, L., Ruttena, B. P., Kenisa, F., Peerboomsa, O., Vissera, P. J., Verheya, F., van Osa, J., Steinbuscha, H. W., & van den Hovea, D. L. (2010). Epigenetic regulation in the pathophysiology of Alzheimer's disease. Progress in Neurobiology. 90(4): 498-510.

Costa, E., Grayson, R. D., & Guidotti, A. (2003). Epigenetic downregulation of GABAergic function in schizophrenia: Potential for pharmacological intervention. Molecular Interventions. 3(4): 220-229.

Dos-Santos M C, Matos-Gomes N, Makimoto F H, Katsurayama M, Santana L L, Becker M A, Paredes-Garcia E, Bertho A L. (2009). Cell Phenotyping in saliva of individuals under phycological stress. Cellular immunology. 260:39-43

Eaves, L., Silberg, J., Erkanli, A. (2003). Resolving multiple epigenetic pathways to adolescent depression. Journal of Child Psychology and Psychiatry. 44(7): 1006-1014.

Ho, S. (2010). Environmental epigenetics of asthma: An update. The Journal of Allergy and Clinical Immunology. 126(3):453-465.

Iwamoto, K., & Kato, T. (2009). Epigenetic Profiling in Schizophrenia and Major Mental Disorders. Neuropsychobiology. 60(1): 5-11.

Johnson L J and Tricker P J. (2010) Epigenomic Plasticity Within Populations: its evolutionary significance and potential. Heredity. 105: 113-121

Kappeler, L., & Meaney, M. J. (2010). Epigenetics and parental effects. Bioessays. 32: 818-827.

Kuratomi G, Iwamoto K, Bundo M, Kusumi I, Kato N, Iwata N, Ozaki N, Kato T. (2007). Aberrant DNA methylation associated with bipolar disorder identified from discordant monozygotic twins. Mol. Psychiatry. 13(4): 429-441.

Lal R., Edison L., and Chused T., (1987). Fixation and long-term storage of human lymphocytes for surface marker analysis by flow cytometry. Cytometry 9:213-219

Lister, L., Pellizzola, M., Dowen, R. H, Hawkins, R. D., Hon, G., Tonti-Filipinni, N., et al. (2009). Human DNA methylome at base resolution show widespread epigenetic differences. Nature. 462: 315-322.

Matos-Gomes, N., Katsurayama, M., Makimoto, F. H., Santana, L. L., Paredes-Garcia, E., Mastroeni, D., Grover, A., Delvaux, E., Whiteside, C., Coleman, P. D., & Rogers, J. (2010). Epigenetic changes in Alzheimer's disease: Decrements in DNA methylation. Neurobiology of Aging. 31(12): 2025-2037.

McGowan, P. O. & Kato, T. (2007). Epigenetics in mood disorders. Environmental Health and Preventive Medicine. 13(1): 16-24.

McGowen, P. O., Sasaki, A., D'Alessio, A. C., Dymov, S., Labonte, B., Szyf, M., Turecki, G., Meaney, M. (2009). Epigenetic regulation of the glucocorticoid receptor in human brain associated with childhood abuse. Nature Neuroscience. 12(3):342-8.

McGowan, P. O., Szyf, M. (2010). The epigenetics of social adversity in early life: Implications for mental health outcomes. Neurobiology of Disease. 39: 66-72.

Mill, J., Petronis, A. (2007). Molecular studies of major depressive disorder: the epigenetic perspective. Molecular psychiatry. 12: 799-814.

Peedicayil, J. (2007). The role of epigenetics in mental disorders. Indian J Med Res. 126: 105-111.

Petronis, A., Paterson, A. D., & Kennedy, J. (1999). Schizophrenia: An epigenetic puzzle? Schizophr Bull. 25(4): 639-655

Plazas-Mayorca M, Vrana K. (2011). Proteomic investigation of epigenetic in neuropsychiatric disorders: A missing link between genetics and behavior? J Proteome Research. 10: 58-65

Portela A, and Esteller, M. 2010. Epigenetic modifications and human disease. Nature Biotechnology. 28:10, 1057

Righini C A, Fraipont F, Timsit J F, Faure C, Brambilla E, Reyt, Favrot M C. (2007). Tumor-specific methylation in saliva: A promising biomarker for early detection of head and neck cancer recurrence. Clin. Cancer Res. 13(4): 1179-85

Rosas S L B, Koch w, Carvalho M G C, Wu L, Califano J, Westra W, Jen J, and Sidransky D. (2001). Promoter hypermethylation patterns of p16, O-methylguanine-DNA-methyltransferase, and death associated protein kinase in tumors of and saliva of head and neck cancer patients. Cancer Research. 61:939-42

Russo P, Lauria F, Siani A. (2010) Heritability of body weight: Moving beyond genetics. Nutrition, Metabolism and Cardiovascular Diseases. 20: 691-697

Teirling S, Souren N Y, Reither S, Zang K D, Meng-Henschel J, Leitner D, Oehl-Jaschkowits B, Walter J. (2010). Dna methylation studies on imprinted loci in male monozygotic twin pairs discordant for Beckwith-Wiedmann syndrome. Clinical Genetics. 79: 1399-004

Tsai S J, Hong C J, Liou Y J. (2010). Recent molecular genetic studies and methodological issues in suicide research. Progress in neuro-psychopharmacology and biology psychiatry Viet C T, and Schmidt B L. (2008). Methylation Array Analysis of Preoperative and Postoperative Saliva DNA in Oral Cancer Patients. Cancer Epidemiol Biomarkers Pre. 17(12): 3603-11

Zhang F F, Cardarelli, Carroll J, Zhang S, Fulda K, Gonzales K, Vishwanatha J, Morabia A, Santella R. (2011). Physical activity and global methylation in a cancer-free population. Epigenetics. 6(3) 293-299

Vlaanderen, J., Moore, L. E., Smith, M. T., Lan, Q., Zhang, L., Skibola, C. F., Rothman, N., & Vermeulen, R. (2010). Application of OMICS technologies in occupational and environmental health research; current status and projections. Occup Environ Med. 67:136-143.

[3] Gernez et al. 2010. Neutrophils in chronic inflammatory airway diseases: can we target them and how? European Respiratory Journal, 2010, Volume 35, 467-469.

[4] Singh et al. 2010. Sputum neutrophils as a biomarker in COPD: findings from the ECLIPSE study. Respiratory Research, 2010, 11:77, 1-12.

[5] Korpanty et al. 2014. Biomarkers that currently affect clinical practice in lung cancer: EGFR, ALK, MET, ROS-1, and KRAS. Frontiers in Oncology. August 2014, Volume 4, Article 204, 1-8.

[6] Kerr et al. 2014. Second ESMO consensus conference on lung cancer: pathology and molecular biomarkers for non-small-cell lung cancer. Annals of Oncology, April 2014, Volume 25, 1681-1690.

[7] Thunnissen et al. 2003. Sputum examination for early detection of lung cancer. Journal Clinical Pathology, 2003, Volume 56, 805-810.

[8] Sterlacci et al. 2014. Putative stem cell markers in non-small-cell lung cancer: a clinicopathologic characterization. Journal Thoracic Oncology. January 2014, Volume 9, Issue 1, 41-49.

[9] abcam.com

[10] Feng 2010. Identification of Human Lung Cancer Stem Cell Markers. Becton & Dickinson 2010 Research Grant Program Winning Abstract.

[11] Wu et al. 2014. Is CD133 Expression a Prognostic Biomarker of Non-Small-Cell Lung Cancer? A Systematic Review and Meta-Analysis. Plos One, June 2014, Volume 9, Issue 6, 1-8.

[12] Romanus et al. 2015. Cost-Effectiveness of Multiplexed Predictive Biomarker Screening in Non-Small-Cell Lung Cancer. Journal of Thoracic Oncology, April 2015, Volume 10, Issue 4, 586-594.

[13] Even-Desrumeaux et al. 2011. State of the Art in Tumor Antigen and Biomarker Discovery. Cancer, June 2011, Volume 3, 2554-2596.

[14] pm360online.com

[15] Same as reference 5

[16] lungcancerprofiles.com

[18] Dako Danemark A/S 2013. IHC Guidebook, Sixth Edition. Immunohistochemical Staining Methods.

[19] genome.gov

[20] advanceweb.com

[21] Faner et al. 2014. Lessons from ECLIPSE: a review of COPD biomarkers. Thorax, July 2014, Volume 69, Issue 7, 666-672.

[22] respiratory-research.com

[23] copdfoundation.org

[24] medscape.com

[25] Same as reference 3

[26] Singh et al. 2014. Eosinophilic inflammation in COPD: prevalence and clinical characteristics. European Respitory Journal, October 2014.

[27] datamonitorhealthcare.com

[28] Saha et al. 2006. Eosinophilic airway inflammation in COPD. International Journal of COPD 2006, Volume, Issue 1, 39-47

[29] Same as reference 4

[30] Welham 2004. VAP-1: a new anti-inflammatory target? Blood, May 2004, Volume 103, Issue 9

[31] Stefano et al. 2009. Association of increased CCL5 and CXCL7 chemokine expression with neutrophil activation in severe stable COPD. Thorax, November 2009, Volume 64, Issue 11, 968-975.

[32] Noguera et al. Enhanced neutrophil response in chronic obstructive pulmonary disease. Thorax March 2001, Volume 56, 432-437.

[33] Schilter et al. 2015. Effects of an anti-inflammatory VAP-1/SSAO inhibitor, PXS-4728A, on pulmonary neutrophil migration. Respiratory Research 2015, Volume 16, Issue 42, 1-14.

[34] Same as reference 27

[35] gsk.com

[36] Same as reference 27

[37] F.A. Davis Company, Presentation. Molecular Diagnostics Fundamentals, Methods and Clinical Applications, Second Edition. Chapter 7. Nucleic Acid Amplification.

[38] Sullivan, University of Mississippi Medical Center Division of Infectious Diseases. Presentation. Nucleic Acid Amplification Techniques.

[39] aidsmap.com

[40] Balamane et al. 2010. Detection of HIV-1 in Saliva: Implications for Case-Identification, Clinical Monitoring and Surveillance for Drug Resistance. The Open Virology Journal, 2010, Volume 4, 88-93.

[41] aidsmap.com

[42] The CRN Pharmacovigilance Project Genomics Working Group. Report: Specimen Collection within the CRN: A Critical Appraisal.

[43] Reynolds et al. Comparison of high density genotyping results from saliva and blood samples on Affymetrix GeneChip® GenomeWide SNP 6.0 arrays. Affymetrix Inc.

[44] Gaester et al. 2014. Human papillomavirus infection in oral fluids of HIV-1-positive men: prevalence and risk factors. Nature. Scientific Reports, October 2014, 1-5.

[45] Sindhu et al. 2014. Saliva: A Cutting Edge in Diagnostic Procedures. Journal of Oral Diseases, May 2014, 1-8.

[46] O'Neal et al. 2012. HIV Nucleic Acid Amplification Testing Versus Rapid Testing: It Is Worth the Wait. Testing Preferences of Men Who Have Sex with Men. Journal Acquired Immune Deficiency Syndrome. August 2012, Volume 60, Issue 4, 1-7.

[47]
a) cdc.gov
b) fda.gov
c) catie.ca
d) aidsmap.com
e) aidsmap.com

[48] Yang et al. 2014. Detection of Tumor Cell-Specific mRNA and Protein in Exosome-Like Microvesicles from Blood and Saliva. Plos One, November 2014, Volume 9, Issue 11, 1-10.

[49] Wong 2011. Conference Presentation: Saliva: The New Diagnostic Frontier. Oct. 27, 2011. Institute of Oral Health National Conference, Chicago IL.

[50]
a) mycancergenome.org
b) emedicine.medscape.com
c) uptodate.com
d) mayomedicallaboratories.com

[51] Wang et al. 2012. A quick and simple FISH protocol with hybridization-sensitive fluorescent linear oligodeoxynucleotide probes. RNA 2012, Volume 18, 166-175.

[52] Vyboh et al. 2012. Detection of Viral RNA by Fluorescence in situ Hybridization (FISH). Journal of Visualized Experiments, May 2012, Volume 61, 1-5.

[53] Lassen et al. 2004. Analysis of Human Immunodeficiency Virus Type 1 Transcriptional Elongation in Resting CD4 T Cells In Vivo. Journal of Virology September 2004, 9105-9114.
[54] Mens et al. Amplifying and Quantifying HIV-1 RNA in HIV Infected Individuals with Viral Loads Below the Limit of Detection by Standard Clinical Assays. Journal of Visualized Experiments, September 2011, Volume 55, 1-8.
[55] aidsmap.com
Leena George 2016: Leena George and Christopher Brightling, "Eosinophilic airway inflammation: role in asthma and chronic obstructive pulmonary disease", Therapeutic Advances in Chronic Disease, 2016, Vol 7(1) 34-51.
Fadia T. Shaya et al, "Burden of COPD, Asthma and Concomitant COPD and Asthma Among Adults—Racial Disparities in a Medicaid Population", CHEST Journal, 136/2/August 2009.

Annex 1 (referred to above) now follows as part of the present disclosure:

ANNEX 1

The disclosure additionally relates to devices, solutions and methods for collecting samples of bodily fluids or other substances, including hazardous and/or toxic substances, and in particular, a naturally expressed bodily fluid (e.g., saliva, urine). Additionally or alternatively, the disclosure relates generally to functional genetics and/or to the isolation and preservation of DNA from such bodily fluids, for later genetic studies (for example). Additionally or alternatively, the disclosure relates generally to such features suitable for home use.

WO 2003/104251 (DNA Genotek Inc.) describes a composition and method for preserving and extracting nucleic acids from a collected sample of saliva. The composition includes a chelating agent, a denaturing agent, buffers to maintain the pH of the composition within ranges desirable for DNA and/or RNA. The composition may also include a reducing agent and/or antimicrobial agent. That document also describes a saliva sample collection container having a chamber containing the composition, and a technique for releasing the composition by disestablishment of a separating barrier when a cap is fitted to the container.

While the concept of a self-contained collection and preservation device has potential for many different genetic testing applications without requiring a donor to physically visit a laboratory, such potential may be severely limited by the efficacy of the composition, and the quality of the preserved solution. Some non-limiting aspects of the invention may seek to at least mitigate such issues.

Reference is made herein to an improved sample collection device described in WO 2012/177656 and/or WO 2015/112496. The content of these application is incorporated herein by reference as if reproduced here in its entirety.

The following presents a simplified summary of the disclosure of Annex 1 in order to provide a basic, non-limiting, understanding of some aspects of the disclosure.

In one aspect, a (e.g. portable) collection device is described that is suitable for use by a sample donor, for example, without having to visit a laboratory. The sample collection device comprises a container for receiving a naturally expressed bodily fluid, for example, saliva or urine. The device further comprises a chamber containing a composition for extracting and preserving nucleic acids in the collected sample, wherein the composition is effective in extracting and preserving nucleic acids from a cell organelle. The organelle may be a mitochondrion (although the same principles may apply to other organelles).

Additionally or alternatively, in one aspect, a composition is described for use in a sample collection device for collecting a sample of a naturally expressed bodily fluid, and extracting and preserving nucleic acids in the collected sample, wherein the composition is effective in extracting and preserving nucleic acids from a cell organelle. The organelle may be a mitochondrion (although the same principles may apply to other organelles).

The nucleic acids may be DNA and/or RNA, as desired.
Mitochondrial DNA may have very different characteristics from nuclear DNA:
(i) Mitochondrial DNA is very small compared to nuclear DNA. It has the smallest chromosome encoding of only 36 genes, consists of 16600 bp.
(ii) Mitochondrial DNA is also relatively sparse in concentration compared to nuclear DNA. From about 100 to about 10,000 separate copies of mitochondrial DNA may be present per cell.
(iii) Mitochondrial DNA is inherited only from the mother.
(iv) Mitochondrial DNA is circular.
(v) Mitochrondrial DNA is very susceptible to mutation. This is one factor that may make mitochrondrial DNA of interest for research and analysis, because it is more capable of being mutated or marked than nuclear DNA. For example, it is believed that certain mutation may be a useful indicator or neurological disease that may be difficult (or impossible) to detect from nuclear DNA.

However, it is not known hitherto to extract and preserve mitochondrial DNA with a sample collection device of the type disclosed herein. The above characteristics make mitochondrial DNA difficult to extract and preserve. Firstly, the susceptibility to mutation means that mitochondrial DNA is particularly susceptible to damage and mutation by the conventional process used to lyse sample cells to extract the DNA. Secondly, the sparse concentration, and small size, of mitochondrial DNA exacerbates the difficulty of obtaining a sufficient quantity of undamaged mitochondrial DNA to provide a quality sample for downstream analysis.

In some embodiments, the composition may be configured to lyse the cell organelle (e.g. mitochondrion). Example compositions are described later.

Additionally or alternatively to either of the above, in one aspect, a composition is described for use in a sample collection device for collecting a sample of a naturally expressed bodily fluid, and extracting and preserving nucleic acids in the collected sample, wherein (i) the composition is significantly more concentrated in lysing and/or preservation agents than a conventional composition, and/or (ii) the composition has a volume not substantially larger than the volume of the bodily fluid sample for which the composition is intended.

In some embodiments, the composition may have a volume smaller than the volume of the bodily fluid sample for which the composition is intended.

By using a composition volume not substantially larger than the volume of the bodily fluid sample for which the composition is intended, the volume increase when mixing the composition with the collected sample, can be equally small. Providing a relatively small volume reduces the impact of the volume increase on the concentration of nucleic acids in the resulting mixture and/or reduces the dilution effect of the composition volume in terms of DNA concentration per unit volume.

For example, in one embodiment, the ratio of a volume of a composition, to a volume of a collected bodily fluid sample may be about 1:1. With such a ratio, the concentration of extracted and preserved nucleic acids per unit volume, is halved because the net volume doubles. Thus the concentration can remain relatively high. It is believed that by using a smaller volume of composition, the impact of the volume increase can be even further reduced. For example, if the volume of the composition is about half the volume of the bodily fluid sample, it is believed that the concentration of extracted and preserved nucleic acids per unit volume may be two-thirds the original, instead of half. The concentration per unit volume is thereby enhanced by approximately 33% compared to the 1:1 embodiment.

Using an increased concentration of lysing and/or preservation agents can compensate for the reduced volume of the composition.

Additionally or alternatively, using an increased concentration of lysing and/or preservation agents can provide for rapid lysing and/or preservation action, and/or lysing of a cell organelle within the cell, either or both of which can reduce the time during which mutation of organelle DNA (e.g., mitochondrial DNA) may occur.

Additionally or alternatively to any of the above aspects, a composition is described for use in a sample collection device for collecting a sample of a naturally expressed bodily fluid, and extracting and preserving nucleic acids in the collected sample, wherein the composition comprises: at least one lysing agent, and/or at least one preservation agent.

Optionally, the composition may comprise at least two lysing agents, optionally at least three lysing agents.

Additionally or alternatively, the composition may optionally comprise as the at least one preservation agent, at least one chemical inhibitor and/or denaturing agent, for blocking proteins and/or DNAases. Optionally, the composition may comprise at least two such chemical inhibitors and/or denaturing agents, optionally at least three such chemical inhibitors and/or denaturing agents.

Details of example compositions are further explained below.

Additionally or alternatively to any of the above aspects, in some embodiments, a composition is described comprising one or any combination of two, or all three, of:
  at least one lysing agent for liberating nucleic acids from a sample cell, the at least one lysing agent comprising at least one, optionally at least two; optionally at least three, selected from: sodium dodecyl sulfate (SDS); Triton; Triton-X; Triton 100; Triton-X 100; deoxycholate (e.g. sodium deoxycholate); cholate (e.g. sodium cholate); sodium lauroyl sarcosinate (and/or sarkosyl); maltoside (e.g. n-dodecyl-(3-D-maltopyranoside and/or DDM); glycoside (e.g. Digitonin); Tween (e.g. Tween 20 and/or Tween 80); 3-[(3-cholamidopropyl) dimethylammonio]-1-propanesulfonate (and/or CHAPS); nonyl phenoxypolyethoxylethanol (and/or Tergitol-type NP-40 and/or NP-40); sodium chloride (NaCl); lithium chloride (LiCl); potassium chloride (KCl); or a derivative (e.g. a commercial derivative) of any of the aforementioned;
  a buffer agent comprising tris and/or ethylenediaminetetraacetic acid (EDTA);
  at least one chemical inhibitor and/or denaturing agent, for blocking proteins and/or DNAases, the at least one chemical inhibitor and/or denaturing agent comprising at least one, optionally at least two, optionally at least three, selected from: 2-mercaptoethanol; $Ca^{2+}$ ions; ethylene glycol tetraacetic acid (EGTA); ethylenediaminetetraacetic acid (EDTA); sodium dodecyl sulfate (SDS); iodoacetate; urea.

Additionally or alternatively to any of the above aspects, in some embodiments, a composition is described comprising: at least one ionic surfactant (or ionic detergent); at least one non-ionic surfactant (or non-ionic detergent); and a salt. The composition may be a solution for lysing a cell and/or an organelle.

It is believed that the combination of ionic and non-ionic surfactants may have a synergistic stabilizing effect on micelle formation, and make micelle formation more tolerant to high salt concentration. This can avoid undesirable precipitation of one or more of the surfactants even in relatively high surfactant concentrations and/or high salt concentration. Enabling a solution to have both high micellular surfactant concentration(s) and high salt concentrations may enhance the cell and/or organelle lysing capabilities of the solution.

Examples of ionic surfactants or detergents include any one or more of: sodium dodecyl sulfate (SDS); deoxycholate (e.g. sodium deoxycholate); cholate (e.g. sodium cholate); sodium lauroyl sarcosinate (and/or sarkosyl); 3-[(3-cholamidopropyl)dimethylammonio]-1-propanesulfonate (and/or CHAPS); a derivative (e.g. a commercial derivative) of any of the aforementioned.

In some embodiments, ionic surfactants (or detergents) may include zwitterionic surfactants (or detergents), of which CHAPS is an example. In other embodiments, ionic surfactants (or detergents) may optionally not include zwitterionic surfactants; for example, ionic surfactants (or detergents) may include anionic or cationic surfactants (or detergents).

Examples of non-ionic surfactants or detergents include any one or more of: Triton; Triton-X; Triton 100; Triton-X 100; maltoside (e.g. n-dodecyl-(3-D-maltopyranoside and/or DDM); glycoside (e.g. Digitonin); Tween (e.g. Tween 20 and/or Tween 80); 3-[(3-cholamidopropyl)dimethylammonio]-1-propanesulfonate (and/or CHAPS); nonyl phenoxypolyethoxylethanol (and/or Tergitol-type NP-40 and/or NP-40); a derivative (e.g. a commercial derivative) of any of the aforementioned.

Examples of salt include any one of more of: sodium chloride (NaCl); lithium chloride (LiCl); potassium chloride (KCl).

In another aspect, Annex 1 discloses a bodily fluid sample collection device for the collection of naturally expressed bodily fluids (e.g. saliva), comprises a composition for extracting and preserving nucleic acids in the collected sample. In some embodiments, the composition is effective in extracting and preserving nucleic acids from a cell organelle. The organelle may be a mitochondrion. In some embodiments, the composition combines multiple lysing agents. In some embodiments, the composition comprises at least one ionic detergent, at least one non-ionic detergent, and a salt.

Without limiting the present disclosure, a numbered, itemized list of certain features and/or aspects disclosed in Annex 1 now follows:
Itemization Number:
 1. A composition for use in a sample collection device for collecting a sample of a naturally expressed bodily fluid sample, the composition effective to extract and preserve nucleic acids in the collected sample, wherein the composition is effective in extracting and preserving nucleic acids from a cell organelle.

2. The composition of item 1, wherein the organelle is a mitochondrion.
3. The composition of item 1 or 2, wherein the nucleic acids comprise DNA.
4. The composition of item 1, 2 or 3, wherein the composition comprises at least one lysing agent for lysing a cell organelle.
5. The composition of item 4, wherein the composition comprises at least two, optionally at least three, lysing agents.
6. The composition of any preceding item, wherein the composition and/or a lysing agent comprises at least one selected from: a surfactant; a detergent; a salt.
7. The composition of any preceding item, wherein the composition and/or a lysing agent comprises at least one, optionally at least two, optionally at least three, selected from, including derivatives thereof: sodium dodecyl sulfate (SDS); Triton; Triton-X; Triton 100; Triton-X 100; deoxycholate (e.g. sodium deoxycholate); cholate (e.g. sodium cholate); sodium lauroyl sarcosinate (and/or sarkosyl); maltoside (e.g. n-dodecyl-(3-D-maltopyranoside and/or DDM); glycoside (e.g. Digitonin); Tween (e.g. Tween 20 and/or Tween 80); 3-[(3-cholamidopropyl)dimethylammonio]-1-propanesulfonate (and/or CHAPS); nonyl phenoxypolyethoxylethanol (and/or Tergitol-type NP-40 and/or NP-40); sodium chloride (NaCl); lithium chloride (LiCl); potassium chloride (KCl).
8. The composition of any preceding item, wherein the composition comprises in combination (i) Triton or a derivative thereof, (ii) SDS or a derivative thereof, and (iii) a salt.
9. The composition of any preceding item, wherein the composition comprises at least one chemical inhibitor and/or denaturing agent, for blocking proteins and/or DNAases.
10. The composition of any preceding item, wherein the composition comprises at least one, optionally at least two, optionally at least three, selected from: 2-mercaptoethanol; $Ca^{2+}$ ions; ethylene glycol tetraacetic acid (EGTA); ethylenediaminetetraacetic acid (EDTA); sodium dodecyl sulfate (SDS); iodoacetate; urea.
11. A composition for use in a sample collection device for collecting a sample of a naturally expressed bodily fluid sample, the composition effective to extract and preserve nucleic acids in the collected sample, wherein the composition comprises at least one or any combination of two or all three of:
at least one lysing agent for liberating nucleic acids from a sample cell, the at least one lysing agent comprising at least one, optionally at least two; optionally at least three, selected from, including derivatives thereof: sodium dodecyl sulfate (SDS); Triton; Triton-X; Triton 100; Triton-X 100; deoxycholate (e.g. sodium deoxycholate); cholate (e.g. sodium cholate); sodium lauroyl sarcosinate (and/or sarkosyl); maltoside (e.g. n-dodecyl-(3-D-maltopyranoside and/or DDM); glycoside (e.g. Digitonin); Tween (e.g. Tween 20 and/or Tween 80); 3-[(3-cholamidopropyl)dimethylammonio]-1-propanesulfonate (and/or CHAPS); nonyl phenoxypolyethoxylethanol (and/or Tergitol-type NP-40 and/or NP-40); sodium chloride (NaCl); lithium chloride (LiCl); potassium chloride (KCl);
a buffer agent comprising tris and/or ethylenediaminetetraacetic acid (EDTA);
at least one chemical inhibitor and/or denaturing agent, for blocking proteins and/or DNAases, the at least one chemical inhibitor and/or denaturing agent comprising at least one, optionally at least two, optionally at least three, selected from: 2-mercaptoethanol; $Ca^{2+}$ ions; ethylene glycol tetraacetic acid (EGTA); ethylenediaminetetraacetic acid (EDTA); sodium dodecyl sulfate (SDS); iodoacetate; urea.
12. The composition of any preceding item, further comprising a pH buffer.
13. The composition of item 12, wherein the buffer is or comprises Tris.
14. The composition of any preceding item, wherein the composition has a pH of greater than about 8.
15. The composition of any preceding item, wherein the composition further comprises Proteinase K.
16. The composition of any preceding item, wherein the composition has an aggregate salt concentration that is greater than at least one selected from: 249 mM; 250 mM; 275 mM; 300 mM; 325 mM; 350 mM.
17. The composition of any preceding item, wherein the composition has an aggregate salt concentration that is not greater than at least one selected from: 300 mM; 2000 mM; 1000 mM; 750 mM; 500 mM.
18. The composition of any preceding item, wherein the composition has a volume that is not greater than at least one selected from: 5 ml; 4 ml; 3 ml; 2 ml; 1 ml; 750 µl; 500 µl; 250 µl; 100 µl.
19. The composition according to any preceding item, comprising Tris, SDS, Triton, NaCl and EDTA.
20. The composition according to item 19, further comprising one or more selected from: Proteinase K, sodium deoxycholate, urea.
21. The composition according to item 19 or 20, wherein the concentrations of constituents in the composition are defined by:
Tris: about (R+1)*10 mM
SDS: about (R+1)*1% (v/v)
Triton: about (R+1)*1% (v/v)
NaCl: greater than or equal to about (R+1)*250 mM
EDTA: (R+1)*5 mM
where:
R is a ratio Vs/V;
Vs is a predetermined volume of a sample Vs with which the concentration is intended to be mixed in use, and
Vc is a volume of the composition.
22. A composition for lysing cellular material, optionally according to any preceding item, the composition comprising: at least one ionic surfactant (or ionic detergent); at least one non-ionic surfactant (or non-ionic detergent); and a salt.
23. The composition of item 22, wherein the at least one ionic surfactant or detergent is selected as any one or more of: sodium dodecyl sulfate (SDS); deoxycholate (e.g. sodium deoxycholate); cholate (e.g. sodium cholate); sodium lauroyl sarcosinate (and/or sarkosyl); 3-[(3-cholamidopropyl)dimethylammonio]-1-propanesulfonate (and/or CHAPS); a derivative of any of the aforementioned.
24. The composition of item 22 or 23, wherein the at least one non-ionic surfactant or detergent is selected as any one or more of: Triton; Triton-X; Triton 100; Triton-X 100; maltoside (e.g. n-dodecyl-(3-D-maltopyranoside and/or DDM); glycoside (e.g. Digitonin); Tween (e.g. Tween 20 and/or Tween 80); 3-[(3-cholamidopropyl)dimethylammonio]-1-propanesulfonate (and/or CHAPS); nonyl phenoxypolyethoxyethanol (and/or Tergitol-type NP-40 and/or NP-40); a derivative of any of the aforementioned.

25. The composition of item 22, 23 or 24, wherein the salt is any one or more selected from: sodium chloride (NaCl); lithium chloride (LiCl); potassium chloride (KCl).

26. The composition of any of items 22 to 25, wherein the composition has an aggregate salt concentration that is greater than at least one selected from: 249 mM; 250 mM; 275 mM; 300 mM; 325 mM; 350 mM.

27. The composition of any of items 22 to 26 wherein the ionic and non-ionic surfactants or detergents form a mixed micelle population and/or mixed micelles.

28. The composition of any preceding item, further comprising ethanol.

29. The composition of any of items 1 to 27, wherein the composition is substantially ethanol free.

30. A bodily fluid sample collection device for the collection of naturally expressed bodily fluids comprising a container for receiving a naturally expressed bodily fluid, and a chamber containing a composition for extracting and preserving nucleic acids in the collected sample, wherein the composition is as defined according to any preceding item.

31. A bodily fluid sample collection device, optionally according to item 30, for the collection of a predetermined first volume of a naturally expressed bodily fluid, comprising a container for receiving a sample of the naturally expressed bodily fluid, and a chamber containing a second volume of a composition for extracting and preserving nucleic acids in the collected sample, wherein the second volume is not substantially more than, optionally smaller than, the first volume.

32. The bodily fluid sample device of item 31, wherein the second volume is defined by at least one selected from: not more than about 100% of the first volume; not more than about 90% of the first volume; not more than about 80% of the first volume; not more than about 70% of the first volume; not more than about 60% of the first volume; not more than about 50% of the first volume; not more than about 40% of the first volume; not more than about 30% of the first volume; not more than about 20% of the first volume; about 90% of the first volume; about 80% of the first volume; about 70% of the first volume; about 60% of the first volume; about 50% of the first volume; about 40% of the first volume; about 30% of the first volume; about 20% of the first volume; about a third of the first volume; about a quarter of the first volume.

33. The device of item 31 or 32, wherein the first volume is defined by at least one of: from about 0.5 ml to about 2.25 ml; from about 0.75 ml to about 2.25 ml, from about 1 ml to about 2 ml; from about 1 ml to about 1.5 ml; about 1 ml.

34. The device of item 31, 32 or 33, wherein the first volume is about 1 ml, and the second volume is about 250μl.

35. A bodily fluid sample collection device, optionally according to any of items 30 to 34, for the collection of a sample of a naturally expressed bodily fluid, comprising a container for receiving a sample of the naturally expressed bodily fluid, and a chamber containing a composition for extracting and preserving nucleic acids in the collected sample, wherein the volume of the composition is defined by at least one selected from: from about 100 μl to about 1 ml; at least about 100 μl and less than 1 ml; from about 250 μl to about 750 μl; at least about 100 μl; at least about 250 μl; at least about 500 μl; less than 1 ml; less than about 750 μl; less than about 500 μl; about 100 μl; about 250 μl; about 500 μl; or about 750 μl.

36. Use in a sample collection device, of a composition as defined in any of items 1 to 29, for extracting and preserving nucleic acids in a sample of a naturally expressed bodily fluid.

37. Use of proteinase K in a process for the extraction and preservation of mitochondrial DNA using a sample collection device for home use.

Although various aspects of the disclosure have been highlighted above, this does not limit the scope of the disclosure. Protection is claimed for any novel feature and/or idea described herein and/or illustrated in the drawings whether or not emphasis has been placed thereon.

Non-limiting embodiments relating to Annex 1 are described below, by way of example only, with reference to FIGS. 4, 5 and 8 of the accompanying drawings.

Referring to FIGS. 4 and 5, a sample collection device 10 is depicted of a type that may be suitable for home use, or at least without the need to visit a laboratory. The sample collection device 10 may, for example, be portable and/or be provided to a user at home (for example, via a postal or courier delivery), for the user to donate a sample of a naturally expressed bodily fluid. The bodily fluid may, for example, be saliva or urine. The following description focuses on saliva, but it will be appreciated that the same principles may be applied to urine, or to another naturally expressed bodily fluid.

In the illustrated examples for Annex 1, a composition 12 is provided for extracting and/or preserving nucleic acids in the collected bodily fluid sample. In use, the composition is intended to be mixed with the collected bodily fluid sample, for example, upon closing the device to seal it closed. The device 10 may then be returned to the sender, or sent to a collection agent or to a laboratory for analysis, for example, genetic analysis.

A function of the composition 12 may be to extract nucleic acids from the bodily fluid sample, and/or to preserve the extracted nucleic acids (or the bodily fluid sample). The nucleic acids may be DNA and/or RNA.

In some embodiments, the composition 12 may be effective to lyse a cell organelle (for example, a mitochondrion) and/or preserve extracted organelle nucleic acids.

In some embodiments, the composition 12 may avoid or reduce, mutation, damage or other degradation, of DNA in the collected sample, thereby providing sufficient time for the device to be returned for analysis. The composition 12 may be effective to preserve extracted nucleic acids at room temperature or a period of at least a week, optionally at least two weeks, optionally at least three weeks, optionally at least a month, or even longer.

The composition 12 may be a liquid. Further details of examples of the composition are described later below.

The composition 12 may optionally be stored in an internal chamber 14 of the device, and released to mix with the collected bodily fluid sample when, for example, the user seals the device closed or performs some other manipulation of the device 10.

FIGS. 4 and 5 illustrate two alternative examples of collection device 10. The device 10 may generally comprise a first body (e.g. tube) 16 having a mouth 18 and defining a collection region 20 for the naturally expressed bodily fluid introduced into the device through the mouth 18. The device 10 may further comprise a second body (e.g. closure) 22 attachable to or over the mouth 18 to seal the device 10 closed after the donated sample has been introduced. In the example of FIG. 4, the chamber 14 containing the composition 12 is provided in the second body (e.g. closure) 22. In the example of FIG. 5, the chamber 14 containing the composition is provided in the first body (e.g. tube) 16. In either example, the chamber 14 is configured to be opened by a mechanism (shown schematically at 24), to communicate with the collection region 20. The opening mechanism 24 may be responsive to fitting the second body (e.g. closure) 22 to the first body (e.g. tube) 16, or to some other manual manipulation of the device 10. Various mechanism 24 are envisaged, including but not limited to one or more selected from: release of an internal closure or cap, opening of a tap, rupture of a frangible wall, removal or displacement of an internal cover, relative rotation of a cap or nut.

Optionally, further details of exemplary constructions of device 10 and opening mechanisms 24 are provided in the aforementioned WO 2012/177656 and WO 2015/112496 incorporated herein by reference.

The device 10 may be configured for collection of a predetermined sample volume "Vs" of the naturally expressed bodily fluid. The device may, for example, include a visual fill scale, or a fill line (e.g. indicated at 26) or other indicia, to indicate when the predetermined sample volume Vs has been attained. In some embodiments, the sample collection space may have a size that is equal to the predetermined volume Vs, or the sample collection space may be larger in volume. By way of example only, the predetermined volume Vs may in some embodiments be at least about 1 ml, or at least about 2 ml, or at least about 3 ml, or at least about 4 ml, or at least about 5 ml, or more. By way of example only, the predetermined volume Vs may in some embodiments be not more than about 5 ml, or not more than about 4 ml, or not more than about 3 ml, or not more than about 2 ml, or not more than about 1 ml. By way of example only, in some embodiments, the predetermined volume Vs may in some embodiments be from about 1 ml to about 5 ml, optionally from about 1 ml to about 4 ml, optionally from about 1 ml to about 3 ml, optionally from about 1 ml to about 2 ml. By way of example only, the predetermined volume Vs may in some embodiments be about 1 ml, or about 2 ml, or about 3 ml, or about 4 ml, or about 5 ml.

In some embodiments, the volume "Vc" of the composition 12 may be not substantially larger than, or optionally smaller than, the predetermined sample volume Vs. By way of example only, the composition volume Vc may in some embodiments, be not more than about 100% of Vs, or not more than about 90% of Vs, or not more than about 80% of Vs, or not more than about 70% of Vs, or not more than about 60% of Vs, or not more than about 50% of Vs, or not more than about 40% of Vs, or not more than about 30% of Vs, or not more than about 20% of Vs. By way of example only, the composition volume Vc may in some embodiments, be about 100% of Vs, or about 90% of Vs, or about 80% of Vs, or about 70% of Vs, or about 60% of Vs, or about 50% of Vs, or about 40% of Vs, or about 30% of Vs, or about 20% of Vs. By way of example only, the composition volume Vc may in some embodiments be about a third of Vs, or about a quarter of Vs. The composition volume Vc may be same size as the interior space of the chamber 14 in order to fill the chamber 14, or the composition volume Vc may smaller, partly filling the chamber 14.

By making the composition volume Vc not substantially larger than, or optionally smaller than, the predetermined sample collection volume Vs, the volume increase when mixing the composition 12 with the collected sample, can be equally small. The volume increase may be equivalent to dilution of the sample in terms of DNA concentration per unit volume. FIG. 8 illustrates schematically the impact of dilution on DNA sample concentration per unit volume, depending on the composition volume Vc. The horizontal axis represents a ratio R of sample volume Vs to composition volume Vc, over a range of ratios R=Vs/Vc from 1/1 to 5/1 (or R=from 1 to 5). The vertical axis represents the fraction of the DNA concentration per unit volume after mixing with the composition volume, compared to the original sample volume. The value varies as the function Vs/(Vs+Vc), and is equivalent to dilution by the composition volume.

In some embodiments disclosed herein, the ratio Vs/Vc may be about 1/1 (or R≈1). It can be seen in FIG. 8 that such a composition volume Vc reduces the DNA concentration per unit volume to 50% of the original amount, which is eminently satisfactory. However, it is believed that by using a smaller composition volume Vc (equivalent to a larger ratio of sample volume Vs to composition volume Vc), the concentration of DNA per unit volume can be increased compared to the 1/1 ratio embodiment(s). For example, using a composition volume of half the sample volume, equivalent to a sample volume Vs to composition volume Vc ratio of 2/1 (R=2), it is believed that the concentration of DNA can be increased, for example, by up to 66% of the original amount, which is a 30% improvement compared to 1/1 ratio embodiment(s). Using a composition volume Vc of one-third of the sample volume Vs, equivalent to a sample volume Vs to composition volume Vc ratio of 3/1 (R=3), it is believed that the concentration of DNA can be increased, for example, by up to 75% of the original amount, which is a 50% improvement compared to the 1/1 ratio embodiment(s). Using a composition volume Vc of one-quarter of the sample volume Vs, equivalent to a sample volume Vs to composition volume Vc ratio of 4/1 (R=4), it is believed that the concentration of DNA can be increased, for example, by up to 80% of the original amount, which is a 60% improvement compared to the 1/1 ratio embodiment(s).

Achieving a desirably high DNA concentration per unit volume may provide important advantages for downstream analysis. Firstly, modern automated testing procedures tend to use only small sample volumes. Ensuring that even a small volume of the sample, after extraction and preservation, contains a good concentration of the DNA is important to be able to benefit from automated testing. Secondly, in a collected sample, mitochondrial DNA is much sparser in concentration compared to much more preponderant nuclear DNA. Improving the overall concentration of DNA per unit volume helps increases the sensitivity of automated testing to such sparse DNA. It may contribute to enabling detection of mitochondrial DNA, using automated testing of sample collected in a relatively simple collection device, which is understood not to be possible using devices that are currently available commercially.

In one specific example, the predetermined sample volume Vs may be about 2 ml, and the composition volume Vc may be about 2 ml. In another specific example, the predetermined sample volume Vs may be about 1 ml, and the composition volume Vc may be about 1 ml. In another specific example, the predetermined sample volume Vs may be about 1 ml, and the composition volume Vc may be about 2500.

Additionally or alternatively to any of the above, and by way of example only, the composition volume Vc may in some embodiments be from about 100 μl to about 1 ml inclusive (or optionally less than 1 ml). Additionally or alternatively, the composition volume Vc may optionally be at least about 100 µl, optionally at least about 250 µl, optionally at least about 500 µl. Additionally or alternatively, the composition volume may optionally be about 1 ml, optionally less than 1 ml, optionally less than about 750 µl, optionally less than about 500 µl. By way of example only, the composition volume Vc may in some embodiments be about 100 µl, or about 250 µl, or about 500 µl, or about 750 µl.

The concentrations of the active components of the composition 12 may be varied as appropriate to compensate for using a small composition volume Vc. For example, when using a composition volume Vc of about half that of the benchmark, the concentrations of the active components of the composition 12 may be doubled or more compared to concentrations of active components of a benchmark composition 12. Varying the compositions of the active ingredients can provide at least the same (or better) extraction and preservation capabilities despite the smaller composition volume Vc. More detailed explanation of component concentrations is discussed later.

Additionally or alternatively to the above features of reducing dilution by using a small composition volume Vc (e.g. not substantially larger than, or optionally smaller than, the sample volume Vs), further features of the present disclosure may relate to the constituents of the composition 12. These features relating to the constituents may be used irrespective of the ratio of the sample volume Vs to the composition volume Vc, although the ratio may be useful to determining suitable concentrations of the constituents in the composition.

In some embodiments, the composition may comprise any one or more selected from:
  (i) at least one cell and/or organelle lysing agent for lysing cells and/or organelles to liberate nucleic acids therefrom. Suitable lysing agents may include one or more surfactants; and/or one or more detergents; and/or one or more salts. An example surfactant may be sodium dodecyl sulfate (SDS), although other surfactants may be used additionally or alternatively. Example detergents may be Triton (e.g. Triton 100; Triton-X; Triton-X 100); and/or deoycholate (e.g. sodium deoxycholate), although other detergents may be used additionally or alternatively. Example salts may be selected from: sodium chloride (NaCl); and/or lithium chloride (LiCl); and/or potassium chloride (KCl), although other salts may be used additionally or alternatively. Additional surfactants and/or detergents are further described below. For the avoidance of doubt, where the context permits, the terms "surfactant" and "detergent" may be used interchangeably, and are intended to be read interchangeably. Also, where surfactants or detergents are mentioned by name, the scope is intended to cover equally any derivative (e.g. a commercial derivative).

The surfactant and/or detergent can solubilize cellular and membrane components to break the membrane. The salt can regulate the osmolarity.

In some embodiments, at least two lysing agents (e.g. selected from the above) are used in combination, optionally at least three lysing agents (e.g. selected from the above) are used in combination.

In some embodiments, the salt concentration (in the composition 12 and/or the combination of composition 12 when mixed with the sample) may be at least 250 mM, optionally greater than 250 mM. This salt concentration may be the aggregate salt concentration, or the concentration of at least one or more major salt components. In some embodiments, this salt concentration may be at least 300 mM, optionally in the range of 300-750 mM. Such a concentration is higher than would be conventionally used, and may contribute to an organelle lysing ability of the composition 12.

In some embodiments, it is believed beneficial to use a non-ionic surfactant and/or detergent (e.g. Triton) in combination with an ionic surfactant and/or detergent (e.g. SDS). The ionic and non-ionic surfactants and/or detergents may buffer each other, and stabilize the aggregation of the surfactants to form micelles desirably, even in a relatively high salt concentration (for example, as in the preceding paragraph). For example, Triton may have a stabilizing effect on the SDS, preventing or reducing risk of precipitation of the SDS that might otherwise occur in a relatively high salt concentration. Additionally or alternatively, for example, SDS may stabilize the formation of Triton micelles, even in the presence of the relatively high salt concentration.

It is believed that the stabilizing effects of the combination of ionic and non-ionic surfactants and/or detergents may be explained by the following, although this is not intended to limit the scope of the present disclosure in any way. In some embodiments, the compositions may include both (i) surfactant/detergent and (ii) salt components. Detergents are surfactants and they are used to disrupts cell membranes, thus assist with cell lysis and facilitate the release of intracellular materials in a soluble form. Detergents break protein-protein, protein-lipid, and lipid-lipid associations. Further, detergents denature proteins and various other macromolecules and prevent the non-specific binding of immunochemical assays and protein crystallization.

Surfactants/detergents dissolved in solution may tend to aggregate to form so-called micelles. All detergents at a specific concentration will form micelles, this concentration is referred to as the critical micelle concentration (CMC). Once CMC has been reached the detergent monomers form micelles. At concentrations higher than the CMC both micelles and monomers exist in solution alongside other non-micellar phases, which may not be soluble in water.

An ionic surfactant/detergent (e.g. SDS) forms ionic micelles. When these micelles (if alone) are exposed to high salt concentrations, the micelles break and the SDS precipitates out of the solution and does not have the desired effect within the solution.

Triton X is another detergent, but whereas SDS is ionic, triton-x is non-ionic. When both SDS and triton are dissolved in the solution the micelle population is one of both ionic (SDS) and non-ionic (triton) micelles and considered a mixed micelle population. This mixed micelle population has a much higher tolerance to salt concentrations and the non-ionic micelles buffers against the effects of salt on the ionic micelles.

Temperature, pH and salt concentration can each affect the CMC of a solution (see below for detailed explanation of each). Therefore, altering any of the above mentioned may lead to the formation of a precipitate. The concentration of detergent required to form the micelles is specific. Example buffers disclosed herein contain additional sodium in the form of NaCl, which decreases the critical micelle concentrations, thus exceeding the CMC dramatically and risking precipitation the SDS to precipitate were it not for the presence of the complementary ionic/non-ionic surfactant.

The combination of SDS and Triton X is synergistic in terms of lowering the CMC and leading to the formation of larger mixed-ionic/non-ionic micelles. Concentrations and ratios of the two detergents play a role in determining the stability of the micelle. Therefore, these mixed detergent micelles may be more stable in a high salt buffer, thus preventing any precipitation of SDS. The combination of SDS and Triton-X is likely forming larger, mixed micelles with enhanced stability, as well as greater water molecule association (due to the NaCl concentration), and together contributing to the lack of SDS precipitation.

Synergistically, the presence of NaCl may also effect the micelle formation of triton-X, by reducing the CMC, increasing the size of micelles formed, and a greater number of water molecules non-specifically bonded with the micelle. It is believed that this can also be buffered by a mixed micelle population (ie addition of ionic micelles) in accordance with the principles disclosed herein.

Other detergents that may be used and do not alter biological activity include: 2% Tween-20, NP40, deoxycholate 0.1-1%.

Below are two non-limiting tables of example detergents: Table 1 lists the categories of detergents and Table 2 lists example applications of each detergent as described herein.

TABLE 1

| Type | Chemicals |
| --- | --- |
| ionic | sodium dodecyl sulfate (SDS), deoxycholate, cholate, sarkosyl |
| non-ionic | triton X-100, DDM, digitonin, tween 20, tween 80, NP-40 |

TABLE 2

| Detergent | MW (Da) monomer | MW (Da) micelle | CMC (mM) 25° C. | Aggregation No. | Cloud Point (° C.) | Avg. Micellar Weight | Strength | Dialyzable | Applications |
| --- | --- | --- | --- | --- | --- | --- | --- | --- | --- |
| SDS | 289 | 18,000 | 7-10 | 62 | >100 | 18,000 | Harsh | Yes | Cell lysis, Electrophoresis, WB, hybridization |
| Triton X-100 | 625 | 90,000 | 0.2-0.9 | 100-155 | 65 | 80,000 | Mild | No | Enzyme immunoassays, IP, Membrane solubilization |
| CHAPS | 615 | 6,150 | 6 | 10 | >100 | 6,150 | Mild | Yes | IEF, IP |
| NP-40 | 680 | 90,000 | 0.059 | | 45-50 | | Mild | No | IEF |
| n-dodecyl-β-D-maltoside | 511 | | 0.15 | 98 | | 50,000 | | | Protein Crystalization |
| Tween-20 | 1228 | | 0.06 | | 76 | | mild | No | WB, ELISA, Enzyme immunoassays |
| Digitonin | 1229 | 70,000 | <0.5 | 60 | | 70,000 | Mild | No | Membrane solubilization |

(ii) a buffer agent, for example, comprising or consisting of Tris and/or ethylenediaminetetraacetic acid (EDTA). The combination Tris and EDTA can buffer the solution and eliminate magnesium (inhibits DNAases). The combination can provide a basic DNA storage buffer. The EDTA can degrade the RNA (if desired).

In some embodiments, the pH of the sample and composition, after mixing together, may be slightly basic, for example, from about 7.4 to about 8. The pH of the composition 12 alone (e.g. prior to mixing with the sample) may be higher. The pH of the composition 12 alone may be at least about 8, optionally greater than 8, for example, about 8.3

(iii) at least one chemical inhibitor and/or denaturing agent to block proteins and/or DNAases. Suitable inhibitors and/or denaturing agents may include one or more selected from: 2-mercaptoethanol; $Ca^{2+}$ ions; ethylene glycol tetraacetic acid (EGTA); ethylenediaminetetraacetic acid (EDTA); sodium dodecyl sulfate (SDS); iodoacetate; urea.

As mentioned above, EDTA is a chelating agent of divalent cations such as $Mg^{2+}$ which is a cofactor for DNAase nucleases). In some embodiments, the EDTA serves simultaneously as a buffer agent and a denaturing agent.

(iv) Proteinase K for eliminating proteins. Proteinase K may be more effective in combination with SDS. For example, Proteinase K may be up to about ten times more effective on proteins that have been denatured, and SDS is effective as a protein denaturant. Proteinase K may avoid being inhibited by SDS or EDTA or other chemicals and protein inhibitors in solution. In some examples, where long term stability of Proteinase K might be considered an issue, this can generally be overcome by increasing the amount of Proteinase K in the composition 12, thereby pre-compensating for expected partial loss over time. By way of example only, the amount of Proteinase K in the composition 12 and/or in the combination of the composition 12 and sample after mixing together, may be between about 30 and 70 mg/ml, optionally between about 40 and optionally about 50 mg/ml.

In some embodiments, the aggregate salt concentration may be less than about 3000 mM, optionally less than about 2000 mM, optionally less than about 1000 mM, optionally less than about 750 mM, optionally less than about 500 mM. The salt concentration may be additive amongst all salt components in the composition 12 (including EDTA, for example). An overly high total salt concentration may restrict the ability to isolate DNA in later processing of the collected and preserved sample for genetic analysis. The salt concentration may be that referred to when mixed with saliva, or that of the composition in isolation.

One specific example of the composition 12 may include Tris, SDS, Triton, NaCl and EDTA. Optionally, the composition may include one or more selected from: Proteinase K, sodium deoxycholate, urea. In one example, the relative concentrations of the constituents, determined in the combination of both the composition 12 and the saliva sample mixed together, may be as in Table 3 below:

TABLE 3

| Tris | 10 mM |
|---|---|
| SDS | 1% (v/v) |
| Triton | 1% (v/v) |
| NaCl | ≥250 mM (optionally 250-350 mM; optionally 300-350 mM) |
| EDTA | 5 mM |
| +Optionals: | |
| Proteinase K | 450 mg/4 ml |
| sodium deoxycholate | 0.1% (w/v) |
| urea | 8M |

The concentrations may be varied, individually and independently, by up to 5%, optionally up to 10%, optionally up to 20%, within the scope of this specific example.

As mentioned above, the concentrations are desired concentrations in the solution containing both the composition 12 and the saliva sample. The concentrations of the constituents in the composition 12 alone may depend on the ratio R of the sample volume Vs to composition volume Vc (R=Vs/Vc) as described hereinbefore. The concentrations may vary according to a concentration multiplier of (R+1) or ((Vs/Vc)+1). General values, and some specific examples are illustrated in Table 4 below:

TABLE 4

| Constituent | General Concentration in Composition | Example 1: Vs = Vc = 2 ml (R = 1/1) | Example 2: Vs = 2 ml; Vc = 1 ml; R = 2/1 |
|---|---|---|---|
| Tris | (R + 1)*10 mM | 20 mM | 30 mM |
| SDS | (R + 1)*1% (v/v) | 2% (v/v) | 3% (v/v) |
| Triton | (R + 1)*1% (v/v) | 2% (v/v) | 3% (v/v) |
| Nad | (R + 1)* 250 mM | 500 mM | 750 mM |
| EDTA | (R + 1)*5 mM | 10 mM | 15 mM |
| +Optionals | | | |
| Proteinase K | (R + 1) * 450 mg/4 ml | 900 mg | 1350 mg |
| sodium deoxycholate | (R + 1)*0.1% (w/v) | 0.2% (w/v) | 0.3% (w/v) |
| urea | (R + 1)*8M | 16M | 24M |

Again, the concentrations may be varied, individually and independently, by up to 5%, optionally up to 10%, optionally up to 20%, within the scope of these specific examples.

The present disclosure also contemplates, within its scope:
(a) Varying the percentage of SDS, including down to 0% (omitting SDS).
(b) Varying the percentage of triton, including down to 0% (omitting Triton).
(c) Adding KCl and/or LiCl (salt that maintains ionic strength of the buffer), either as a substitute for the NaCl (omitting NaCl), or in combination with NaCl as a complement.
(d) Varying the individual and/or aggregate salt concentration(s).
(e) Adding Proteinase K, for example in a quantity as described above.
(f) Adding 0.1-1% of sodium deoxycholate, which is a biological detergent capable of solubilizing membrane and cellular components, and may increase organelle lysis. The sodium deoxycholate may be used to substitute SDS and/or Triton, or used in combination with both. The relative percentages of SDS and/or Triton may also be varied. (For example, the range quoted above may refer to the composition when mixed with saliva. The concentration may be increased in the composition alone, in accordance with the factor R+1 described herein.)
(g) Adding urea. Urea may increase protein denaturation and increase cell lysis. The percentages of SDS and/or triton, and/or other denaturing agents may be varied.
(h) using one or more other ionic and/or non-ionic surfactants and/or detergents in addition to, or as an alternative to, SDS and/or triton.

If desired, according to an intended application, the composition 12 may further comprise ethanol. Alternatively, if desired, the composition 12 may be substantially free of ethanol.

In some embodiments, the composition 12 is effective in extracting and preserving nucleic acids from a cell organelle. The organelle may, for example, be a mitochondrion.

Extracting and preserving mitochondrial DNA is known to be difficult. Mitochondrial DNA is highly susceptible to mutation by conventional lysing techniques, and is very sparse in concentration compared to nuclear DNA. This results in such DNA being difficult to extract and preserve undamaged in sufficient quantity for downstream analysis, especially using a sample collection device of the type for home use. In a laboratory environment different from a sample collection device for home use, the general wisdom for obtaining mitochondrial DNA is to lyse cells very slowly and delicately under controlled conditions that do not present significant environmental impact, so as reduce the risk of damage to the mitochondrial DNA.

Some embodiments of the present disclosure present a different approach. By using multiple lysing agents in combination, each in the high range of suggested use, for example, at least two lysing agents, optionally at least three lysing agents, or more, it is believed that not just cell membranes, but also organelle membranes may be lysed to liberate quickly nucleic acids from a cell organelle, thereby reducing the time during which lysing damage may occur.

Additionally or alternatively, by using multiple chemical inhibitor and/or denaturing agents in combination, each in the high range of suggested use, for example at least two such agents, optionally at least three such agents, it is believed that the extracted nucleic acids can be protected quickly from damage by surrounding environment materials, thereby reducing the amount of organelle DNA that is damaged.

Both of the above techniques provide surprising advantages compared to the conventional laboratory wisdom of a slow and delicate approach under controlled conditions that do not present significant environmental impact on organelle DNA. Using the above techniques in combination can provide surprisingly efficacy.

The compositions described herein may find use in many different applications for lysing cellular material to extract cellular components. The preferred embodiments are described in the context of DNA extraction, for example, organelle DNA extraction, but the composition is not limited only to such use.

The invention claimed is:
1. A method of diagnosing and/or monitoring cancer in a subject, comprising:
obtaining a saliva sample from the subject;
stabilizing cells, proteins, free-floating DNA, and free-floating RNA in the saliva sample by contacting the saliva sample with a preservation solution to form a mixture, wherein the proteins, free-floating DNA, and free-floating RNA are extracellular components of the saliva sample, wherein the preservation solution includes paraformaldehyde, at least one serum protein from human and/or other animal species, and sodium azide, and wherein the preservation solution is buffered at a pH from 6.4 to 8.4;

storing the mixture at room temperature;

subsequently separating the proteins, free-floating DNA, and free-floating RNA from the cells; and analyzing two or more analytes selected from the proteins, free-floating DNA, and free-floating RNA to diagnose and/or monitor the cancer, wherein the step of analyzing comprises molecular analysis.

2. The method of claim 1, wherein the cancer is lung cancer, lung carcinoma, leukemia, or non-small cell lung carcinoma.

3. The method of claim 1, wherein the at least one serum protein from human and/or other animal species comprises fetal bovine serum.

4. The method of claim 3, wherein the preservation solution comprises 1% (v/v) paraformaldehyde, 1% (v/v) fetal bovine serum, and 0.01% (w/v) sodium azide, and the preservation solution is buffered at a pH of 7.4.

5. The method of claim 1, wherein the saliva sample and the preservation solution are contacted at a 1:1 ratio by volume.

6. The method of claim 1, wherein the proteins, free-floating DNA, and/or free-floating RNA are separated from the cells by centrifugation.

7. The method of claim 1, wherein the step of analyzing comprises sequencing.

8. The method of claim 7, wherein the step of analyzing comprises whole genome sequencing.

9. The method of claim 7, wherein the step of analyzing comprises RNA sequencing.

10. The method of claim 7, wherein the step of analyzing comprises DNA sequencing.

11. The method of claim 7, wherein the step of analyzing comprises epigenetic sequencing.

12. The method of claim 1, further comprising determining a drug treatment for the subject.

13. The method of claim 1, further comprising analyzing the cells.

14. The method of claim 1, wherein the cancer is lung cancer.

15. The method of claim 1, wherein the two or more analytes are selected from free-floating DNA and free-floating RNA.

16. A method of diagnosing and/or monitoring, and treating cancer in a subject, comprising:

obtaining a saliva sample from the subject;

stabilizing cells, proteins, free-floating DNA, and free-floating RNA in the saliva sample by contacting the saliva sample with a preservation solution to form a mixture, wherein the proteins, free-floating DNA, and free-floating RNA are extracellular components of the saliva sample, wherein the preservation solution includes paraformaldehyde, at least one serum protein from human and/or other animal species, and sodium azide, and wherein the preservation solution is buffered at a pH from 6.4 to 8.4;

storing the mixture at room temperature;

subsequently separating the proteins, free-floating DNA, and free-floating RNA from the cells;

analyzing two or more analytes selected from the proteins, free-floating DNA, and free-floating RNA to diagnose and/or monitor the cancer, wherein the step of analyzing comprises molecular analysis;

determining a drug treatment for the subject; and administering the drug treatment to the subject.

17. The method of claim 16, wherein the two or more analytes are selected from free-floating DNA and free-floating RNA.

18. A method of diagnosing and/or monitoring cancer in a subject, comprising:

obtaining a saliva sample from the subject;

stabilizing cells, proteins, free-floating DNA, and free-floating RNA in the saliva sample by contacting the saliva sample with a preservation solution to form a mixture, wherein the proteins, free-floating DNA, and free-floating RNA are extracellular components of the saliva sample, wherein the preservation solution includes paraformaldehyde, at least one serum protein from human and/or other animal species, and sodium azide, and wherein the preservation solution is buffered at a pH from 6.4 to 8.4;

storing the mixture at room temperature;

subsequently separating the proteins, free-floating DNA, and free-floating RNA from the cells; and analyzing two or more analytes selected from the proteins, free-floating DNA, and free-floating RNA to diagnose and/or monitor the cancer;

wherein the cancer is lung cancer.

* * * * *